US006086902A

United States Patent [19]

Zamb et al.

[11] Patent Number: 6,086,902

[45] Date of Patent: Jul. 11, 2000

[54] RECOMBINANT BOVINE HERPESVIRUS TYPE 1 VACCINES

[75] Inventors: Timothy Zamb, Setauket, N.Y.; Xiaoping Liang; Lorne A. Babiuk, both of Saskatoon, Canada

[73] Assignee: University of Saskatchewan, Saskatoon, Canada

[21] Appl. No.: 08/303,861

[22] Filed: Sep. 9, 1994

Related U.S. Application Data

[63] Continuation-in-part of application No. 08/051,448, Apr. 19, 1993, abandoned.

[51] Int. Cl.[7] ..................... A01N 37/18

[52] U.S. Cl. ..................... 424/299.1; 424/204.1; 424/205.1

[58] Field of Search ..................... 424/197.1, 201.1, 424/202.1, 229.1, 243.1, 204.1, 205.1, 299.1; 435/69.1, 172.1, 252.3; 514/320.1, 44; 536/23.72

[56] References Cited

U.S. PATENT DOCUMENTS

| | | | |
|---|---|---|---|
| 5,128,129 | 7/1992 | Kit et al. | 424/89 |
| 5,151,267 | 9/1992 | Babiuk et al. | 424/89 |
| 5,206,163 | 4/1993 | Renard et al. | 435/240.2 |
| 5,601,816 | 2/1997 | Kit et al. | 424/93.2 |

FOREIGN PATENT DOCUMENTS

| | | | |
|---|---|---|---|
| 0271003 | 6/1988 | European Pat. Off. | C12N 15/00 |
| 0326127 | 8/1989 | European Pat. Off. . | |
| 0471457 | 2/1992 | European Pat. Off. . | |
| WO 92/21751 | 12/1992 | WIPO . | |
| 93/02104 | 2/1993 | WIPO | C07K 7/10 |
| WO 93/02104 | 2/1993 | WIPO . | |

OTHER PUBLICATIONS

Kit et al."Blocking ELISA for distinguishing infectious bovine rhinotracheitis virus (IBRV) infected animals from those vaccinated with a gene deleted marker vaccine". Journal of Virological Methods., vol. 40, pp. 45–56, 1992.

Barker et al. "Identification of three genes nonessential for growth in cell culture near the right terminus of the unique sequences of long component of herpes simplex virus 1". Virology. vol. 177, pp. 684–691, 1990.

Talens et al. "Efficacy of viral components of nonabortigenic combination vaccine for prevention of respiratory and reproductive system disease in cattle". JAVMA. vol. 194, No. 9, pp. 1273–1280, May 01, 1989.

Hutchings et al. "lymphocyte proliferative responses to separated bovine herpesvirus 1 proteins in immune cattle". Journal of Virology., vol. 64, No. 10, pp. 5114–5122, Oct. 1990.

Hughes et al. "Immunopotentiation of bovine herpes virus subunit vaccination by interleukin 2". Immunology. vol. 74, pp. 461–466, 1991.

Frey et al. "One year antibody responses of four inactivated infectious bovine rhinotracheitis–bovine viral diarrhea vaccines". Bovine Practitioner. No. 24, pp. 18–21. Nov. 1989.

Fehler et al. "Glycoprotein IV of bovine herpesvirus 1 expressing cell line complements and rescues a conditionally lethal viral mutant". Journal of Virology. vol. 66, No. 2, pp. 831–839, Feb. 1992.

Hurk et al. "Protection of cattle from BHV–1 infection by immunization with a recombinant glycoprotein IV". Vaccine. vol. 11, Issue 1, pp. 25–35, 1993.

Hughes et al. "Multiple administration with IL–2 potentiates antigen specific responses to subunit vaccination with bovine herpesvirus–1 glycoprotein IV". Vaccine. vol. 10, Issue 4, pp. 226–230, 1992.

Kowalski et al. "Heat shock promoter–driven synthesis of secreted bovine herpesvirus glycoproteins in transfected cells". Vaccine. vol. 11, Issue 11, pp. 1100–1107, 1993.

Gerber et al., "Local and systemic cellular and antibody immune responses of cattle to infectious bovine rhino–tracheitis virus Vaccines administered intranasally or intramuscularly" *Am. J. Vet. Res.* (1978) 39(5):753–760.

Jericho et al., "The effect of dose, route and virulence of bovine herpesvirus 1 vaccine on experimental respiratory disease in cattle" *Can. J. Com. Med.* (1983) 47:133–139.

Pastoret et al., "Reactivation of temperature–sensitive and non–temperature–sensitive infectious bovine rhinotracheitis vaccine virus with dexamethasone" *Infect. Immun.* (1980) 29(2):483–488.

Babiuk et al. "Protection of cattle from bovine herpesvirus type I (BHV–1) Infection by immunization with individual viral glycoproteins" *Virology* (1987) 159:57–66.

van Drunen Little–van den Hurk et al., "Synthesis, cellular location, and immunogenicity of bovine herpesvirus 1 glycoproteins gI and gIII expressed by recombinant vaccinia virus" *Vaccine* (1990) 8:358–368.

Hughes et al., "Functional and topographical analyses of epitopes on bovine herpesvirus type 1 glycoprotein IV" *Arch. Virol.* (1988) 103:47–60.

Mayfield et al., "Cloning and cleavage site mapping of DNA from bovine herpesvirus 1 (Cooper Strain)" *J. Virol.* (1983) 47(1):259–264.

(List continued on next page.)

*Primary Examiner*—Jeffrey Stucker
*Attorney, Agent, or Firm*—Morrison & Foerster, LLP

[57] ABSTRACT

Vaccines compositions comprising a pharmaceutically acceptable vehicle and a mutant bovine herpesvirus 1 (BHV-1) wherein (i) at least one non-essential gene of wild-type BHV-1 is deleted and optionally replaced with a gene selected from the group consisting of a foreign gene, a gene encoding a BHV-1 immunogen and a mutant analog of a gene encoding a BHV-1 immunogen; and wherein (ii) the replacement gene is optionally under the control of a promoter; and further wherein (iii) at least one essential gene of wild-type BHV-1 is optionally mutated are provided. Vaccines compositions comprising a pharmaceutically acceptable vehicle and a bovine herpesvirus 1 (BHV-1) wherein at (i) least one non-essential gene is deleted or (ii) an essential gene is mutated are also provided. In addition, related vectors, DNA constructs, a diagnostic assay and methods for treating and preventing BHV-1 infection and other bacterial and viral pathogens of cattle are provided.

46 Claims, 21 Drawing Sheets

OTHER PUBLICATIONS

Fitzpatrick et al., "Nucleotide sequence of bovine herpesvirus type 1 glycoprotein gill, a structural model for gill as a new member of the immunoglobulin superfamily, and implications for the homologous glycoproteins of other herpesviruses" *Virology* (1989) 173:46–57.

Pachl et al., "Expression of cell–associated and secreted forms of herpes simplex virus type 1 glycoprotein gB in mammalian cells" *J. Virol.* (1987) 61(2):315–325.

van Drunen Little–van den Hurk et al., "Synthesis, cellular location, and immunogenicity of bovine herpesvirus 1 glycoproteins gI and gIII expressed by recombinant vaccinia virus" *J. Virol.* (1989) 63(5):2159–2168.

Liang et al., "Bovine herpesvirus 1 attachment to permissive cells is mediated by its major glycoproteins gI, gIII, and gIV" *J. Virol.* (1991) 65(3):1124–1132.

Liang et al., "Pseudorabies virus gIII and bovine herpesvirus 1 gIII share complementary functions" *J. Virol.* (1991) 65(10):5553–5557.

Liang et al., "An in vivo study of glycoprotein gIII–negative bovine herpesvirus 1 (BHV–1) mutant expressing β–galactosidase: evaluation of the role of gIII in virus infectivity and its use as a vector for mucosal immunization" *Virol.* (1992) 189:629–639.

Kit et al., "Bovine herpesvirus–1 (infectious bovine rhinotracheitis virus)–based viral vector which expresses foot––and –mouth disease epitopes" *Vaccine* (1991) 9:564–572.

Lawrence et al., "Bovine herpesvirus 1 recombinant expresses vesicular stomatitis virus glycoprotein G which is not transported to the cell surface" *Abstracts of the 15th International Herpes Virus Workshop* (1990) pp. 432.

Pyles et al., "The role of deoxyuridine triphosphatase in HSV–1 pathogens" *Abstracts of the 15th International Herpes Virus Workshop* (1990) pp. 164.

McGeoch et al., "Protein sequence comparisons show that the 'pseudoproteases' encoded by poxyviruses and certain retroviruses belong to the deoxyuridine triphosphatase family" *Nucl. Acids Res.* (1990) 18 (14):4105–1409.

van Zijl et al., "Live attenuated pseudorabies virus expressing envelope glycoprotein E1 of hog cholera virus protects swine against both pseudorabies and hog cholera" *J. Virol.* (1991) 65(5):2761–2765.

Babiuk et al., "Viral–bacterial synergistic interaction in respiratory disease" *Adv. Virus Res.* (1988) 35:219–249.

Husband, A.J., "Perspectives in mucosal immunity: a ruminant model" *Vet. Immunol. Immunopathol.* (1987) 17:357–365.

Karupiah et al., "Interferon γ is involved in the recovery of athymic nude mice from recombinant vaccinia virus/interleukin 2 infection" *J. Exp. Med.* (1990) 172:1495–1503.

Ramshaw et al., "Recovery of immunodeficient mice from a vaccinia virus/IL–2 recombinant infection" *Nature* (1987) 329:545–546.

Flexner et al., "Prevention of vaccinia virus infection in immunodeficient mice by vector–directed IL–2 expression" *Nature* (1987) 330:259–262.

Giavendoni et al., "Vaccinia virus recombinants expressing chimeric proteins of human immunodeficiency virus and γ interferon are attenuated for nude mice" *Proc. Natl. Acad. Sci.* (1992) 89:3409–3413.

Sambhi et al., "Local production of tumor necrosis factor encoded by recombinant vaccinia virus is effective in controlling viral replication in vivo " *Proc. Nat. Acad. Sci.* (1991) 88:4025–4029.

Carpenter et al., "The most abundant protein in bovine herpes 1 virions is a homologue of herpes simplex virus type 1 UL47" *J. Gen. Virol.* (1991) 72:3077–3084.

Lawman et al., "Generation of IL–2 dependent bovine cytotoxic T lymphocyte clones reactive against BHV–1 infected target cells: loss of genetic restriction and virus specificity" *Viral Immun.* (1987) 1(3):165.

van Drunen Little–van den Hurk et al., "characterization of the major tegument protein VP8 of bovine herpesvirus–1(BHV–1)" *Abstracts of the 16th International Herpesvirus Workshop* (1991) p. 242.

Tizard et al., *An Introduction to Veterinary Immunology* Second Edition, (1982) W.B. Saunders Company, Philadelphia, pp. 182–185.

van Drunen Little–van den Hurk et al., "Bovine herpesvirus–1 vaccines" *Immunology and Cell Biol.* (1993) 71:405–420.

van Drunen Littel–van den Hurk et al, Immunology + Cell Biology (1993) vol. 71: 405–420.

Tikoo et al, Advances in Virus Research vol. 45: 191–223 (1995).

Yancey R.J. Jr, J. Dairy Science vol. 76: 2418–2436 (1993).

Kit et al (1991) Arch Virol vol. 120: 1–17.

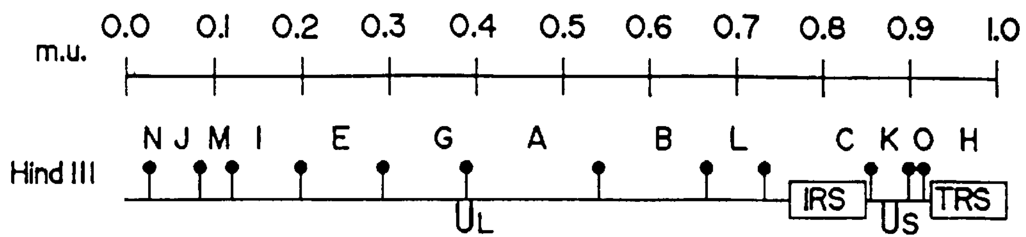
FIG. 1A
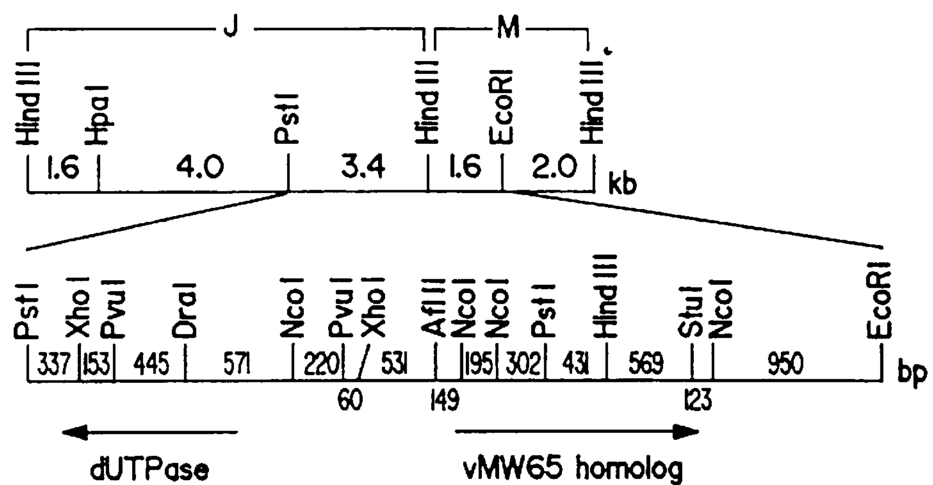
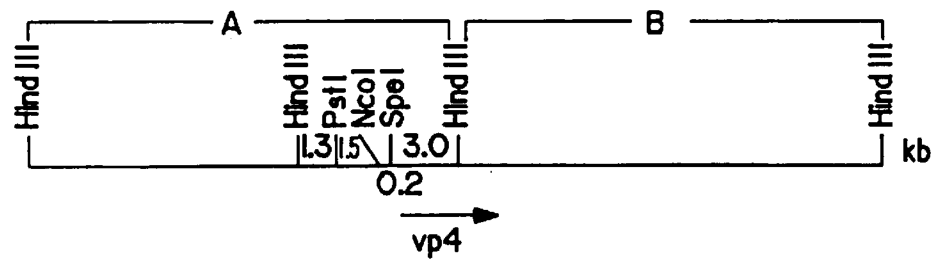
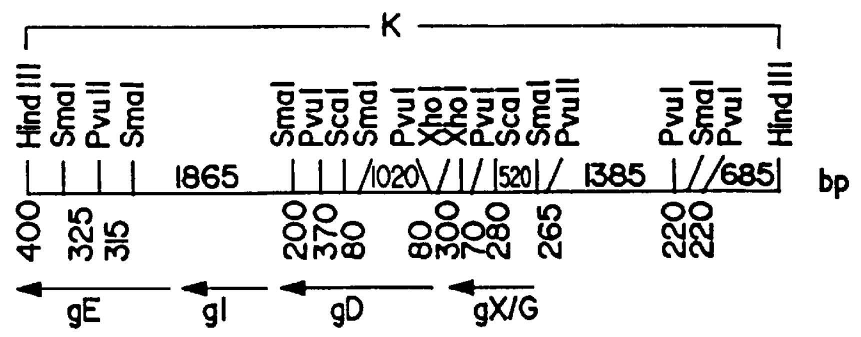
FIG. 1B

FIG.2A

```
                                                    TATA box                      Cap site
CGAGCGGCGCGCGGCTTAAGCAGCGCGCTGCTGTGCTAGTATGAAAATAAACGCTTGTTAATTAAACACACCAAGCC
          GAGTTGCGTTGTCTTTGGG ATG AGC GGG CGC ATA AAA ACC GCG GGC CGC GCG CTC GCC AGT CAG
                              Met Ser Gly Arg Ile Lys Thr Ala Gly Arg Ala Leu Ala Ser Gln

          TGC GGC GGT GCT GCG GCG GCA ACC ATG GAC CCG TAC GAC GCC ATT GAA GCG TTC GAT GAC
16        Thr Met Asp Pro Tyr Asp Ala Ile Glu Ala Phe Asp Asp Ser Leu Leu Gly Cys Gly Gly

          TCC CTG CTC GGG TCG CCG CTC GCG GCG GGG CCG CTT TAT GAC GGC CCG TCC CCC GCG CGG
36        Ala Ala Ala Ala Ser Pro Leu Ala Ala Gly Pro Leu Tyr Asp Gly Pro Ser Pro Ala Arg

          TTC GCG CTG CCG CCC CCG CGC CCG GCT CCC CTG GCC GCG TTG CTG GAG CGA ATG CAG GCC
56        Phe Ala Leu Pro Pro Pro Arg Pro Ala Pro Leu Ala Ala Leu Leu Glu Arg Met Gln Ala

          GAG CTG GGC TTC CCC GAC GGC CCC GCG CTG CTG CGG GCC ATG GAG CGG TGG AAC GAG GAC
76        Glu Leu Gly Phe Pro Asp Gly Pro Ala Leu Leu Arg Ala Met Glu Arg Trp Asn Glu Asp

          TTA TTC TCG TGT CTG CCG ACC AAC GCA GAC CTG TAC GCA GAC GCC GCG CTG CTC TCG GCA
96        Leu Phe Ser Cys Leu Pro Thr Asn Ala Asp Leu Tyr Ala Asp Ala Ala Leu Leu Ser Ala

          GAC GCA GAC GCG GTA GTG GGC GCC ATG TAC CTA GCG GTG CCT GGG GAC GCG GAG CGC TTG
116       Asp Ala Asp Ala Val Val Gly Ala Met Tyr Leu Ala Val Pro Gly Asp Ala Glu Arg Leu

          GAC TTG AAC GCG CAC GCG AAC CAG CCG CTT CCC GCA CCG CCG GCC TCG GAG GAG GGC CTC
136       Asp Leu Asn Ala His Ala Asn Gln Pro Leu Pro Ala Pro Pro Ala Ser Glu Glu Gly Leu

          CCG GAG TAT GTG GCC GGC GTA CAG GCG CAT TTT CTG GCA GAG CTG CGC GCG CGG GAA GAG
156       Pro Glu Tyr Val Ala Gly Val Gln Ala His Phe Leu Ala Glu Leu Arg Ala Arg Glu Glu

          CGG TAC GCG GGC CTG TTT TTG GGC TAC TGC CGC GCG CTG CTG CAG CAC CTG CGC GCG ACG
176       Arg Tyr Ala Gly Leu Phe Leu Gly Tyr Cys Arg Ala Leu Leu Gln His Leu Arg Ala Thr

          GCG GCG CGT GGC CGA GGC GCG GCG GGC GCG GGC GCC CAG GCA GAC CGC CTG CGG CAG CTG
196       Ala Ala Arg Gly Arg Gly Ala Ala Gly Ala Gly Ala Gln Ala Asp Arg Leu Arg Gln Leu

          GTG GCG GCG CGG TAC TAC CGC GAG GCG AGC GCG CTG GCG CGG CTG GCC TTT GCG CAT ATG
216       Val Ala Ala Arg Tyr Tyr Arg Glu Ala Ser Ala Leu Ala Arg Leu Ala Phe Ala His Met

          TAC GTG GCG ACG GCG CGC GAA GTC TCT TGG CGC CTG CAC TCC CAG CAG AGC CAG GCG CAG
236       Tyr Val Ala Thr Ala Arg Glu Val Ser Trp Arg Leu His Ser Gln Gln Ser Gln Ala Gln
```

FIG.2B

```
    GGC GTG TTC GTT TCG CTG TAC TAT GCT TGG CCG CAG CGG CGG CAG TTC ACC TGC CTG TTC
256 Gly Val Phe Val Ser Leu Tyr Tyr Ala Trp Pro Gln Arg Arg Gln Phe Thr Cys Leu Phe

    CAC CCC GTG CTG TTC AAC CAC GGC GTC GTG GCG CTG GAG GAC GGC TTC TTG GAC GCG GCG
276 His Pro Val Leu Phe Asn His Gly Val Val Ala Leu Glu Asp Gly Phe Leu Asp Ala Ala

    GAG CTG CGG CGG CTA AAC TAC CGG CGT CGG GAG CTG GGG CTG CCG CTG GTC CGC GCG GGG
296 Glu Leu Arg Arg Leu Asn Tyr Arg Arg Arg Glu Leu Gly Leu Pro Leu Val Arg Ala Gly

    CTG GTC GAG GTT GAA GTG GGG CCT CTG GTG GAG GAG CCG CCG TTT TCG GGA AGC TTG CCG
316 Leu Val Glu Val Glu Val Gly Pro Leu Val Glu Glu Pro Pro Phe Ser Gly Ser Leu Pro

    CGG GCG CTG GGC TTC CTG AAT TAC CAA GTA CGC GCG AAG ATG GGC GCG CCC GCC GAG GCC
336 Arg Ala Leu Gly Phe Leu Asn Tyr Gln Val Arg Ala Lys Met Gly Ala Pro Ala Glu Ala

    GGC GGG CGG CTG GCG CCG GAG CGG GAG CAC TCG TAC GCG CGG CCG CGC GGC GCG ATC AAC
356 Gly Gly Arg Leu Ala Pro Glu Arg Glu His Ser Tyr Ala Arg Pro Arg Gly Ala Ile Asn

    TAC GGG ACG ACT CCA GAG GCC ATG TTG CGG CCC CCG TCG CCG AGC GAA GTG CTG CCG TGC
376 Tyr Gly Thr Thr Pro Glu Ala Met Leu Arg Pro Pro Ser Pro Ser Glu Val Leu Pro Cys

    GAC CCC GCG CCA GCG GCT ACC GTG CGC GTG GCG AGC CCC GCC ACA CAT CTG GCT CAG GCG
396 Asp Pro Ala Pro Ala Ala Thr Val Arg Val Ala Ser Pro Ala Thr His Leu Ala Gln Ala

    CCT TCA GCC AAG GGC GCC GCC CCG GCC GAG TTT GCC GCC TTG GCT GGG CTT GCA AGG CCC
416 Pro Ser Ala Lys Gly Ala Ala Pro Ala Glu Phe Ala Ala Leu Ala Gly Leu Ala Arg Pro

    GGT CCG GCC CCG CTC GCG GCG GCC CCG GCC CAA GCC CCG TTC GCA GCG GCC TTG GCC TTA
436 Gly Pro Ala Pro Leu Ala Ala Ala Pro Ala Gln Ala Pro Phe Ala Ala Ala Leu Ala Leu

    GCC GAG CCC GCG GCA GCC CTG GCC CCG GCC CCG CTT GCG GCG GCC CCA GCC GAG CCC GCG
456 Ala Glu Pro Ala Ala Ala Leu Ala Pro Ala Pro Leu Ala Ala Ala Pro Ala Glu Pro Ala

    GCG GCC GTC GCC GGG CCA AGC CCG GCA AAC CCA TTC GGC GGC ACG TAT GAC GCG CTG CTG
476 Ala Ala Val Ala Gly Pro Ser Pro Ala Asn Pro Phe Gly Gly Thr Tyr Asp Ala Leu Leu

    GGG GAC CGC CTC AAC CAG CTG CTG GAC TTC TAA GGGCGGGCGGGCAGTGGCGCTTTCGACCCGGCGCG
496 Gly Asp Arg Leu Asn Gln Leu Leu Asp Phe End
                                                                    TATA box
    TGGCGTTTGCGAGGCCTCCCTCTGGCGTAAGGCCTCGTGGCGCCGCCCTGCGGGCGGCGCGAGCGTATAAAAGCCACTT
    GGGTCTACACGGGATTTAGTTTTCGCGCCCGCGGCTTTCTAGGCGCCCTTAGACCCCATG——UL47(vp8)——
```

HindIII
ScaI
HindIII
PvuII
SmaI
PvuI
PvuII
SmaI
ScaI
PvuI
XhoI
XhoI
PvuI
SmaI
ScaI
PvuI
SmaI
SmaI
PvuII
SmaI
HindIII
HdO
HdK
gI
gE
1780
NoTI
lacZ
pC
PA

| Virus | Motif (a.a.) | | Oligonucleotides |
|---|---|---|---|
| | | | HindIII |
| HSV1 | 3 | (IDSGYRG) | 1. 5'-CAAAGCTT ATN GAQ TCW GGW TAQ CGW GG |
| HSV1 | 3 | (IDSGYRG) | 2. 5'-CAAAGCTT ATN GAQ TCW GGW TAQ AGX GG |
| VZV | 3 | (IDAGTRG) | 3. 5'-CAAAGCTT ATN GAQ GCW GGW TAQ CGW GG |
| | | | EcoRI |
| HSV1 | 1 | (EDAGFDI) | 4. 3'-CT QCT XCG WCC WAA XCT XAT CTTAAGAC |
| VZV | 1 | (EDAGFDI) | 5. 3'-CT QCT XCG WCC WAT XCT XAT CTTAAGAC |

Q, CT; X, GA; Z, CA; N, CTA; W, GCTA

FIG. 5A

```
                                 XhoI
1                              CCTCGAGCGGCGGGCCGGCGCGGCGGCGGGCGCAGCTACGGTCGTC
46    CCCGCGGCTGCGGCTCGATCGCGGCCGCGGGCGGCGGGCTGGACGGCTGCAGCGCTGGCG
106   CACGCACGGACGCTAGCGCGCCGCCCGCTCGGCTCGGGTCCGCTCGTCGCGGCGCGCAGC
166   TCTTCGTATACGTGGTCATCCGAGCCGGACTCGTAGTCATAGAGGCTGTTTTCTCGCACC
                                                                NcoI
226   CAAAGGTCGCTGTACTCGTAATCGTCCTCGTCTTCGGAGGGCCTGTGGAACCGGGCCATG
286   GCAAGCGAGTCGGCGGGCCGGCGGGCGTGCAGCTCAAAGCGGGTCGGGCCGAGTGCGAAA
                                 tata box
346   AAGGCAGCGGTCGCCGGGACCGCGAGCTTTATATACAAGTTACTCCGCAGCGTTGCGGTC
406   AATCAGCCCCGCCCCCGCGACTCCTTTTTATTGGGCCCGCTGGCGCCCATGAGCCTAAAG
466   CAAAGCCCGTACGCGTACAGGGCCACGGCGACCATTACCGCGGTCAGGGCCACGTAAAAA
526   ACAACCAGGGCCTGCGGTGGCTCCGAGAGCGGCACCCCGCGCGCGTAGCAGCCTGCGCTC
586   CAAAAGTCCATTGCCCCCTCGCGCCGCATCGCGTCTAGCAGGGGGTCGCGGCCGCGCACG

646   ATG GCA AAC AGC GCG GCG GCC ACA ACC GCA ACG ATG AGC GGC GAC CGC GGC
1      M   A   N   S   A   A   A   T   T   A   T   M   S   G   D   R   G

697   ATC CTC GTC GTA GAG CTC AAC GCG GAG GCG GCC CCC TGG CGG TTG GAA AGC
18     I   L   V   V   E   L   N   A   E   A   A   P   W   R   L   E   S

748   TGC TGT GAG CCC GAC TCG CTG GCG CTC TGG GGC CCA ATT GCG CCA GCA GCA
35     C   C   E   P   D   S   L   A   L   W   G   P   I   A   P   A   A

799   AAG CGA GAT GAA ACA GCC CCG TCG GGA TCT CTC CTT TAT AGC CGG CTG ATT
52     K   R   D   E   T   A   P   S   G   S   L   L   Y   S   R   L   I
           DraI
850   AAT TTA AAC ATG AAG GCG GCC GCG CCC GGC GGA TAT GCC ATT ATA ATG TCG
69     N   L   N   M   K   A   A   A   P   G   G   Y   A   I   I   M   S

901   CAA ATG CGC TCG GGT GAC ACA CAC ATG CCC CGC CCA CCA GCC GTG GCC GTC
86     Q   M   R   S   G   D   T   H   M   P   R   P   P   A   V   A   V

952   GGC ATC GTC GAC TCG GGC TAC TCG GGG ATC TTG CGC GCC ATC GTC TGG GCG
103    G   I   V   D   S   G   Y   S   G   I   L   R   A   I   V   W   A

1003  CCC GAG TCC GCA GCG GCC GCT CCC CCG GCG GGG CTT GCG CTG CGG CTG ACG
120    P   E   S   A   A   A   A   P   P   A   G   L   A   L   R   L   T

1054  CTC GCG CGG CTA ACC ACC ACG CTG CCT CGC CTC ATC GCC GTC GAC GAC GAC
137    L   A   R   L   T   T   T   L   P   R   L   I   A   V   D   D   D
```

FIG.5B

```
1105 GCA AAC GCC GGG ACA GAG GCG GGC GTC GAA GTG CCC TTC TTT GCC ACG TTC
154   A   N   A   G   T   E   A   G   V   E   V   P   F   F   A   T   F

1156 GCC CCC AAA CGC GAC GAG GAC GCC GGG TAC GAT ATT GCC ATG CCA TAC ACG
171   A   P   K   R   D   E   D   A   G   Y   D   I   A   M   P   Y   T

1207 GCC GTC TTG GCA CCC GGG GAA AAT TTA CAC GTG CGG CTG CCC GTA GCC TAC
188   A   V   L   A   P   G   E   N   L   H   V   R   L   P   V   A   Y

1258 GCG GCA GAC GCC CAC GCT GCC GCG CCC TAC GTG TTT GGT CGA TCG TCC TGC
205   A   A   D   A   H   A   A   A   P   Y   V   F   G   R   S   S   C

1309 AAC CTT CGG GGG CTG ATC GTC CTG CCG ACA GCC TGG CCC CCC GGG GAG CCC
222   N   L   R   G   L   I   V   L   P   T   A   W   P   P   G   E   P

1360 TGC CGC TTT GTC TTG CGA AAC GTC ACG CAG GAA CCG CTC GTT GCT GCC GCA
239   C   R   F   V   L   R   N   V   T   Q   E   P   L   V   A   A   A
                                                          XhoI
1411 GGC CAG CGC GTG GCG CAG CTG CTT CTG CTG GCA CGG CGC CTC GAG TGG CTT
256   G   Q   R   V   A   Q   L   L   L   L   A   R   R   L   E   W   L

1462 CCG TCC GGC CTC AAC GAC CGC GAG CCC TTC CCA ACT AGC CCT CGC GCA GCA
273   P   S   G   L   N   D   R   E   P   F   P   T   S   P   R   A   A

1513 CCG CCC GCC CCT GGG GCC CCG CGC CTG CGC TGG CGC CGC GTC GCC GAT CTC
290   P   P   A   P   G   A   P   R   L   R   W   R   R   V   A   D   L

1564 GCC GCG GCG GTG CCC CCC TCT GCG CGC GGG CCG CGC GGC TTT GGG TCC ACC
307   A   A   A   V   P   P   S   A   R   G   P   R   G   F   G   S   T

1615 GGG CTG TAA AACAAAGCACATTAAAGTACACCGACTCCACCACACACGTGTTTTGCGTAT
324   G   L   *

1675 ACTTATTTTGCTTTTATTGCACCGGGCTACGCCGCAAGCTGCAAAACGGCGGGGGAAGAA
1735 GCGGCGGCCGCCGCGCGCCCCGCGCGGCTAGGTGGTTTTGTGGCGGCCGCCTCTGCAGGC
1795 GCCACCGGCGGTGCCGGAGACACGGCGACCGGCGCCGAGGCGGCCGGCTGCCGCGG
```

FIG. 6

```
-901               ACGGCCACGGCTGGTGGGCGGGGCATGTGTGTGTCACCCGAGCGCATTTG
          tata box                                 DraI
-951    CGACATTTATAATGGCATATCCGCCGGGCGCGGCCGCCTTCATGTTTAAATTAATCAGCCG
-1011   GCTATAAAGGAGAGATCCCGACGGGGCTGTTTCATCTCGCTTTGCTGCTGGCGCAATTGG
-1071   GCCCCAGAGCGCCAGCGAGTCGGGCTCACAGCAGCTTTCCAACCGCCAGGGGGCCGCCTC
-1131   CGCGTTGAGCTCTACGACGA GG ATG CCG CGG TCG CCG CTC ATC GTT GCG GTT GTG
1                               M   P   R   S   P   L   I   V   A   V   V
               dUPTase ORF
        <-------------------------

-1186   GCC GCC GCG CTG TTT GCC ATC GTG CGC GGC CGC GAC CCC CTG CTA GAC GCG
12       A   A   A   L   F   A   I   V   R   G   R   D   P   L   L   D   A

-1237   ATG CGG CGC GAG GGG GCA ATG GAC TTT TGG AGC GCA GGC TGC TAC GCG CGC
29       M   R   R   E   G   A   M   D   F   W   S   A   G   C   Y   A   R

-1288   GGG GTG CCG CTC TCG GAG CCA CCG CAG GCC CTG GTT GTT TTT TAC GTG GCC
46       G   V   P   L   S   E   P   P   Q   A   L   V   V   F   Y   V   A

-1339   CTG ACC GCG GTA ATG GTC GCC GTG GCC CTG TAC GCG TAC GGG CTT TGC TTT
63       L   T   A   V   M   V   A   V   A   L   Y   A   Y   G   L   C   F

-1390   AGG CTC ATG GGC GCC AGC GGG CCC AAT AAA AAG GAG TCG CGG GGG CGG GGC
80       R   L   M   G   A   S   G   P   N   K   K   E   S   R   G   R   G

-1441   TGATTGACCGCAACGCTGCGGAGTAACTTGTATATAAAGCTCGCGGTCCCGGCGACCGCT
-1501   GCCTTTTTCGCACTCGGCCCGACCCGCTTTGAGCTGCACGCCCGCCGGCCCGCCGACTCG
             NcoI
-1561   CTTGCCATGGCCCGGTTCCACAGGCCCTCCGAAGACGAGG
```

FIG. 7

```
GGCCGGGCTG GGCGCGTGCG TACACGGCGG ATCTCGTTTG TGACGTTATC

GGGTTTTTCG CGCCCCGGGC GTGGATGCGC GTGTGCCTGG GGGGCACGTA

GTATAAAACG AGCGGGGGGC CGCGGGCGCA CTGCGCGCGC CGCCCCACAC

        M   D   R   Q   S   E   P   P   R   A   P   A   Y   T
CGCGCC ATG GAC CGC CAG AGC GAG CCT CCG CGC GCG CCC GCC TAC ACG
    NcoI

G   G   L   V   S   G   L   V   L   S   N   I   E   V   A   C
GGC GGG CTG GTC TCC GGT CTT GTG CTG TCG AAC ATC GAA GTG GCC TGC

H   R   A   L   F   S   F   F   Q   Q   V   R   S   D   D   N
CAC CGC GCG CTG TTC AGC TTT TTC CAG CAG GTG CGA TCG GAC GAC AAC

G   L   Y   A   A   A   F   D   R   L   F   P   T   Y   C   N
GGC CTG TAC GCG GCC GCC TTT GAC CGC CTC TTG GGC ACG TAC TGC AAC

T   L
ACG CTG A
```

FIG. 11A dUTPase

1 CGGTTGTGGCCGCCGCGCTGTTTGCCATCGTGCGCGGCCGCGACCCCCTGCTAGACGCGA

61 TGCGGCGCGAGGGGGCAATGGACTTTTGGAGCGCAGGCTGCTACGCGCGCGGGGTGCCGC

121 TCTCGGAGCCACCGCAGGCCCTGGTTGTTTTTTACGTGGCCCTGACCGCGGTAATGGTCG

181 CCGTGGCCCTGTACGCGTACGGGCTTTGCTTTAGGCTCATGGGCGCCAGCGGGCCCAATA

UL49.5

G-C TATA box

241 AAAAGGAGTCGCGGGGGCGGGGCTGATTGACCGCAACGCTGCGGAGTAACTTGTATATAA

Cap site

301 AGCTCGCGGTCCCGGCGACCGCTGCCTTTTTCGCACTCGGCCCGACCCGCTTTGAGCTGC

361 ACGCCCGCCGGCCCGCCGACTCGCTTGCC ATG GCC CGG TTC CAC AGG CCC TCC GAA GAC
M A R F H R P S E D

420 GAG GAC GAT TAC GAG TAC AGC GAC CTT TGG GTG CGA GAA AAC AGC CTC TAT
E D D Y E Y S D L W V R E N S L Y

471 GAC TAC GAG TCC GGC TCG GAT GAC CAC GTA TAC GAA GAG CTG CGC GCC GCG
D Y E S G S D D H V Y E E L R A A

522 ACG AGC GGA CCC GAG CCG AGC GGG CGG CGC GCT AGC GTC CGT GCG TGC GCC
T S G P E P S G R R A S V R A C A

573 AGC GCT GCA GCC GTC CAG CCC GCC GCC CGC GGC CGC GAT CGA GCC GCA GCC
S A A A V Q P A A R G R D R A A A

624 GCG GGG ACG ACC GTA GCT GCG CCC GCC GCC GCG CCG GCC CGC CGC TCG AGC
A G T T V A A P A A A P A R R S S

675 AGC CGG GCG TCC TCG CGC CCG CCG CGA GCT GCC GCC GAC CCG CCC GTC CTC
S R A S S R P P R A A A D P P V L

726 CGG CCA GCC ACG CGC GGG TCC TCC GGC GGC GCC GGG GCA GTC GCC GTC GGT
R P A T R G S S G G A G A V A V G

777 CCA CCT CGA CCT CGC GCG CCC CCC GGT GCT AAT GCT GTT GCG TCT GGC CGG
P P R P R A P P G A N A V A S G R

FIG.11B

```
828  CCG CTG GCG TTC AGC GCG GCT CCG AAA ACG CCC AAG GCG CCC TGG TGT GGA
      P   L   A   F   S   A   A   P   K   T   P   K   A   P   W   C   G

879  CCG ACG CAC GCC TAC AAC CGA ACG ATC TTT TGC GAG GCC GTC GCG CTC GTG
      P   T   H   A   Y   N   R   T   I   F   C   E   A   V   A   L   V

930  GCC GCC GAG TAC GCC CGG CAG GCG GCT GCC AGC GTC TGG GAC TCG GAC CCC
      A   A   E   Y   A   R   Q   A   A   A   S   V   W   D   S   D   P

981  CCA AAG AGC AAC GAG CGA TTG GAT CGC ATG TTG AAG TCG GCG GCA ATT CGC
      P   K   S   N   E   R   L   D   R   M   L   K   S   A   A   I   R

1032 ATC CTC GTG TGC GAG GGC TCC GGG CTT CTC GCC GCC GCG AAC GAC ATC TTG
      I   L   V   C   E   G   S   G   L   L   A   A   A   N   D   I   L

1083 GCC GCG CGG GCC CAG CGC CCC GCC GCG CGC GGG AGC ACA AGC GGC GGG GAA
      A   A   R   A   Q   R   P   A   A   R   G   S   T   S   G   G   E

1134 AGC CGC CTT CGC GGC GAG CGG GCC CGG CCG TAGCGCGAGCGGGAGGGCTTTTTCGACGC
      S   R   L   R   G   E   R   A   R   P   *
                                           Poly A signal
1193 GCGCGGCTTAAGCAGCGCGCTGCTGTGCTAGTATGAAAATAAACGCTTGTTAATTAAACA

1253 CACCAAGCCGAGTTGCGTTGTCTTTGGGATGAGCGGGCGCATAAAAACCGCGGGCCGCGC
                                            UL48 →
1313 GCTCGCCAGTCAGTGCGGCGGTGCTGCGGCGGCAACCATGGACCCGTACGACGCCATTGA

1373 AGCGTTCGATGACTCCCTGCTCGGGTCGCCGCTCGCGGCGGGGCCGCTTTATGACGGCCC

1433 GTCCCCCGCGCGGTTCGCGCTGCCGCCCCCGCGCCCGGCTCCCCTGGCCGCGTTGCTGGA

1493 GCGAATG
```

```
BHV1 MARFHRPSEDEDDY---EYSDLWVRENSLY--DY---ES-------GSDD    35
VZV  MA----SSDGDRLC---RSNAVRRKTTPSYSGQY---RTARRSVVVGPPD    40
HSV1 MTSRRSVKSGPREVPRDEYEDLYYTPSSGMASPDSPPDTSRRGALQTRSR    50

BHV1 HV-------YEELRAA---TSGPEPSGRRASVRACASAAAVQPAARGRDR    75
VZV  DS-------DDSLGYI---TTVGADSPSPVYADLYFEHKNTTPRVHQPND    80
HSV1 QRGEVRFVQYDESDYALYGGSSSEDDEHPEVPRTRRPVSGAVLSGPGPAR   100

BHV1 AAAAGTTVAAPAAAPA--RRSSSRASSRPPRAAADP-PVLRPATRGSSGG   122
VZV  SSGSEDDFEDIDEVVAAFREARLRHELVEDAVYENPLSVEKPSRSFTKNA   130
HSV1 APPPPAGSGGAGRTPTTAPRAPRTQRVATKAPAAPAAETTRGRKSAQPES   150

BHV1 AGAVAVGPPRPRAPPGANAVASGRPLAFSAAPKTPKAPWCGPTHAYNRTI   172
VZV  AVKPKLEDSPKRAPPGAGAIASGRPISFSTAPKTATSSWCGPTPSYNKRV   180
HSV1 AALPDAPASTAPTRSKTPAQGLARKLHFSTAPPNPDAPWTPRVAGFNKRV   200

BHV1 FCEAVALVAAEYARQAAASVWDSDPPKSNERLDRMLKSAAIRILVCEGSG   222
VZV  FCEAVRRVAAMQAQKAAEAAWNSNPPRNNAELDRLLTGAVIRITVHEGLN   230
HSV1 FCAAVGRLAAMHARMAAVQLWDMSRPRTDEDLNELLGITTIRVTVCEGKN   250

BHV1 LLAAANDI----------------------------LAARAQRPAARGST   244
VZV  LIQAANEADLGEGASVSKRGHNRKTGDLQGGMGNEPMYAQVRKPKSRTDT   280
HSV1 LLQRANE-----------------------LVNPDVVQDVDAATATRGR   276

BHV1 SGGE-----SRLRGER---ARP---    258
VZV  QTTGRITNRSRARSASRTDTRK---    302
HSV1 SAASRPTERPRAPARSASRPRRPVE    301
```

FIG. 12

RECOMBINANT BOVINE HERPESVIRUS TYPE 1 VACCINES

CROSS-REFERENCE TO RELATED APPLICATIONS

This is a continuation-in-part of U.S. Ser. No. 08/051,448, filed Apr. 19, 1993 now abandoned.

TECHNICAL FIELD

The present invention relates generally to the prevention of disease in cattle. More particularly, the instant invention is directed to the production and use of attenuated and marked bovine herpesvirus 1 (BHV-1) vaccines that protect cattle from BHV-1 infection. The present invention is further directed towards the use of modified BHV-1 as a vector for the expression of other bacterial or viral genes and the use of these vaccines for the protection of cattle from disease.

BACKGROUND

Bovine herpesvirus type 1 is an economically significant pathogen of cattle. BHV-1, which is also known as infectious bovine rhinotracheitis virus, causes severe respiratory infections, conjunctivitis, vulvovaginitis, abortions, encephalitis, and generalized systemic infections. If an animal recovers from a primary infection, the virus remains in the host in a latent state. Reactivation of the virus can be provoked by certain endogenous or exogenous physical modifications in the animal, or experimentally by treatment of the animal with glucocorticoids such as dexamethasone.

In an effort to control BHV-1 infections, conventional killed-virus and attenuated live-virus vaccines have been developed. Current modified live virus vaccines may cause immunosuppression. No recombinant forms of BHV-1, specifically attenuated by genetic engineering are currently licensed for use is cattle. While currently available vaccines appear to induce some level of protection in cattle, the level of immunity is well below that necessary to afford complete or near-complete protection. For example, the present vaccines do not always prevent the establishment of a latent infection by a virulent field strain of BHV-1. See, e.g., Gerber et al. (1978) Am. *J. Vet. Res.* 39:753–760; Jericho et al. (1983) *Can. J. Com. Med.* 47:133–139; Pastoret et al. (1980) *Infect. Immun.* 29:483–488.

Babiuk et al. (1987) *Virology* 159:57–66 relates to the purification of gI, gIII and gIV from virus-infected cell lysates, effective subunit vaccines and the protection of cattle from disease. This reference also discloses that gI of BHV-1 corresponds to gB of herpes simplex virus (HSV); gIII corresponds to gC; and gIV corresponds to gD. Purified gI, gIII and gIV have been shown to induce high levels of antibody in cattle which could neutralize virus and participate in antibody-dependent cell cytotoxicity of BHV-1 cells. The purified glycoproteins were also shown to protect cattle from disease. Babiuk et al. (1987) *Virology* 159:57–66. van Drunen Littel-van den Hurk et al. (1990) *Vaccine* 8:358–368 confirmed the protectivity of gI, gIII and gIV and studied the epitope specificity of the immune response to the glycoprotein vaccines. Hughes et al. (1988) *Arch. Virol.* 103:47–60 identified three neutralizing antigenic domains on gIV.

Mayfield et al. (1983) *J. Virol.* 47:259–264 discloses the cloning of a BHV-1 strain and a restriction endonuclease map. Fitzpatrick et al. (1989) *Virology* 173:46–57, describe the nucleotide sequence of gIII. Pachl et al. (1987) *J. Virol.* 61:315–325 describe the recombinant expression of a glycoprotein from the human pathogen HSV-1. van Drunen Littel-van den Hurk et al. (1989) *J. Virol.* 63:2159–2168 disclose the expression of gI and GIII in a vaccinia virus vector. The recombinant vectors elicited a neutralizing antibody response in cattle immunized with the same.

Liang et al. (1991a) *J. Virol.* 65(3):1124–1132 report that BHV-1 attachment to permissive cells is mediated by its major glycoproteins gI, gIII and gIV, and Liang et al. (1991b) *J. Virol.* 65(10):5553–5557 report that pseudorabies virus gIII and BHV-1 gIII share complementary functions.

Liang et al. (1992) *Virol.* 189:629–639 describe a glycoprotein $gIII^{-}$BHV-1 mutant expressing β-galactosidase, the role of gIII in virus infectivity and its use as a vector for mucosal immunization.

Kit et al. (1991) *Vaccine*, 9:564–572 report the expression of foot and mouth disease epitopes via a BHV-1 $gIII^{-}$based viral vector in which the signal sequence was deleted. Lawrence et al. (1990) Abstracts of the 15th International Herpes Virus Workshop, p. 432, disclose a BHV-1 recombinant expressed vesicular stomatitis virus glycoprotein G which is not transported to the cell surface.

Pyles et al. (1990) Abstracts of the 15th International Herpes Virus Workshop, p. 164, disclose the role of deoxyuridine triphosphatase in HSV-1 pathogenesis. McGeoch et al. (1990) *Nucl. Acid Res.* 18(14):4105–4109 report protein sequence comparisons which show that pseudoproteases encoded by poxviruses and certain retroviruses belong to the deoxyuridine triphosphatase family.

van Zijl et al. (1991) *J. Virol.* 65(5):2761–2765 describe the expression of hog cholera virus envelope glycoprotein E1 by an attenuated live pseudorabies virus which afforded swine protection against both pseudorabies and hog cholera.

Cattle are subject to numerous other viral, bacterial, fungal, and parasitic infections of the respiratory, enteric, and genital tracts (Babiuk et al. (1988) *Adv. Virus Res.*, 35:219–249) for which vaccines either do not exist or do not adequately protect against infection. A common characteristic of non-protective vaccines is their failure to stimulate the development of mucosal immunity. The lack of stimulation may be due to a failure to specifically direct antigens towards the functionally- and anatomically-distinct "common mucosal immune system" (Husband, A. J. (1987) *Vet Immunol. Immunopathol.*, 17:357–365) and/or the use of inappropriate adjuvants which fail to specifically stimulate cells of the common mucosal immune system.

Karupiah et al. (November 1990) *J. Exp. Med.* 172:1495–1503 report that gamma-interferon is involved in the recovery of athymic nude mice from treatment with recombinant vaccinia virus encoding murine interleukin-2 (IL-2). Ramshaw et al. (1987) *Nature* 329:545–546 disclose the recovery of immunodeficient mice from the same treatment. Flexner et al. (1987) *Nature* 330:259–262 disclose the prevention of vaccinia virus infection in immunodeficient mice by vector-directed IL-2 expression. Giavendon et al. (1992) *Proc. Natl. Acad. Sci. USA* 89:3409–3413 report that vaccinia virus recombinants that express chimeric proteins comprising human immunodeficiency virus peptide and gamma-interferon are attenuated for nude mice.

Sambhi et al. (1991) *Proc. Natl. Acad. Sci. USA* 88:4025–4029 report that the local production of tumor necrosis factor encoded by recombinant vaccinia virus is effective in controlling viral replication in vivo.

A new generation of natural adjuvants have been developed by cloning and expression of the endogenous cytokines which normally regulate the immune responses of cattle. It has been shown that several of these compounds, when administered in combination with vaccines, may have immuno-stimulating activity. No reports have yet described their possible effects on the common mucosal immune system of cattle. Moreover, there have been no reports that describe engineering of recombinant bovine viruses to produce immunomodulatory cytokines during the natural course of an infection with such a recombinant virus.

SUMMARY OF THE INVENTION

It is therefore an object of the present invention to provide vaccine compositions comprising mutant live-attenuated BHV-1 and a pharmaceutically acceptable vehicle that can be used to simultaneously immunize cattle against infection with wild-type BHV-1. Another object of the present invention is to provide a BHV-1 vector containing at least one functional gene from a bacterial or viral pathogen other than BHV-1 and/or a cytokine gene optionally under the control of strong promoters normally associated with the highly expressed BHV-1 protein coding genes.

Yet another object of the present invention is to provide recombinant vectors comprising DNA coding sequences wherein at least one non-essential BHV-1 gene is deleted and optionally replaced by a heterologous coding sequence encoding a foreign gene optionally under the control of a strong promoter.

A further object of the present invention is to provide DNA constructs comprising expression cassettes comprised of DNA sequences encoding promoters, heterologous coding sequences and control sequences.

Another object of the present invention is to provide a vaccine composition comprising a pharmaceutically acceptable vehicle and a mutant BHV-1 virus wherein at least one essential BHV-1 gene is mutated.

Yet a further object of the present invention is to provide an immunoassay for determining the immune status of a bovine subject for BHV-1 comprising the steps of: (i) reacting a sample of said subject with reagents comprising gene products encoded by a deleted non-essential BHV-1 gene selected from the group consisting of gE, gX, gi, and dUTPase and with reagents comprising wild-type BHV-1 gene products; and (ii) distinguishing a subject immunized with the vaccine composition of claim 1, from a subject exposed to wild-type BHV-1 in the field.

Still another object of the present invention is to provide methods of treating or preventing BHV-1 infection in cattle.

In achieving these objects, there has been provided, in accordance with one aspect of the present invention, a vaccine composition comprising: (a) a pharmaceutically acceptable vehicle; and (b) a mutant bovine herpesvirus 1 (BHV-1) wherein (i) at least one non-essential gene of wild-type BHV-1 is deleted and optionally replaced with a gene selected from the group consisting of a foreign gene, a BHV-1 gene encoding a BHV-1 immunogen and a mutant analog of a gene encoding a BHV-1 immunogen; and wherein (ii) the replacement gene is optionally under the control of a strong promoter; and further wherein (iii) at least one essential gene of wild-type BHV-1 is optionally mutated.

Non-essential BHV-1 structural genes include those encoding a glycoprotein selected from the group consisting of gE, gX, gi or the like. Genes that encode products that regulate nucleic acid metabolism include genes encoding dUTPase and thymidine kinase (TK). Genes that encode products that regulate viral gene transcription include but are not limited to genes encoding $V_{MW65}$. Essential genes include genes encoding capsid protein such as VP4 and tegument such as VP8 and $V_{MW65}$.

In accordance with another aspect of the present invention, nucleotide sequences encoding a protein promoter substantially homologous and functionally equivalent to a promoter of a BHV-1 structural gene such as VP4, VP8, $V_{MW65}$, gE, gX, gi, gI, gIV, or the like are provided.

In accordance with a further aspect of the present invention, DNA constructs are provided that comprise an expression cassette comprised of: (a) a DNA coding sequence for a polypeptide containing at least one antigenic determinant of a mutant analog of BHV-1 protein; and (b) control sequences operably linked to the DNA sequence whereby the coding sequence can be transcribed and translated in a host cell, and optionally at least one of the control sequences is heterologous to the coding sequence.

In accordance with still a further aspect of the present invention, recombinant vectors are provided which comprise a DNA coding sequence wherein at least one non-essential gene of BHV-1 is deleted and optionally replaced by a heterologous coding sequence encoding a foreign gene. The foreign gene can be under the control of an endogenous BHV-1 promoter such as a strong promoter normally associated with a structural gene encoding a BHV-1 protein such as VP4, VP8, gI, gIII, gIV and the like or an exogenous promoter such as the strong promoters normally associated with the bovine heat shock 70A gene, immediate early human cytomegalovirus gene or promoter responsive to the bacteriophage T7 RNA polymerase.

In accordance with yet a further aspect of the present invention, isolated nucleotide sequences encoding strong promoters normally associated with a BHV-1 protein coding genes are provided. Examples of such strong promoters include the strong promoters normally associated with the structural coding genes encoding BHV1 proteins such as VP4, VP8, gI, gIII, gIV and the like.

In accordance with still another aspect of the present invention, DNA constructs are provided which comprise an expression cassette comprised of (a) a DNA sequence encoding a strong promoter operably linked to a heterologous coding sequence and (b) a control sequence operably linked to the heterologous coding sequence whereby the coding sequence can be transcribed and translated in a host.

In accordance with another aspect of the present invention, vaccine compositions are provided wherein at least one non-essential BHV-1 gene is deleted.

In accordance with yet another aspect of the present invention, an immunoassay is provided for determining the absence, presence and/or concentration of antibodies directed against BHV-1 in a fluid sample such as bovine blood wherein a reagent comprising the gene product of a deleted non-essential BHV-1 is employed. Such an immunoassay can be used to determine the immune status of cattle immunized with a vaccine composition within the present invention and to distinguish animals producing antibodies directed against such a vaccine from animals producing antibodies directed against a wild-type strain of BHV1.

In accordance with yet a further aspect of the present invention, methods of treating or preventing BHV-1 infection in cattle are provided which comprise administering to the bovine host a therapeutically effective amount of a vaccine composition described above.

Other objects, features and advantages of the present invention will become apparent to those skilled in the art from the following detailed disclosure.

BRIEF DESCRIPTION OF THE FIGURES

FIG. 1A is the Genomic Map of BHV-1 Cooper strain and FIG. 1B shows the map location of the identified BHV-1 genes. In the BHV-1 genomic map, the vertical vertical lines designate HindIII restriction endonuclease sites (Mayfield et al. (1983) *J. Virology* 47:259–264). $U_L$ and $U_S$ are the "unique long" and "unique short" regions of the genome.

FIG. 2 (SEQ ID NO:1 and SEQ ID NO:2) is the DNA sequence and the deduced amino acid sequence of the $V_{MW65}$ gene homolog of BHV-1.

Figure 3A:
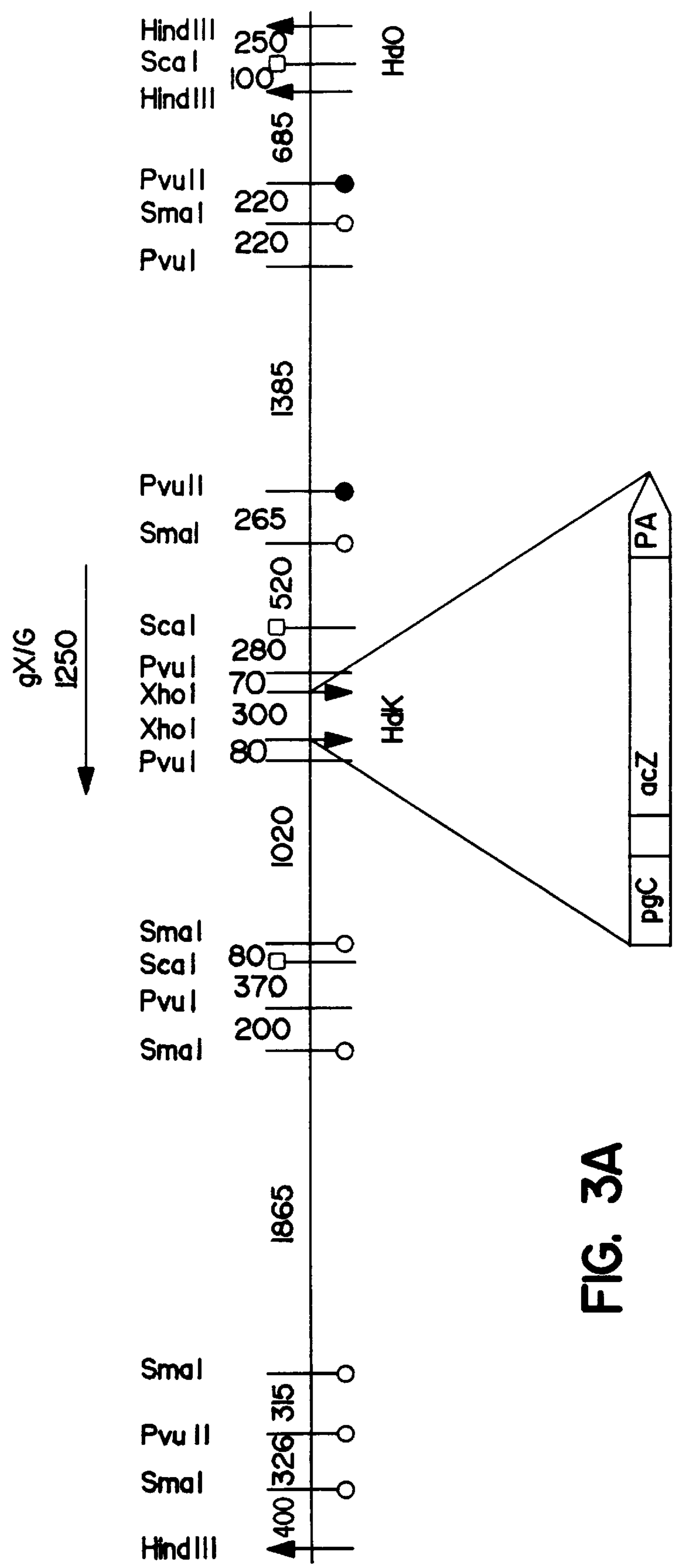

FIG. 3A is a map of the gX/G (gX) gene insertion vector. A unique 300 bp Xho I subfragment was excised from the HindIII K fragment and replaced with a lac Z gene expression cassette (spear). pgC represents the BHV-1 gC (gIII) gene promoter. lac Z represents the *E. coli* lac Z gene coding sequence, beginning with the codon for the tenth amino acid of beta-galactosidase. PA represents an SV40 polyadenylation signal. The substituted HindIII K fragment was inserted at the HindIII restriction endonuclease site of pBR322.

Figure 3B:
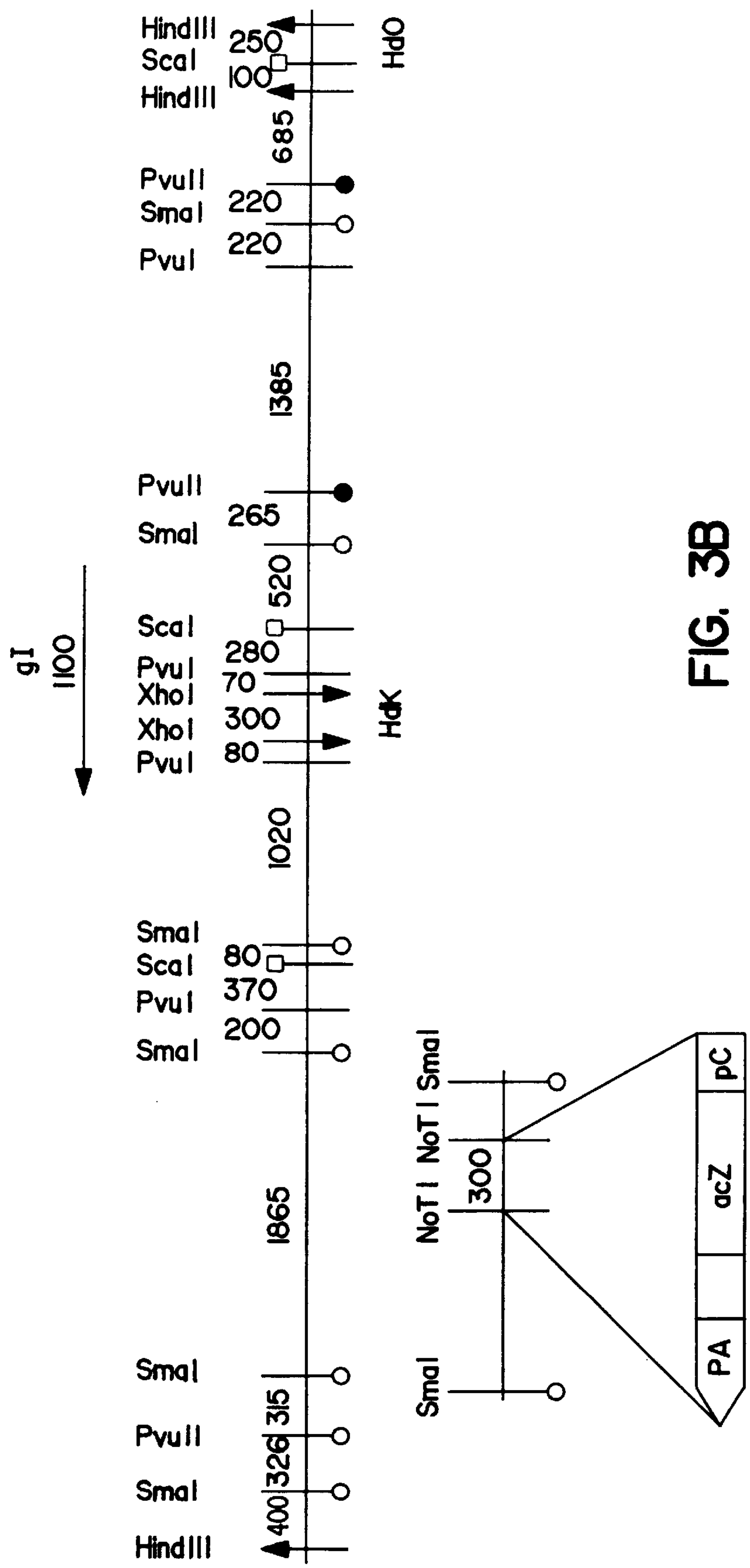

FIG. 3B is a map of the gi gene insertion vector. The lac Z gene cassette described in FIG. 3A was inserted at the unique Not I sites present in the 1865 bp Sma I subclone of the HindIII K fragment. Thus, the lac Z cassette replaced a 300 bp Not I subfragment within the Sma I subclone. The substituted Sma I subfragment was cloned into the polylinker 26 backbone.

Figure 3C:
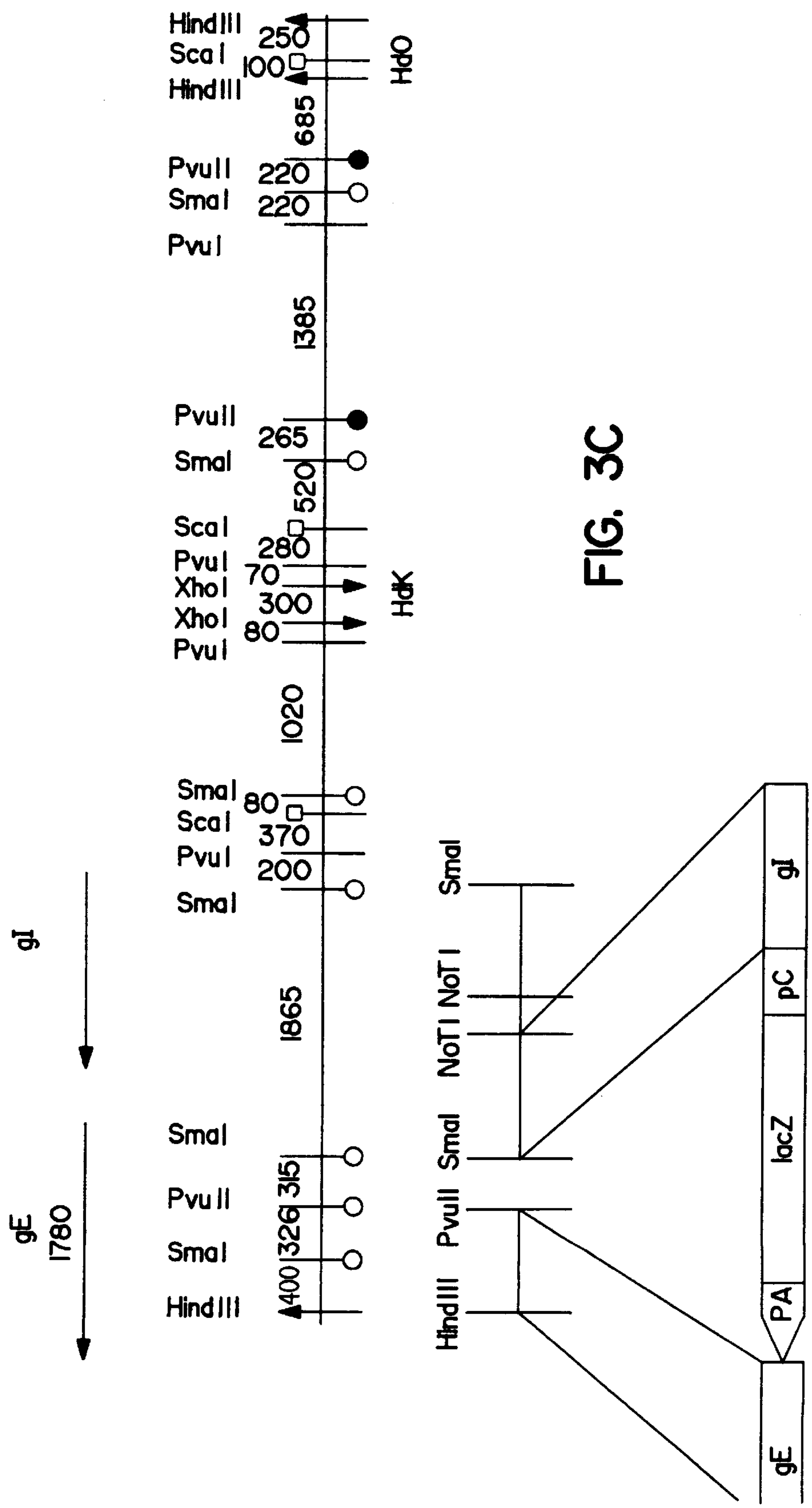

FIG. 3C is a map of the gE insertion vector. The lac Z gene cassette was flanked at its 3' end by a 775 bp HindIII-PvuII fragment isolated from the extreme left-hand end of the HindIII K fragment, and its 5' end by the 700 bp Sma I-Not I subfragment containing the 5' end o the gi gene. This same Sma I-Not I subfragment was used at the 3' end of the lac Z cassette in constructing the gi gene insertion vector (FIG. 3B). The insertion cassette was cloned into the polylinker 26 backbone.

Figures 4A, 4B:
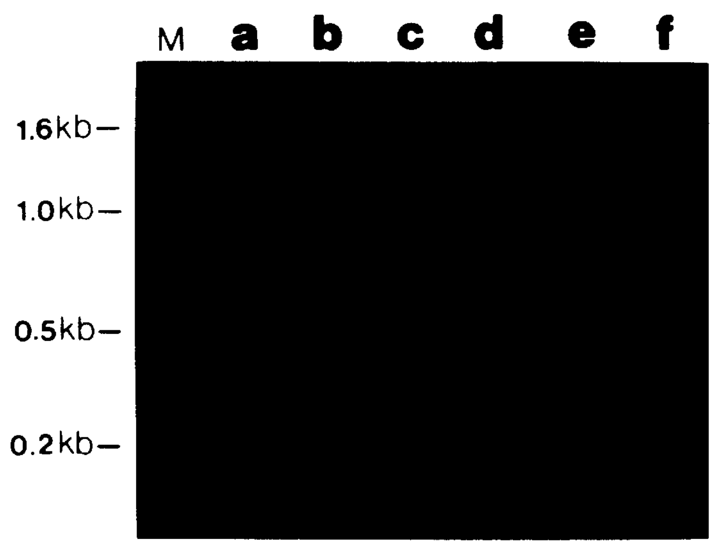

FIG. 4A (SEQ ID NO:3, SEQ ID NO:4, SEQ ID NO:5, SEQ ID NO:6, SEQ ID NO:7, SEQ ID NO:8, SEQ ID NO:9, and SEQ ID NO:10) illustrates the design of degenerate PCR primers for amplifying a BHV-1 dUTPase gene fragment. Oligonucleotides 1, 2 and 3 were used as the 5' primers, and oligonucleotides 4 and 5 were used as the 3' primers. The bold letters at the bottom of the figure represent the degenerate nucleotides as indicated.

FIG. 4B shows the profiles of PCR products electrophoretically separated on a 1% agarose gel. The primers used were: oligonucleotides 1 and 4 (lane a), 2 and 4 (lane b), 3 and 4 (lane c), 1 and 5 (lane d), 2 and 5 (lane e), and 3 and 5 (lane f).

FIG. 5 (SEQ ID NO:11 and SEQ ID NO:12) is the DNA sequence and the deduced amino acid sequence of BHV-1 dUTPase. The complete DNA sequence of the XhoI-SacII fragment as described in FIG. 6 and the deduced amino acid sequence are shown. A TATA box is indicated by the bold face letters and the relevant restriction endonuclease recognition sites are underlined.

FIG. 6 (SEQ ID NO:13 and SEQ ID NO:14) shows the DNA sequence and deduced amino acid sequence of the BHV-1 UL49.5 gene homolog. The DNA sequence represents the complementary strand of that shown in FIG. 5 and is numbered by setting the last nucleotide (1850) in FIG. 5 to −1. The arrow indicates the start codon and orientation of the dUTPase ORF.

FIG. 7 (SEQ ID NO:15 and SEQ ID NO:16) is the partial sequence of the BHV-1 VP4 gene promoter.

Figure 8:
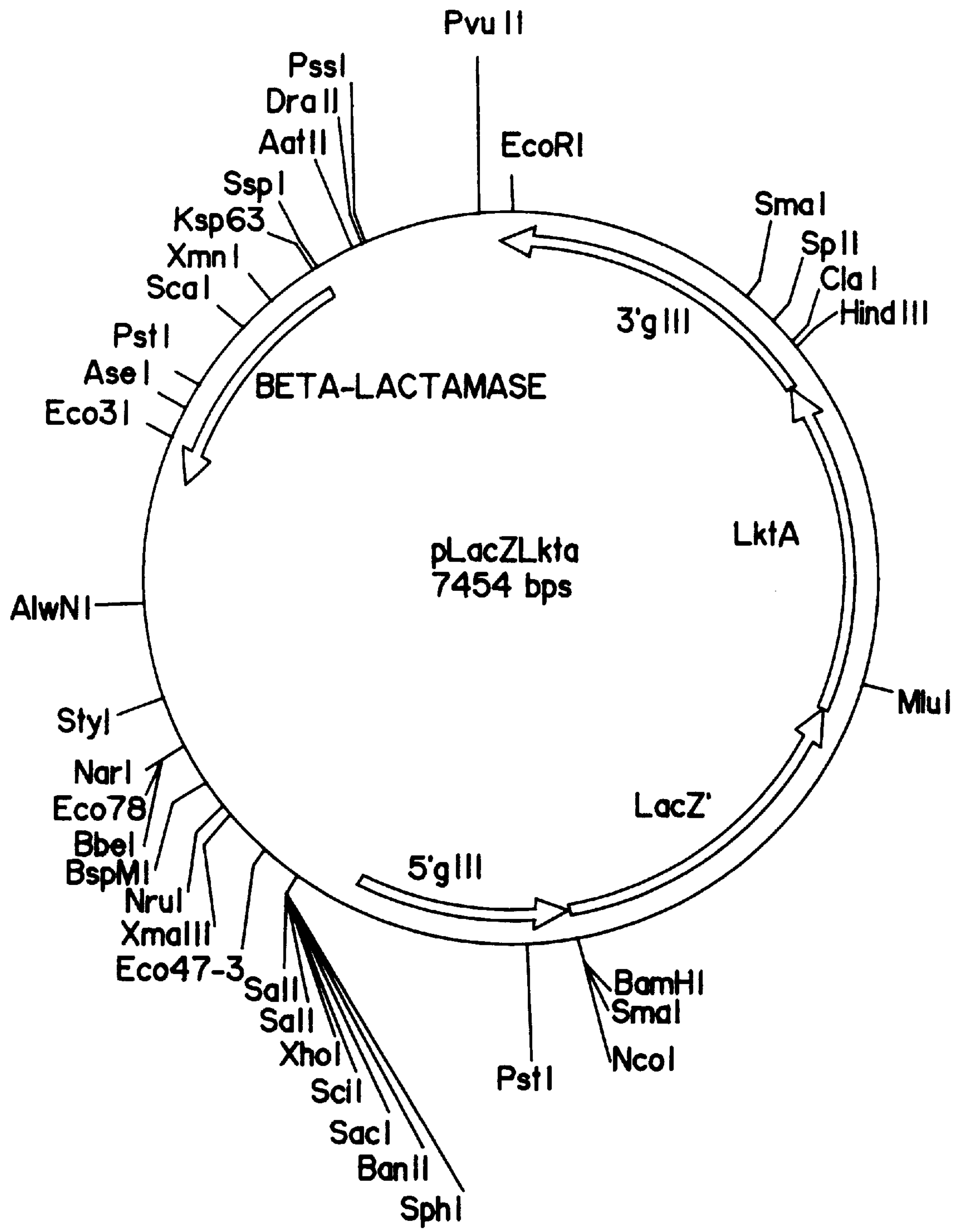

FIG. 8 is a map of the BHV-1 LacZ: LktA vector.

Figure 9:
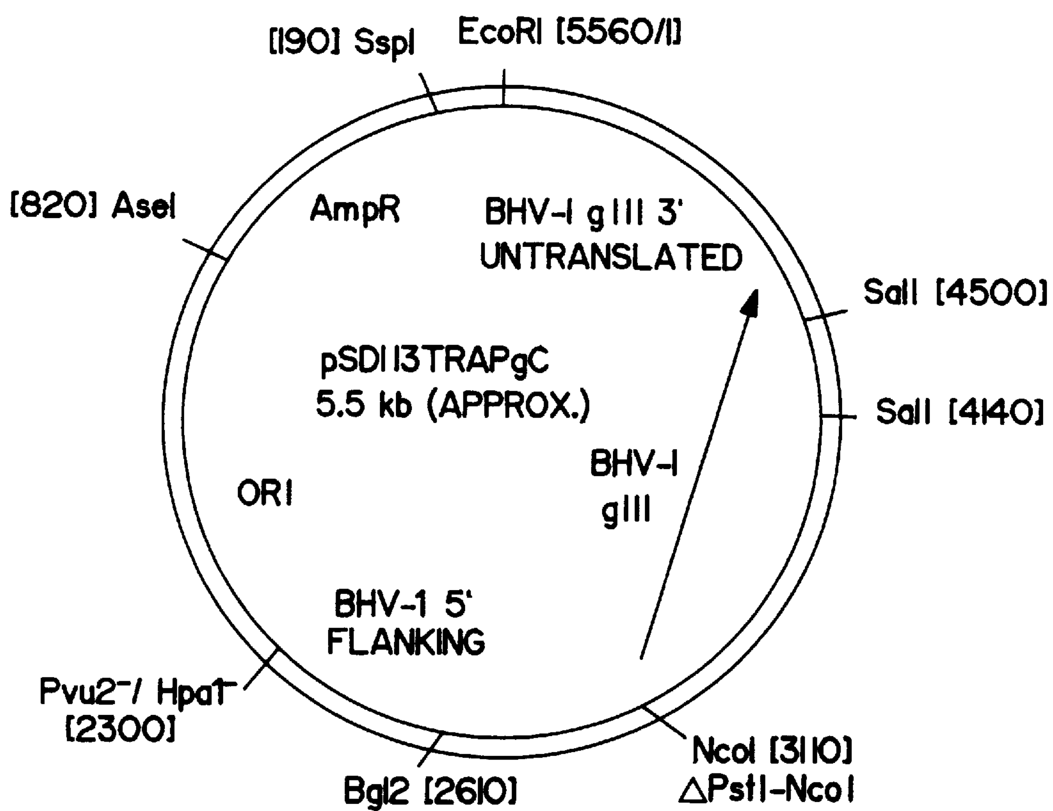

FIG. 9 is a map of the BHV-1 promoter trap vector (pSD113TRAPgC). Randomly generated DNA fragments can be inserted into the unique NcoI cloning site. Fragments inserted at this site reside in the same position normally occupied by the gIII (gC) gene promoter. The use of this plasmid and genomic DNA isolated from the $gIII^-$ BHV-1 in co-transfection experiments produces new recombinant viruses in which the randomly generated fragments reside immediately upstream from the gIII gene's coding sequence. Promoter activity associated with any of the randomly cloned fragments can be measured by black plaque assays, using gIII-specific monoclonal antibodies to detect expression of the gIII gene.

Figure 10:
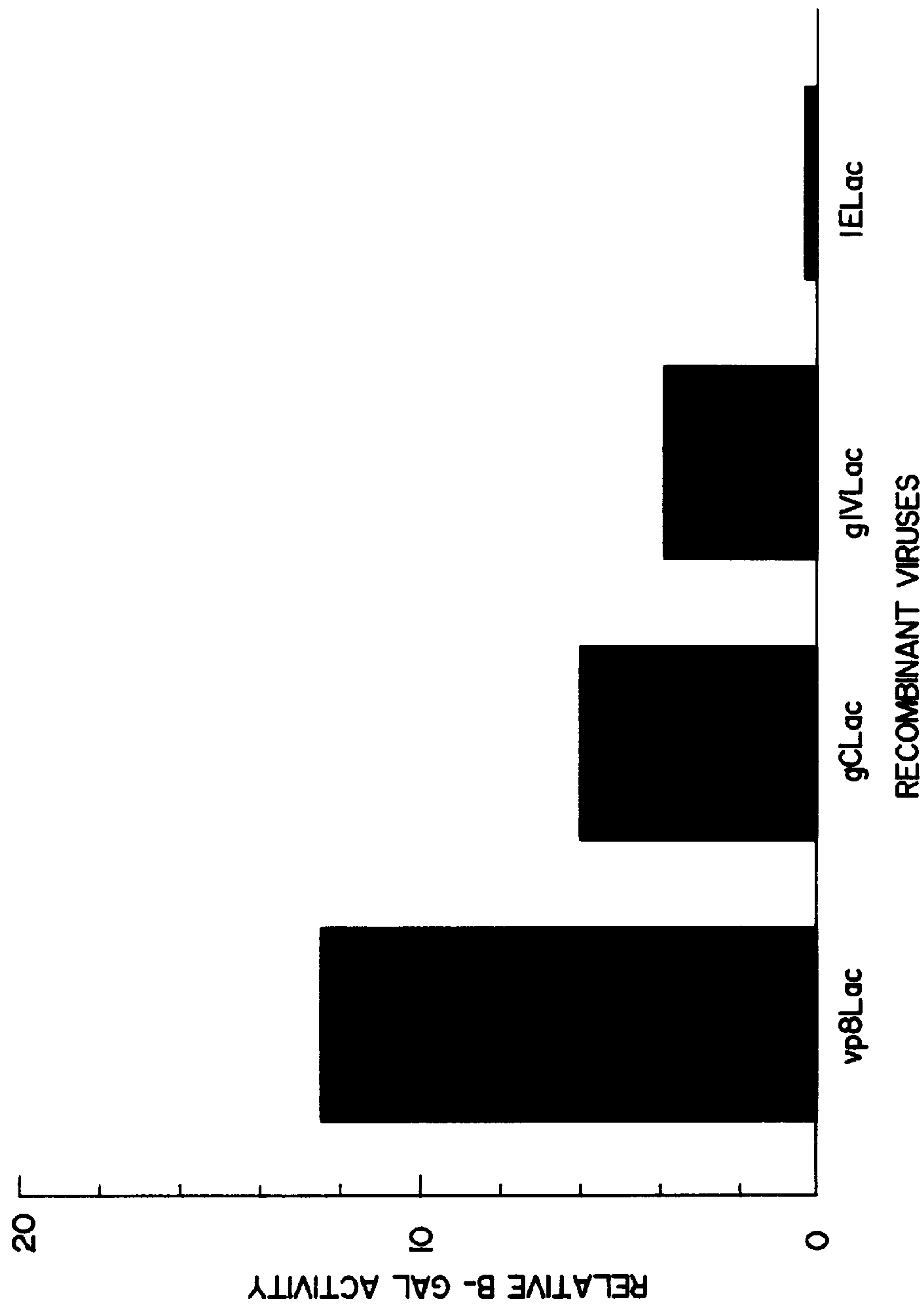

FIG. 10 shows LacZ gene expression driven by the vp8, gC, gIV, and IE promoters as measured by relative β-galactosidase activity.

FIG. 11 (SEQ ID NO:17 and SEQ ID NO:18) is the nucleotide sequence and deduced amino acid sequence of BHV 1 UL49 homolog gene. The complete DNA sequence between the UL48 homolog gene and dUTPase gene (UL50 homolog) and the deduced amino acid sequence of the UL49 homolog gene are presented. Putative G-C box, TATA box and polyadenylation sinal sequence are indicated by the bold face letters. The arrows indicate the boundaries of UL50, UL49.5 and UL48 ORFs surrounding the UL49 homolog gene.

FIG. 12 (SEQ ID NO:19, SEQ ID NO:20, and SEQ ID NO:21) presents an amino acid sequence comparison of UL49 homolog genes of BHV 1, HSV 1 and VZV. The amino acid sequences of the indicated UL49 homolog genes were compared using the CLUSTAL program (Higgins and Sharp (1988) *Gene* 73:237–244). The amino acid residues which are identical among the sequences compared are indicated by asterisks and those which are similar are indicated by dots. The HSV 1 sequence was deducted from the UL49 ORF of strain 17 (McGeoch et al. (1988) *J. Gen Virol*. 69:1531–1574); the VZV sequence was deducted from VZV gene 9 (Davison and Scott (1986) *J. Gen. Virol*. 67:1759–1816).

Figure 13:
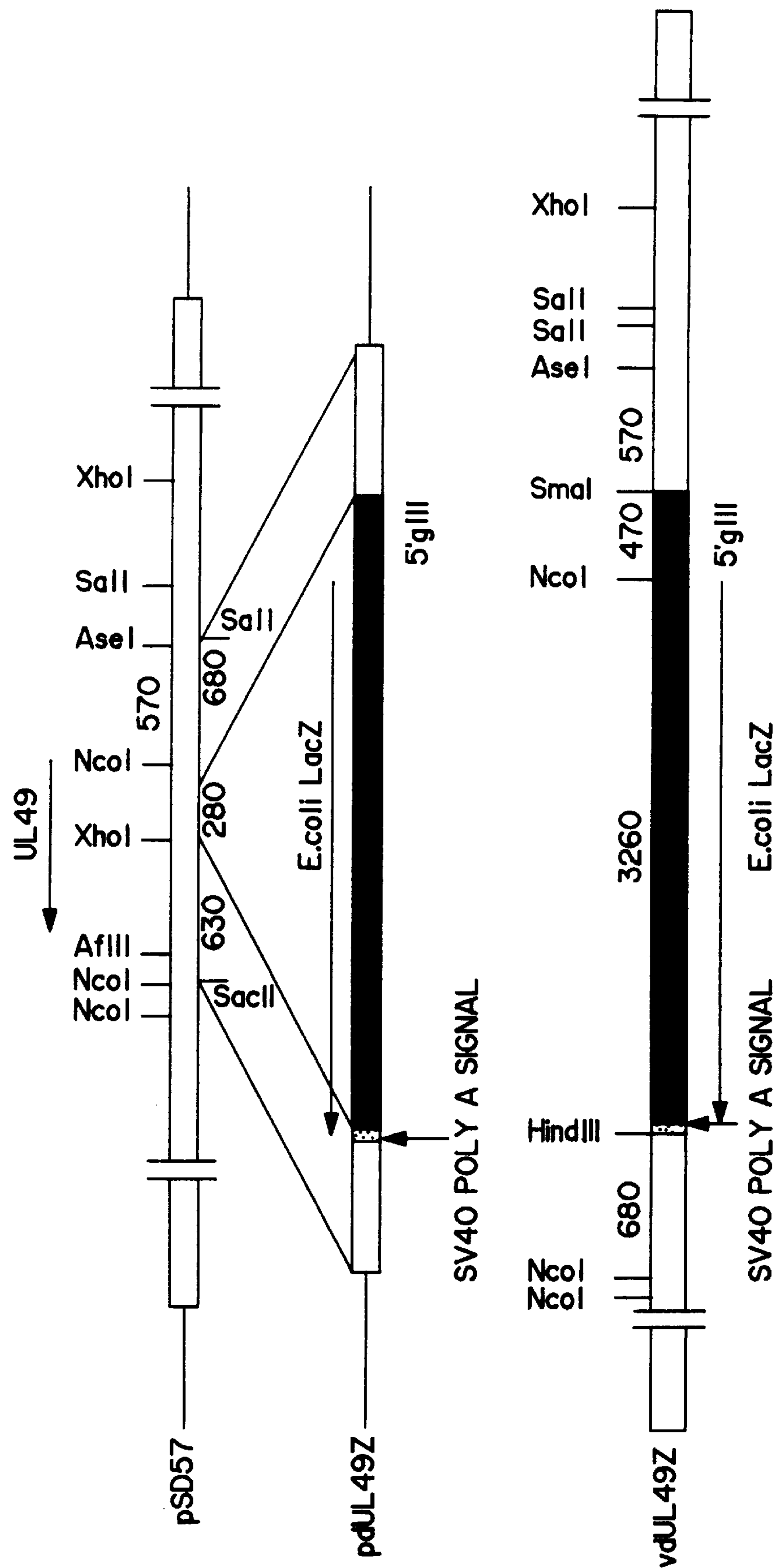

FIG. 13 is a schematic representation of transfer vector used in generating the UL49 homolog gene deletion mutant and predicted genomic organization of the mutant virus.

Figure 14:
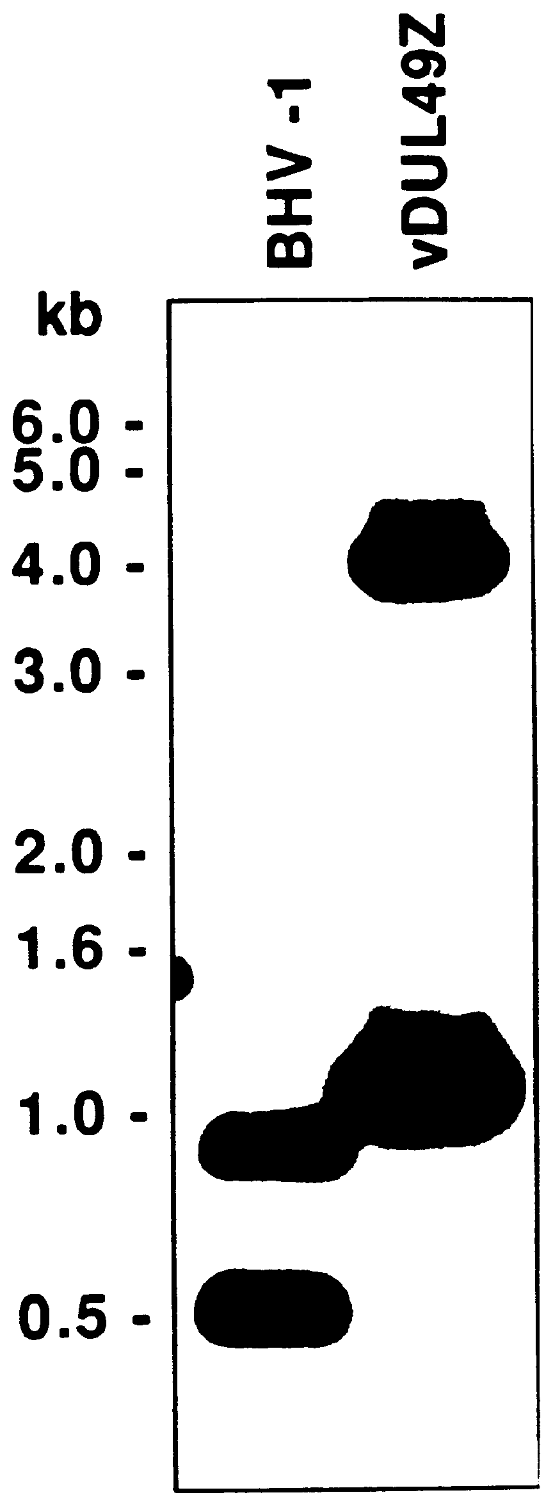

FIG. 14 shows Southern blot analysis to verify the genomic configuration of the UL49 homolog gene deletion mutant.

Figure 15:
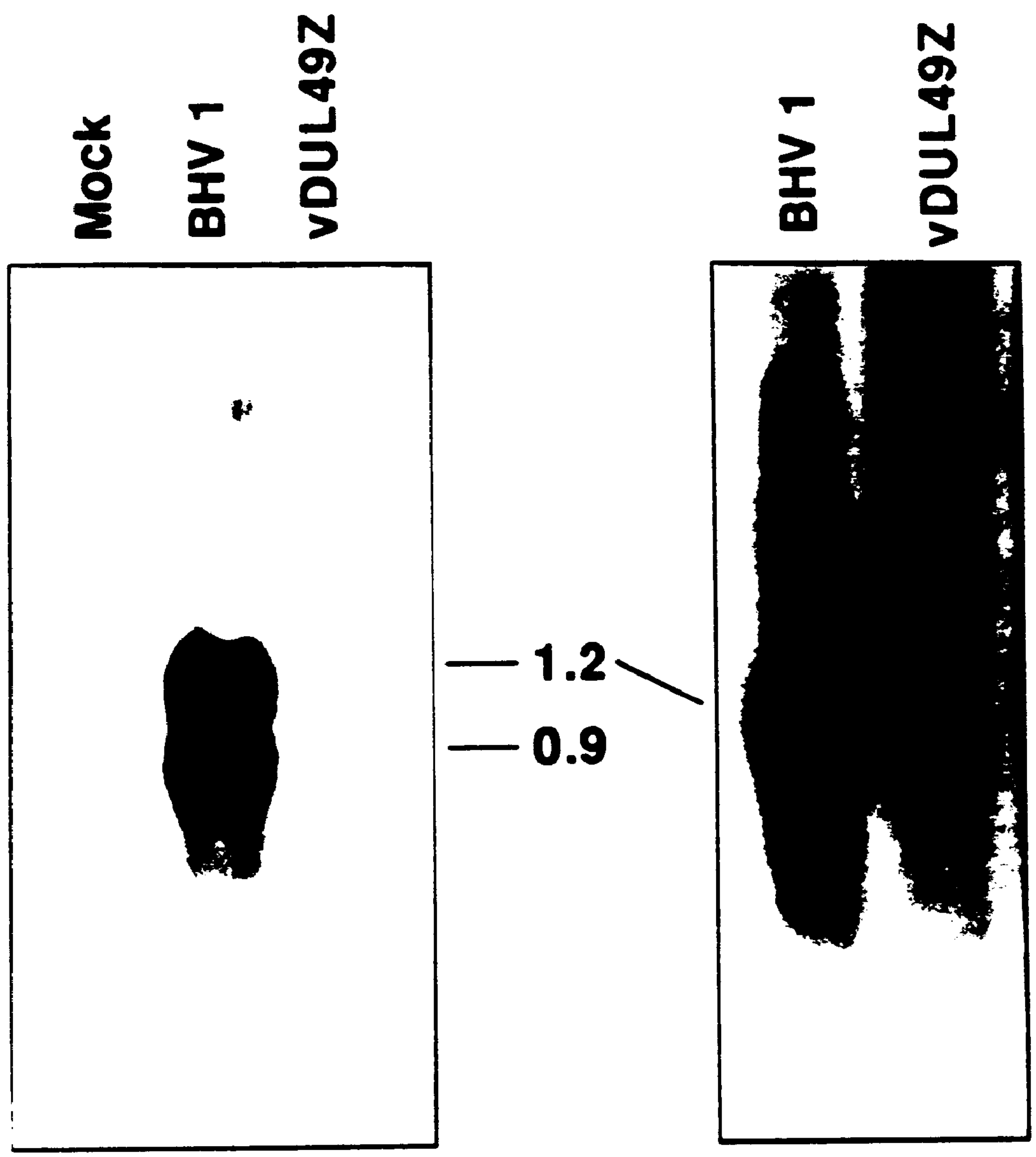

FIG. 15 shows Northern blot analysis of viral transcripts.

Figure 16:
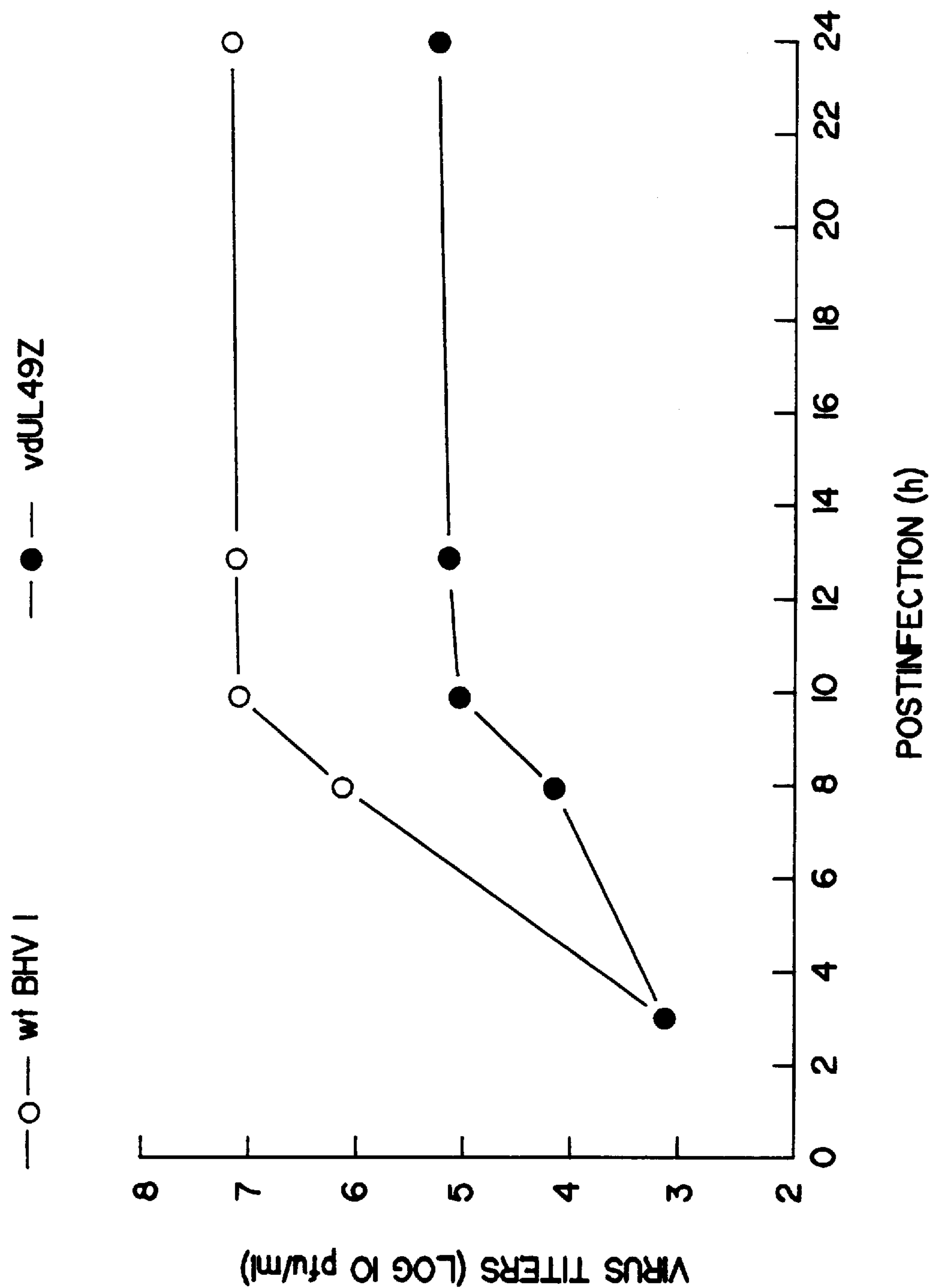

FIG. 16 is a single-step growth curve of the wild type (wt) BHV 1 and UL49 homolog deletion mutant in MDBK cells.

DETAILED DESCRIPTION OF THE PREFERRED EMBODIMENTS

It has been discovered that vaccines comprising attenuated and marked live BHV-1 vaccines can protect cattle from BHV-1 infection. It has further been discovered that vaccines comprising modified BHV-1 used as a vector for the expression of other bacterial or viral genes can simultaneously protect cattle against BHV-1 and bacterial and other viral pathogens. Surprisingly, these vaccines are substantially more protective than prior art killed-virus and attenuated live-virus vaccines.

The practice of the present invention will employ, unless otherwise indicated, conventional virology, microbiology, molecular biology and recombinant DNA techniques within the skill of the art. Such techniques are explained fully in the literature. See, e.g., Sambrook et al., MOLECULAR CLONING: A LABORATORY MANUAL (2nd Edition, 1989); Maniatis et al., MOLECULAR CLONING: A LABORATORY MANUAL (1982); DNA CLONING: A PRACTICAL APPROACH, Vol. I & II (D. Glover, ed.); OLIGONUCLEOTIDE SYNTHESIS (N. Gait, ed., 1984); NUCLEIC ACID HYBRIDIZATION (B. Hames & S. Higgins, eds., 1985); TRANSCRIPTION AND TRANSLATION (B. Hames & S. Higgins, eds., 1984); ANIMAL CELL CULTURE (R. Freshney, ed., 1986); Perbal, A PRACTICAL GUIDE TO MOLECULAR CLONING (1984).

All patents, patent applications and publications cited herein, whether supra or infra, are hereby incorporated by reference in their entirety.

A. Definitions

The following terminology will be used in accordance with the definitions set out below in describing the present invention.

An "attenuated and marked" vaccine is any vaccine comprising a virus wherein the virus is modified by deletion (s) and/or point mutation(s).

A "replicon" is any genetic element (e.g., a plasmid, chromosome or virus) that functions as an autonomous unit of DNA replication in vivo; i.e., capable of replication under its own control.

A "vector" is a replicon, such as a plasmid, phage or cosmid, to which another DNA segment may be attached so as to bring about the replication of the attached segment.

A "double-stranded DNA molecule" refers to the polymeric form of deoxyribonucleotides (adenine, guanine, thymine or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

"Strong promoter" as used herein means a control sequence that causes the efficient transcription of the coding sequence it controls. Non-limiting examples of strong promoters include endogenous promoters for such genes as tegument genes VP8 and $V_{MW65}$, capsid gene VP4; glycoprotein genes such as gI, gIII and gIV; and exogenous promoters such as alpha (immediate early) and beta human cytomegalovirus promoters, bovine heat shock 70A promoter, bacteriophage T7 promoter and the like.

"Weak promoter" as used herein means a control sequence that does not cause the efficient transcription of the coding sequence it controls. Non-limiting examples of weak promoters include endogenous promoters for such genes as dUTPase, gi and gE; and exogenous promoters such as SV40 early gene promoter and Rous Sarcoma virus LTR promoter.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

Two DNA or polypeptide sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; DNA CLONING, Vols I & II, supra; NUCLEIC ACID HYBRIDIZATION, supra.

The term "functionally equivalent" intends that the amino acid sequence of the subject protein is one that will elicit an immunological response, as defined below, equivalent to the specified BHV-1 immunogenic polypeptide.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the same source virus or virus-infected cells. Thus, heterologous includes "foreign genes" but is not limited thereto. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Non-essential gene" as used herein means a gene not essential for virus growth in cell culture, for example, a gene encoding a glycoprotein such as gE, gX, gi or a gene encoding an enzyme involved in nucleic acid metabolism such as dUTPase.

"Non-essential structural gene" as used herein means a structural gene not essential for virus growth in cell culture, for example, a gene encoding a glycoprotein such as gE, gX or gi.

"Essential genes" as used herein means a gene that is essential for virus growth in cell culture, for example, genes encoding a major capsid protein such as VP4, genes encoding tegument protein such as $V_{MW65}$ or VP8 or genes encoding essential glycoproteins such as gI and gIV.

"Gene regulating viral DNA metabolism" as used herein means a gene whose product is an enzyme that modifies nucleic acids. Non-limiting examples of such genes include genes encoding thymidine kinase, dUTPase and the like.

"Secretion signal sequence" as used herein means a DNA sequence which encodes the amino-terminal protein transport signal, a suitable sequence is the secretion signal sequence of the BHV-1 gIII gene.

A composition containing molecule A is "substantially free of" molecule B when at least about 75% by weight of the total of A+B in the composition is molecule A. Preferably, molecule A comprises at least about 90% by weight of the total of A+B in the composition, more preferably at least about 99% by weight.

"Bovine host" refers to cattle of any breed for which it may be desirable to immunize against BHV-1 infection, whether or not the bovine host is already infected or latently infected by BHV-1. A bovine host can be of any age. Thus, the term encompasses calves as well as adult cattle.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. A "glycoprotein" is a glycosylated polypeptide.

"Native" proteins or polypeptides refer to proteins or polypeptides recovered from BHV-1 virus or BHV-1-infected cells. Thus, the term "native BHV-1 polypeptide" would include naturally occurring BHV-1 proteins and fragments thereof. "Non-native" polypeptides refer to polypeptides that have been produced by recombinant DNA methods or by direct synthesis. "Recombinant" polypeptides refer to polypeptides produced by recombinant DNA techniques; i.e., produced from cells transformed by an exogenous DNA construct encoding the desired polypeptide.

"Deletion of a BHV-1 non-essential gene" as used herein means deletion of a nucleotide sequence encoding a gene or a portion thereof for a BHV-1 protein which is non-essential for virus growth in cell culture.

"Mutant analog" of a BHV-1 protein or gene as used herein means a protein having an amino acid sequence or a gene having a nucleotide sequence either of which differs from the native BHV-1 protein or gene sequence by one or more additions, substitutions or deletions. The term "mutant analog" does not comprehend mutant viruses lacking an entire gene such as BHV-1 lacking the dUTPase gene encoding sequence.

"Foreign gene" as used herein means DNA of a different source than the rest of the DNA. Foreign gene as used herein thus does not include non-native materials such as mutant analogs of the same source. Suitable non-limiting examples of foreign genes include:

(A) Genes encoding the following well-characterized antigens of respiratory pathogens of cattle:
   (i) *Pasteurella haemolytica* leukotoxin A (LktA) and leukotoxin B (LktB),
   (i) *Pasteurella haemolytica* plasmin receptor,
   (iii) bovine viral diarrhoea virus gp53, gp47 and gp25,
   (iv) bovine respiratory syncytial virus glycoproteins F and G, and
   (v) parainfluenza virus type 3 glycoproteins F and HN;
   (vi) *Hemophilus somnus* LppB;

(B) Genes encoding the following antigens of enteric pathogens can also be included in the recombinant BHV-1 vectors in stimulating the common mucosal immune system:
   (i) bovine coronavirus glycoproteins S and HE.
   (ii) bovine rotavirus proteins VP4, VP6 and VP7;

(C) Genes encoding immunomodulatory cytokines including the following, all of which can possess adjuvant activity, particularly when delivered in a site-specific manner to a mucosal surface and will dampen replication of the vaccine vehicle:
   (i) interleukin-1α (IL-1α),
   (ii) interleukin-1β (IL-1β),
   (iii)interleukin-2 (IL-2),
   (iv) interleukin-4 (IL-4),
   (v) granulocyte-macrophage colony stimulating factor (GM-CSF), and
   (v) the interferons.

A "native gene" or "native protein" as used herein means a gene having a nucleotide sequence or a protein having an amino acid sequence which does not differ from the gene or protein sequence found in wild-type BHV-1.

An "antigen" refers to a molecule containing one or more epitopes that will stimulate a host's immune system to make a humoral and/or cellular antigen-specific response. The term is also used interchangeably with "immunogen."

By "subunit antigen" is meant an antigen entity separate and discrete from a whole virus (live or killed). Thus, an antigen contained in a cell-free extract would constitute a "subunit antigen" as would a substantially purified antigen.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδ T cells, directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity or cell mediated immunity to provide protection of an immunized host. An "immunogenic polypeptide" as used herein, includes the full-length (or near full-length) sequence of the inserted protein or an immunogenic fragment thereof. By "immunogenic fragment" is meant a fragment of a polypeptide which includes one or more epitopes and thus elicits antibodies that neutralize viral infectivity, and/or mediates antibody-complement or antibody dependent cell cytotoxicity or cell mediated immunity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more subunit antigens.

The term "treatment" as used herein refers to either (i) the prevention of infection or reinfection (prophylaxis), or (ii) the reduction or elimination of symptoms of BHV-1 (therapy) or other diseases associated with inserted foreign genes.

B. Preferred Embodiments

Bovine herpesvirus type 1 (BHV-1) is a well-known and well-characterized virus, of which many strains are known. See, e.g., Gibbs et al. (1977) *Vet. Bull.* (London) 47:317–343. BHV-1, also known as infectious bovine rhinotracheitis virus, is similar in structure to other herpesviruses, and possesses a linear double-stranded DNA genome of approximately 140 kilobase pairs. BHV-1 can remain latent in infected animals, probably in trigeminal or sacral ganglia, and, as discussed above, can be reactivated with relative ease.

Accordingly, the invention includes vaccine compositions comprising mutant attenuated live-BHV-1 wherein non-essential genes are deleted and/or essential genes are mutated in order to attenuate the virus. The deleted genes are replaced with foreign genes and/or mutant analogs of genes encoding BHV-1 immunogens. In the case of a mutant BHV-1 comprising mutations of an essential gene, a foreign gene or mutant analog can be inserted at another gene location. A mutant BHV-1 gene optionally comprises endogenous BHV-1 promoters or exogenous promoters which can be used to express a foreign gene or a mutant analog gene.

The invention also includes vaccine compositions comprising a mutant attenuated live BHV-1 comprising a combination of gene deletion(s) and promoter(s) and one or more foreign genes and/or genes encoding immunomodulatory cytokines.

Multiple combinations of more than one antigen and/or cytokine gene are contemplated by the present invention. For multiple combinations, genes encoding antigens can be placed behind strong and/or late promoters while genes encoding cytokines can be placed behind weak and/or early promoters. This strategy facilitates (i) early delivery of recombinant cytokines before endogenous cytokines are elicited (by the inflammation associated with viral infection), and (ii) delivery of immunomodulatory cytokines before and/or during antigen delivery to maximize potential adjuvant-like effects (as opposed to cytokine delivery after antigen delivery).

Exemplary of suitable cytokines within the present invention are interleukin-1α, interleukin-1β, interleukin-2, interleukin-4, granulocyte-macrophage colony stimulating factor, interferon-γ and other interferons.

Promoters and non-essential genes within the present invention include the gIII gene and its promoter (Fitzpatrick et al. (1989) *Virology* 163:46–57), genes for gII and the glycoproteins homologous to herpes simplex virus Us5 and Us4 (Longnecker et al. (1987) *Science* 236:573–576 and *Proc. Natl. Acad. Sci. USA* 84:4303–4307; McGeoch et al. (1988) *J. Gen. Virol.* 69:1531–1574, Weber et al. (1986) *Science* 236:576–579), and promoters for gI, gIV, VP4, VP8, gH and/or immediate early genes (Petrovskis et al. (1988) Abstract of the 13th International Herpesvirus Workshop, U. Cal., Irvine and Zamb, T. J. (1987) Abstract 330, 68th Annual Meeting of the Conference of Research Workers in Animal Diseases, Chicago). Other potential genes and promoters can be used which represent other "non-essential" genes (Mettenleiter et al. (1988) *J. Virol.* 62:12–19, Rea et al. (1985) *J. Virol.* 54:21–29 and Thomsen et al. (1987) *J. Virol.* 61:229–232), and/or represent a range of different temporally regulated promoters (Homa et al. (1988) *Vet Immnunol. Immunopathol.* 17:357–365) and/or different promoter strengths (Petrovskis et al. (1988) Abstracts of the 13th International Herpesvirus Workshop, U. Cal., Irvine) which can be useful for differential regulation of the time and/or level of expression of more than one gene in the same recombinant virus.

Examples of non-essential genes suitable for deletion within the present inventions include, but are not limited to, genes encoding glycoproteins such as gX, gE and gi, and enzymes involved in nucleic acid metabolism such as dUTPase.

A BHV-1 mutant analog within the present invention can exhibit improved characteristics for purposes of the present invention. In a preferred embodiment, mutations are introduced in the gene encoding VP4 capsid protein which results in an unstable capsid protein which causes the mutant BHV-1 to be increasingly sensitive to temperature. In another preferred embodiment, mutant analogs of the $V_{MW65}$ gene are produced which in turn produce a gene product defective in regulating BHV-1 gene transcription.

Exemplary foreign genes suitable for insertion into BHV-1 for the purposes of gene expression and antigen delivery to the mucosal surfaces of cattle within the present invention are genes encoding:

Bovine Viral Diarrhea Virus (BVDV):
- gp53 (the major viral envelope gp);
- gp47 (a minor viral gp); and
- p14 (nucleocapsid);

Bovine Respiratory Syncytial Virus (BRSV):
- F (fusion protein); and
- G (the major viral glycoprotein);

Parainfluenza 3 Virus (PI3V):
- F (fusion protein);
- HN (hemagglutinin/neuraminidase); and
- N (nucleocapsid);

*Pasteurella Haemolytica:*
- LktA (leukotoxoid A);
- LktB (leukotoxin B); and
- plasmin receptor.

*Hemophilus Somnus:*
- LppB (lipopolyprotein 40K)

Rotavirus (BRV):
- VP6;
- VP4; and
- VP7

Coronavirus (BCV):
- HE (hemagglutinin)
- S (spike protein)

Results obtained expressing β-galactosidase at various loci within BHV-1 genome indicate that recombinant virus replication efficiency is dependent on the viral gene that was disrupted and is independent of foreign gene expression itself. Thus, any genetic locus which encodes a nonessential viral protein can be a suitable foreign gene insertion site. Disruption of a nonessential gene may, however, interfere with transcription of adjacent genes if the genes are co-transcribed. Suitable insertion loci within the present invention include the gi, gX, gE and dUTPase genes.

An efficient BHV-1 vaccine vehicle must effectively express the inserted foreign gene sequences. Efficient gene expression requires the incorporation of transcriptional and translational control sequences in the foreign gene constructs.

Suitable endogenous promoters within the present invention include, but are not limited to, BHV-1 gIV gene promoter, BHV-1 gIII gene promoter, BHV-1 VP4 (nucleocapsid protein) gene promoter, VP8 (major tegument protein) gene promoter, and the $V_{MW65}$ (minor tegument) gene promoter. Strong promoters that drive the highly expressed BHV-1 genes are particularly preferred. These promoters include, but are not limited to, promoters of the capsid (VP4), glycoprotein (gIII) and tegument genes (VP8 and $V_{MW65}$).

Suitable exogenous promoters within the present invention include, but are not limited to, bovine heat shock 70A gene promoter, human cytomegalovirus immediately early gene promoter, and adenovirus major late promoter.

An additional set of promoters for expression of foreign genes can be constructed by creating hybrid forms of endogenous BHV-1 promoters in order to yield novel patterns of temporal regulation. Exemplary of such hybrid forms is a promoter created by the fusion of the CAAT box promoter element of the "early" gI gene with the TATA box promoter element of the "late" gIII gene to yield a hybrid promoter which drives expression at both early and late times post-infection.

A preferred vector for recombinant BHV-1 construction includes the genes encoding *P. haemolytica* Lkt and/or IL-2 recombined into BHV-1. Each of the genes can be inserted behind a number of different promoters to test different levels of expression of the genes and to facilitate development of combination vectors.

C. General Methods

A BHV-1 gene, for example, the gIII gene (Fitzpatrick et al. (1989) *Virology* 173:46–57) can be manipulated by methods disclosed by Maniatis et al. (supra) to (i) create a useful cloning site immediately behind the start codon, signal sequence, and/or the first few amino acids of the amino-terminus of the BHV-1 gene and (ii) delete the remainder of the BHV-1 gene open reading frame—but retaining the 3' untranslated segment of the BHV-1 gene. These constructions allow insertion of foreign genes behind the gIII promoter for high level "late" expression (Homa et al. (1988) *Vet. Immunol. Immunopathol.* 17:357–365) and/or behind the BHV-1 gene start codon or signal sequence for intracellular synthesis or secretion/membrane insertion, respectively. Constructions containing the first few amino acids of the BHV-1 gIII can exhibit elevated levels of translation, membrane insertion, stability, and/or general expression. Retaining the 3' untranslated region provides a BHV-1-specific polyadenylation signal and completely flanks the foreign gene with BHV-1-specific expression signals.

This construction can then be substituted for the BHV-1 gene in the parent plasmid pSD113 (Mayfield et al. (1983) *J. Virol.* 47:259–264), in order to facilitate recombination during transfections. The construction can also be subcloned into the plasmid pSD98 (Mayfield et al., supra)—in place of other putative "non-essential" genes such as gE, or BHV-1 homologues of HSV-1 Us4 or Us5 (Longnecker et al. (1987) *Science* 236:573–576 and *Proc. Natl. Acad. Sci. USA* 84:4303–4307, McGeoch et al. (1988) *J. Gen. Virol.* 69:1531–1574, Weber et al. (1986) *Science* 236:576–579). This latter plasmid may be required if deletion of a BHV-1 gene has deleterious effects on the growth of the recombinant virus in vitro or in vivo (Mettenleiter et al. (1985) *J. Virol.* 56:307–311; Robbins et al. (1986) *J. Virol.* 59:635–645). These constructions can be tested using β-galactosidase, firefly luciferase, pseudorabies virus gIII and/or bovine INF-γ as reporter genes.

Recombinant forms of BHV-1 are obtained by co-transfection of the above constructions with BHV-1 DNA into MDBK cells. Recombinants can be identified via the "blue plaque," "black plaque," and/or "white plaque" methods and can be selected using antisera directed against the gene of interest, for example, gIII deletion constructions are detected with anti-gIII antisera, i.e., white plaque method. To detect viruses with other deletions, the selectable marker systems noted above can be used.

Expression of reporter genes can be further evaluated in vitro by the plaque methods discussed above, polyacrylamide gel electrophoresis, immunoprecipitation, Western blotting and/or colorimetric/indirect immunological measurement of enzyme/cytokine activity using both infected cell lysates and supernatant fluids.

Replication of recombinant viruses in vitro can be monitored by one-step growth kinetic experiments. Stability of recombinants can be tested by extensive low multiplicity-of-infection passaging on MDBK cells.

Methods for the preparation and evaluation of mutant genes and proteins within the present invention are well known in the art. Non-limiting examples of mutagenesis techniques include (1) substitution of one or more amino acids by another, for example, substitution by an isosteric residue having a different function, e,g., substituting Asn for Asp; a residue having a different function; a residue having an identical function but a different primary, secondary or tertiary structure, e.g., Asp for Glu; helix breakers such as Pro; substitution of glycosylated amino acids for non-glycosylated amino acids and the like or vice versa; replacing Cys with another residue to delete disulfide bridge formation; and (2) addition or deletion of one or more amino acids to produce isosteric, functional or structural differences in the proteins. Primary structure changes include hydrophobicity or hydrophilicity modifications, secondary structure changes include local folding alterations and tertiary structure changes include changes in the 3-D structure of a protein.

Deletion mutants include deletion of at least one amino acid. Deletions can start at any amino acid in the molecule. Two or more consecutive amino acids can be deleted. Alternatively, at least one amino acid can be deleted in two or more separate locations of the molecule. Usually, a single amino acid is deleted at a particular position. The expressed deletion mutant proteins can be antigenic or non-antigenic depending on the position of the deletion and each kind can be useful for vaccines or diagnostics as discussed hereinafter. In a preferred embodiment, deletion mutations of homologous (BHV-1) structural immunogens such as gIV are provided. In another preferred embodiment, larger deletion mutations in, for example, the transmembrane anchor are provided.

One embodiment is directed to the replacement of one or more cysteine residues by another non-sulfur containing amino acid while another is directed to mutations of the N-terminus, C-terminus or an internal region.

Specific mutations can be introduced in the DNA. Site-specific deletion mutation is one preferred means of preparing deletion mutants of the invention but other known techniques can be used. The mutants can be tested for their antigenic activity in Western blotting experiments using monoclonal antibodies raised against native BHV-1 proteins.

The tegument gene, which is critical in controlling the transcriptional cascade of herpesvirus genes, can be modified via point mutation. In addition to being a major structural component of herpesviruses, tegument, in association with host cell factor(s), initiates virus transcription events leading to productive infection. Thus, by judicious site directed mutagenesis of the tegument gene, virus gene regulation can be altered such that in vivo replication of BHV-1 is less efficient. A map of the BHV-1 $V_{MW65}$ gene homolog is shown in FIG. 1. The DNA sequence of the BHV-1 $V_{MW65}$ gene homolog is shown in FIG. 2. Specific nucleotides within the BHV-1 tegument coding sequence (or in the gene regulation sequences) can be altered in vitro and then introduced into the wild-type virus by the co-transfection methods described herein. A foreign gene can be carried at an alternate site, e.g., the gX gene locus in this attenuated virus.

Another mechanism for virus attenuation is mutating viral genes involved in DNA metabolism such as the alpha-herpesvirus thymidine kinase (TK) gene which encodes an important virulence factor involved in DNA metabolism. The TK gene is deleted in a commercially available live pseudorabies virus vaccine. Similarly, the dUTPase gene has been shown to encode an HSV-1 virulence factor (Pyles et al. (1992) *J. Virol.* 66:6706–6713). The dUTPase gene product converts dUTP into dUMP thereby making it inaccessible for incorporation into new viral genomes replicated in infected cells.

In order to evaluate this gene and its role in virulence, the position of the BHV-1 dUTPase gene was mapped, using polymerase chain reaction technology and degenerate oligonucleotide primers based upon two highly conserved domains within the dUTPase family of genes (McGeoch (1990) *Nuc. Acids Res.* 18:4105–4110). The results of the subcloning and sequencing of the BHV-1 dUTPase gene are shown in FIG. 5. Based upon this information, the coding sequence of this gene can be deleted in the BHV-1 genome. This can be accomplished by making an insertion plasmid carrying the non-coding sequences immediately 5' and 3' to the dUTPase gene without the intervening coding sequences. Co-transfecting cells with this plasmid and wild-type BHV-1 (Cooper) DNA allows for homologous recombination between the plasmid and the viral genome, mediated by the BHV-1 sequences on the plasmid that normally flank the dUTPase gene. Recombinant viruses lacking the dUTPase gene coding sequence can be generated by these recombination events. The relative virulence of this gene-deleted virus can be tested in cattle challenge trials. Functional foreign gene sequences encoding a relevant protective immunogen(s) can be inserted at either the dUTPase locus, or at one of the minor glycoprotein gene loci. Foreign gene sequences can be inserted at the gX, gE and gi gene loci as determined by experiments wherein the gIII gene promoter/lac Z reporter gene cassette was successfully inserted at the gIII and gX loci.

The gIII gene promoter can be used to drive the expression of the *E. coli* lac Z gene, not only at the gIII locus, but also, at other loci throughout the genome. In addition, recombinant virus which express β-galactosidase, under control of the gIII gene promoter, can effectively induce serum antibody responses to β-galactosidase in recombinant virus-infected cattle. These results demonstrate that gIII promoter activity is preserved when it is relocated to different positions within the BHV-1 genome and that the gIII promoter has the strength needed to drive foreign gene expression to a sufficient level to elicit host immune responses to the foreign antigen. The level of foreign antigen expression by a viral vector required to elicit a host immune response depends, however, on the replication efficiency of the viral vector itself. For example, a low level of foreign gene expression by a relatively virulent viral vector can be sufficient to stimulate the host immune response, whereas, in order to achieve the same degree of immune stimulation, expression of significantly higher amount of foreign antigen may be required with a severely attenuated viral vector.

In addition to using promoters isolated directly from the BHV-1 genome to drive the expression of foreign genes, other strong promoters from heterologous systems can be used which include: alpha (immediate early) and beta 2.7 gene promoters from human cytomegalovirus (Spaete and Mocarski (1985) *J. Virology*, 56:135; the heat-shock promoter recently isolated from bovine cells (Kowalski, J. et al. *Vaccines*, in press), or; the T7 promoter system which requires the expression of the T7 polymerase gene to drive the expression of a foreign gene cloned downstream from and under the control of a T7 polymerase sensitive promoter (Elroy-Stein and Moss (1990) *Proc. Natl. Acad. Sci. USA*, 87:6743–6747).

Proper foreign gene expression requires the efficient termination of transcription. The sequence of the gI gene was described in U.S. Pat. No. 5,151,267. Included in this sequence is a 3' untranslated region (UTR), containing a distinct polyadenylation signal and a poly A addition site. This sequence, when cloned downstream of a foreign gene, provides a signal for efficient transcription termination. Synthetic oligonucleotides which mimic the untranslated sequences 3' of the gI gene can be made and used in the foreign gene insertion plasmids, such that they reside immediately downstream from the foreign gene insertion site. Termination codons can be included in all three possible reading frames immediately in front of the gI gene's UTR to ensure efficient translation termination of the foreign gene product.

Inspection of the highly expressed BHV-1 genes shows that their structure is consistent with the Kozak rules, in that the initiation codon of the highly expressed genes are surrounded by GC rich sequences (Kozak (1978) *Cell* 15:1109–1123. These sequences cause high affinity binding of gene transcripts to ribosome complexes. For example, the gIII, VP4 and VP8 gene initiation codons are contained within Nco I sites, i.e., CCATGG. When using any of the strong promoters to cause foreign gene expression by BHV-1, the Nco I site at the initiation codon can be conserved by correcting any of the potential foreign gene inserts such that their initiation codons are also contained within an Nco I restriction endonuclease site. The procedures which can be used for sequence alteration include: PCR cloning; site directed mutagenesis, or; gene reconstruction using synthetic oligonucleotides. Site corrections of this type allow for the rapid insertion of foreign genes into the BHV-1 insertion vectors, and ensure that gene inserts conform to the Kozak rules for preferred nucleotides at the site of translation initiation.

Since many of the genes encode glycoproteins, it is useful to pay attention to the efficiency by which these proteins can be transported (Lawrence et al. (1990) XV International Herpesvirus Workshop Abstract) to the surfaces of and, in special cases secreted from, cells infected with the relevant BHV-1 cloning vehicle.

U.S. Pat. No. 5,151,267, which is hereby incorporated by reference, describes the DNA sequence of the BHV-1 gIII gene, including those sequences which encode the amino-terminal protein transport signal. The protein product encoded by this gene is expressed in high levels and efficiently transported. The signal sequences of foreign glycoprotein genes destined for BHV-1 insertion can be replaced with the sequences encoding the gIII gene signal. Efficient post-translational processing and protein transport mediated, in part, by these sequences can improve the efficiency of production and the immunogenicity of the foreign glycoprotein produced by the BHV-1 vector. The translation efficiency of the foreign gene can be increased, as well, by using the gIII gene's signal. The rate of translation from the foreign gene transcripts improves since translation can commence with the gIII signal sequence which is encoded by triplets commonly used in highly expressed herpesvirus genes. Codon bias plays a significant role in levels of translation, in that highly expressed genes use a subset of the known codons (Grantham et al. (1981) *Nucl. Acids Res.*

9:r43–r74. In addition, codon bias can become important when considering foreign gene expression mediated by herpesviruses, since many of these viruses have a very high GC content, approaching 80% for most genes. Thus, the preferred codons used by BHV-1 are GC-rich as well, while most of the genes selected for expression by this virus have more average GC content. In other systems the translation efficiency of the entire transcript can be greatly increased by modifying the codons at the amino terminus of a gene, such that they conform to the codon bias used by the highly expressed genes of that system.

Causing the secretion of a typically membrane associated glycoprotein increases the yield of that protein. For example, the amount of secreted gIV (the anchor sequence$^-$ construct) produced by a particular pox virus expression system is 100-fold higher than the amount of membrane associated gIV (anchor sequence$^+$) made by the same promoter system. A similar, but less dramatic, difference was observed when the same constructs were expressed by recombinant adenoviruses. The BVDV gp53 gene construct, with and without its anchor sequence, can be produced by fusion to the gIII gene promoter and the resulting constructs inserted at the BHV-1 gX gene locus. The level of recombinant gp53 produced by each construct can be evaluated in vitro. Both BHV-1 recombinants can be tested for the degree of protection they confer to cattle from virulent BVDV challenge. The immune responses elicited to gp53 by the two constructs can be closely compared and the probable differences in the absolute amounts of gp53 produced determined. The relative intensity of the immune response, and the differences in the type of the response elicited by the two versions of gp53 can also be determined. For example, the membrane associated protein may produce a more efficient CMI response, while the secreted form of the same molecule may produce a better antibody response.

Herpesvirus gene expression is strictly and temporally regulated. Directly after entering cells of the permissive host, the immediate-early (IE) genes of the virus are transcribed. The protein products of these genes then coordinate the transcription of the subsequent temporal classes of genes, responsible for either initiating or terminating their transcription in a coordinated fashion. Expression of the IE genes is directly followed by early gene expression, viral DNA replication and then late gene expression. Therefore, virus encoded factors which regulate the virus gene expression cascade must be critical to the normal virus replication process and, therefore, must represent important virulence factors in virus pathogenesis. Among these factors, VP16 (the $V_{MW65}$ gene product, or α-trans-inducing factor) of HSV has been best characterized. This viral protein serves at least two functions: (a) it is the major structural component of the virus tegument; and (b) it is a critical transactivating factor required for IE gene expression. While HSV-1 VP16 is an essential virus protein, mutations are tolerated at the region of the $V_{MW65}$ gene which is responsible for encoding the transactivation functions. Virus mutants lacking VP16 transactivating activity must be added in high concentrations in order to produce productive infections in cell culture, indicating that these mutants are highly attenuated. Thus, producing mutations which alter transcriptional transactivation functions of VP16, while not significantly altering the overall structure of this protein, can provide an additional means of attenuating the virus.

Recombinant vaccinia virus expressing interleukin 2 (IL-2) is significantly less virulent in immune compromised mice, when compared with wild-type vaccinia virus. This is partly due to induction of local gamma-interferon production caused by the IL-2 expressed by the recombinant virus. In addition, recombinant vaccinia virus expressing tumour necrosis factor (TNF) α was found to be rapidly and efficiently cleared from normal mice, and significantly attenuated in immunodeficient mice. This appears to be due to the direct antiviral effect of TNF, rather than a local enhancement of cellular or humoral immune responses.

Another strategy for attenuating BHV-1 involves the expression of relevant bovine cytokine genes by recombinant BHV-1. Such a recombinant BHV-1 may also provide a means of preventing latent virus infection by a BHV-1 vaccine vehicle. The lack of MHC antigen expression on the surfaces of virus infected cells [either as an inherent property of the cells themselves, such as neurons, or due to an interference of MHC antigen presentation caused by a viral gene product] prevents the destruction of virus infected cells by cytotoxic T cells and, as a result, may lead to establishment of persistent or latent viral infections. Cytokines, such as gamma-interferon, are well documented for their ability to stimulate MHC molecule expression. Therefore, a recombinant virus that expresses these cytokine(s) can boost expression of MHC antigen by the infected cells, which can reduce, and perhaps block, latent infections. This is of particular interest, since no herpesvirus mutants have thus far been identified which are unable to establish latency. Thus, attenuation of the BHV-1 vaccine vehicle can be achieved by providing constructs which will express bovine cytokines which comprise, for example, mutations of the BHV-1 $V_{MW65}$ gene homolog and bovine cytokine genes such as IL-1α, IL-1β, IL-2 or gamma-IFN.

The production of a truly efficacious vaccine delivery system requires careful consideration of: (a) the appropriate promoter used to drive the expression of the foreign gene; (b) the sites within the genome of the vehicle which will allow foreign gene insertion and expression; and (c) judicious selection of relevant genes encoding protective immunogens.

The vaccines are formulated into a vaccine composition comprising a pharmaceutically acceptable vehicle and, optionally, an adjuvant. Such formulations are well within the skill of the art. In general, the formulations will be particularly adapted for intramuscular injection, since intravenous injection is usually not practical for large-scale application to domestic animals. Alternatively, the vaccines are given orally or intranasally, and the subunits formulated with a suitable oral carrier. It may be preferred to administer the vaccines of the present invention orally to raise mucosal immunity, as well as intramuscularly for systemic immunity. A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and tris buffer, while examples of preservatives include thimerosal, m- or o-cresol, formalin and benzyl alcohol. Standard formulations will either be liquid injectables or solids which can be taken up in a suitable liquid as a suspension or solution for injection. Thus, in a nonliquid formulation, the vehicle may comprise dextrose, human serum albumin, preservatives, etc., to which sterile water or saline could be added prior to administration.

Various adjuvants are known in the art which can also be employed in the vaccine formulations of the present invention; e.g., Freund's adjuvant, Avridine, aluminum salts [Al $(OH)_3$, $AlPO_4$, $Al_2(SO_4)_8$], $Ca_3(PO_4)_2$, saponin, DDA, Pluronics, oil-in-water emulsions (containing, e.g., Avridine, dextran sulphate, Emulsigen PLUS or vitamin E) and water-in-oil emulsions (containing, e.g., polysorbate 80). The selection of the appropriate adjuvant and its concentration in the vaccine composition is within the skill of the art.

Many protocols for administering the vaccine composition of the present invention to animals are within the skill of the art. The preferred route of administration is intranasally or parenterally, particularly intramuscularly. The concentration of the antigen(s) in the vaccine composition is selected so that an effective dose is presented in the bovine host to elicit cell mediated immunity or antibodies to the polypeptide neutralizing epitopes. Within wide limits, the dosage is not believed to be critical. Typically, the vaccine composition is administered in a manner which will deliver between about $10^5$ to about $10^8$ plaque forming units (PFU) in a convenient volume of vehicle (e.g., about 1–10 ml). Preferably, the dosage in a single immunization will deliver from about $10^6$ to about $10^7$ PFU of antigen. It may also be preferred, although optional, to administer a second, booster immunization to the animal several weeks to several months after the initial immunization. To insure sustained high levels of protection against disease, it may be helpful to readminister a booster immunization to the animals on a periodic basis.

Diagnostic Assays for BHV-1 Antibodies

The recombinant antigens of BHV-1 tegument, capsid and (glyco)proteins such as VP4, VP8, $V_{MW65}$, gi, gX and/or gE can be used as substrate reagents in immunoassays to identify antibodies to these BHV-1 proteins in a sample, e.g., blood, from a bovine host as one means of determining if the bovine host is infected with BHV-1 and to determine the concentration of the antibodies in the sample. Immunoassays employing recombinant antigens of BHV-1 proteins within the present invention include, but are not limited to, radioimmunoassay, competition immunoassay, immunoprecipitation, enzyme-linked immunoadsorbent assay, immunofluorescence assay and the like. Detection is convenient, rapid, sensitive and specific. The recombinant antigens of BHV-1 proteins are used in assay compositions in a concentration sufficient to form a detectable complex with the antibodies. BHV-1 antigens can be mixed with or bound to a suitable matrix (support) or carrier, such as a latex particle, plastic microtitration plate or the like. They can also be conjugated with an enzyme, dye, radioisotope or the like, depending upon what immunological method is used. The details of conducting various types of immunoassays is well known in the art and also described in Tyssen, P., LABORATORY TECHNIQUES IN BIOCHEMISTRY AND MOLECULAR BIOLOGY, PRACTICE AND THEORY OF ENZYME IMMUNOASSAYS (eds. R. H. Burton and P. H. van Knippenberg), the disclosures of which are incorporated by reference.

Accordingly, the invention includes a method for determining the absence or presence and/or concentration of antibodies directed against BHV-1 in a sample by employing an immunoassay, the immunoassay characterized by using recombinant antigenic BHV-1 proteins reactive with BHV-1 antibodies as a reagent in the immunoassay, whereby a complex of the BHV-1 antibodies and the recombinant antigenic BHV-1 protein is formed, and determining the absence or presence and/or concentration of such a complex to determine if antibodies directed against such recombinant protein are present in a sample and, if present, to provide a means of determining their concentration.

Analysis of samples from animals can be used to determine if the animal is protected by the vaccine of the invention and has not been exposed to a wild-type BHV-1 strain. Such a vaccinated animal will only have antibodies to the non-deleted genes and will not have antibodies directed against the deleted gene(s).

Described below are examples of the present invention which are provided only for illustrative purposes. The examples are not intended to limit the scope of the present invention in any way, as numerous embodiments within the scope of the claims will be apparent to those of ordinary skill in the art in light of the present disclosure. Those of ordinary skill in the art are presumed to be familiar with (or to have ready access to) the references cited in the application, and the disclosures thereof are incorporated by reference herein.

C. Experimental

EXAMPLES

Example 1

Use of Recombinant BHV-1 Proteins for Diagnostic Purposes

Recombinant BHV-1 gi, gE, gX, $V_{MW65}$, VP4 and VP8 within the present invention are used as antigens in standard immunological assays, ELISA tests, to indicate the presence of antibodies to BHV-1. In this manner, the immunological status of an animal was assessed with respect to present infection or predisposition to BHV-1.

Recombinant gi, gE, gX, $V_{MW65}$, VP4 and VP8 proteins are diluted in sodium carbonate buffer pH 9.6 and used to coat the wells of an ELISA microtitration plate at concentrations ranging from 0.1 to 1 $\mu$g of protein/well. After incubating for a minimum of 1 hour, the plates are washed and dilutions of animal sera are added to the wells in a serial fashion. Processing of the ELISA assay proceeds essentially as described in U.S. Pat. No. 5,151,267 which is incorporated by reference herein in its entirety. Affinity-purified HRPO conjugated anti-bovine IgG was used at a dilution of 1:3000 for detection.

The developed ELISA assay indicated that animals infected by BHV-1 had detectable levels of antisera specific for gI, gi, gE, gX, gIV, dUTPase, $V_{MW65}$, VP4 or VP8 and any one of these recombinant BHV-1 proteins would be suitable for use in the diagnosis of BHV-1 infection.

Example 2

Isolation of the BHV-1 Homolog of the HSV Tegument Gene $V_{MW65}$ (UL48)

The BHV-1 $V_{MW65}$ gene homolog of the HSV $V_{MW65}$ gene was identified by Southern hybridization analyses of the cloned BHV-1 genome using the HSV-1 $V_{MW65}$ (UL48) gene coding sequence as a probe. FIG. 1 is a representation of the BHV-1 genome (Cooper strain) in which the HindIII restriction endonuclease sites are represented as vertical lines. Each of the HindIII fragments (less the terminal fragments) were cloned into the HindIII site of pBR322. The plasmids representing the BHV-1 genomic clone bank were digested with HindIII and run on a 1% agarose gel. The separated DNA fragments were transferred to nitrocellulose, which was probed with a cloned fragment of the HSV-1 genome containing the UL48 gene coding sequence. The HSV DNA probe was labeled with $^{32}P$ by nick-translation. The first probe used was a 1217 bp SalI fragment containing the bulk of the HSV $V_{MW65}$ (UL48) gene coding sequence isolated from the plasmid pMC1 (see Dalrymple et al. (1985) *Nucl. Acid Res.* 13:7865). When used as a probe, it hybridized specifically to the BHV-1 HindIII J fragment represented in the subclone pSD57.

In order to more precisely define the position of the BHV-1 $V_{MW65}$ gene homolog within this 9 kilobase pair HindIII fragment, a detailed restriction endonuclease map of pSD57 was constructed. pSD57 was then digested with an array of restriction endonucleases known to cut within the BHV-1 insert. The fragments were separated on duplicate agarose gels, which were then blotted with nitrocellulose. The transfers were probed individually with amino- or carboxy-terminal specific probes from the HSV-1 $V_{MW65}$ gene (the probes were generated by SalI plus MaeI digestion of pMC1, followed by relevant fragment isolation). Results from these experiments positioned the BHV-1 $V_{MW65}$ tegument gene at the extreme right-hand end of the HindIII J fragment (see FIG. 1). The orientation of the gene was determined using end-specific probes. The gene is transcribed left to right (i.e., towards the center of the BHV-1 genome). In addition, the differential probe hybridization suggested that the tegument gene extends into the adjacent HindIII fragment, HindIII M, present in clone PSD62. From this information subclones were made (from pSD57 and pSD62) of the suspected gene coding region for DNA sequence analyses (see FIG. 1).

DNA sequencing has demonstrated significant predicted amino acid homology between HSV $V_{MW65}$ (UL48) and a large open reading frame in the relevant subclones from pSD57 and pSD62 (FIG. 1). This clearly demonstrates that the BHV-1 $V_{MW65}$ gene homolog has been identified. The BHV-1 $V_{MW65}$ tegument gene is expressed in gene expression systems (e.g., vaccinia, adenovirus or baculovirus) and the recombinant product tested for immunogenicity in animals.

Example 3

In Vitro Characterization of BHV-1 $V_{MW65}$ Homolog

The BHV-1 $V_{MW65}$ gene homolog, VP16, is expressed in high levels by mammalian cells in culture using a vaccinia virus foreign gene expression system. (Elroy-Stein and Moss (1990) *Proc. Natl. Acad. Sci. USA*, 87:6743–6747). To insure authenticity of the cloned BHV-1 $V_{MW65}$ gene homolog product, VP16, monospecific polyclonal antisera against BHV-1 VP16 is made by immunizing rabbits with the recombinant form of the protein made by the vaccinia system. This serum is used in ELISA, immunoprecipitation and/or Western blot analyses of BHV-1 infected cells. These assays establish if antibody to recombinant VP16 specifically binds authentic VP16 produced by BHV-1 infected cells.

In order to determine if BHV-1 VP16 has transactivating activity, the BHV-1 $V_{MW65}$ gene homolog is cloned into a eukaryotic cell expression vector, for example, a vector containing the constitutive SV40 late antigen promoter. This vector is used to co-transfect MDBK cells with naked BHV-1 genomic DNA. VP16 transactivating activity allows efficient production of a large number of virus plaques resulting from genomic DNA transfection in the presence of the $V_{MW65}$ homolog expression vector compared to the production of very few plaques when cells are transfected with BHV-1 DNA alone. This result is expected, since the VP16 protein is required for the efficient initiation of the viral transcriptional cascade which cannot be provided by the naked viral genomic DNA.

Alternatively, the promoter sequence of the BHV-1 IE gene is isolated. A vector containing the IE promoter is constructed which regulates the expression of a reporter gene such as *E. coli* lac Z or chloramphenicol acetyltransferase (CAT). Co-transfection of MDBK cells with the IE promoter/reporter gene vector and BHV-1 VP16 expression vector is carried out. The trans-activating activity of BHV-1 VP16 is determined by the extent of reporter gene expression.

Example 4

Construction of BHV-1 gIII Gene Deletions and Insertions

A functional virus was produced when the glycoprotein gIII gene coding sequence was deleted from BHV-1 according to the methodology described in Liang et al. (1991) *J. Virology* 65:1124–1132. See also Kit et al. (1991) *Vaccine* 9:564–572). Making deletions in this class of genes (i.e., those encoding the viral glycoproteins) was intended to limit the replication efficiency of the virus such that it was rendered safe for administration to cattle as a live vaccine. Surface exposed viral glycoproteins are responsible, either directly or indirectly, for permissive host cell recognition and virus entry, including attachment and penetration. Thus, genetically altering these important virulence factors affects the ability of the virus to replicate in the natural host.

The gIII gene-deleted BHV-1 mutant exhibited a characteristically altered phenotype in vitro. When compared to parental wild-type virus, the mutant exhibited a delay in replication, reduced shedding of virus from infected cells and a reduced efficiency of virus egress but was not sufficiently attenuated to be used as a vaccine.

Example 5

Deletions of Minor Glycoprotein Genes

In addition to generating the gIII gene deletion, partial gene deletions were made in the BHV-1 gi and gX gene homologs. This was accomplished by first mapping the positions of the BHV-1 genes encoding the minor glycoproteins (gX and gi), using the HSV and PRV homologous genes as probes of the BHV-1 genome in Southern blot analyses.

This same procedure was used to map the position of the major glycoprotein genes, namely gI (gB), gIII (gC) and gIV (gD). Using both the HSV and PRV gene homologs, the position of the corresponding BHV-1 genes were found. Mapping experiments showed that the gD gene coding sequence, located within the $U_s$ region (specifically in the HindIII K fragment), is flanked by the gX and gi genes, while the gE gene is distal to the gi gene, its 3' end most probably extending into the HindIII C fragment.

The map position and orientation of all the genes in FIG. 1 shows colinearity between the related herpesviruses [i.e., including BHV-1, HSV-1 and 2, PRV, feline herpesvirus 1 (FHV 1), Marek's disease virus and equine herpesvirus 1 (EHV 1)]. The map positions of the minor glycoprotein genes gE, gX and gi were disclosed by Tim Zamb at the International Bovine Herpesvirus Meeting (1988) and are consistent with the map produced by Wirth et al., Proceedings of the International Herpesvirus Meeting (1991). The HindIII clones described are equivalent to those produced by Mayfield et al. (1983) *J. Virology*, 47:259–264.

A detailed restriction endonuclease map of the BHV-1 HindIII K genomic fragment was generated as shown in FIG. 1. The minor glycoprotein genes, which were targets for deletion, mapped to this fragment. As seen in FIG. 1, a 300 bp Xho I fragment was mapped to the approximate middle of the coding sequence of the gX gene. An insertion vector was constructed in which the 300 bp Xho I subfragment from the HindIII K fragment was replaced by a lac Z expression cassette. This expression cassette consisted of the BHV-1 gIII gene promoter (pgIII) followed by the coding sequence of the lac Z gene which, in turn, was followed by the SV40 polyadenylation signal. The lac Z coding sequence begins with the nucleotides encoding the 10th amino acid of beta-galactosidase. Recombinant BHV-1 with the pgIII:lac Z cassette inserted into the gX gene coding sequence was generated by co-transfecting MDBK cells with the above insertion plasmid and wild-type BHV-1 genomic DNA according to the methodology of Liang et al. (1991) *J. Virology*, 65:1124–1132 and 5553–5557. Recombinant viruses were selected from blue plaques produced by plating viruses arising from the co-transfection on MDBK cells and overlaying with agarose supplemented with Bluogal (a BRL chromogenic substrate for beta-galactosidase). Insertion of the lac Z expression cassette was confirmed by restriction endonuclease analyses of genomic DNA from plaque purified blue viruses.

A vector for insertion of the lac Z reporter gene into the gi gene was constructed in a similar manner. A 300 bp Not I fragment was mapped to the middle of the coding sequence for the gi gene. Since there are several Not I sites in the HindIII K fragment, the 1865 bp Sma I subfragment, containing the coding sequence for the gi gene was subcloned and formed the basis of the gi gene insertion plasmid. The two Not I sites present in the gi gene coding sequence are the only ones present in the Sma I subfragment. The pgIII-lac Z-SV40 poly A cassette was inserted into the Sma I subclone, replacing the 300 bp Not I fragment. In addition to the above single mutants, double mutants were constructed to increase attenuation of the BHV-1 vaccine vector. A gIII:gX gene double mutant was obtained by co-transfecting cells with the gX gene insertion vector and genomic DNA isolated from the gIII gene deleted virus (both described above). The double mutant was confirmed by restriction endonuclease analyses of DNA isolated from blue viruses arising from this co-transfection.

In vitro characterization of the above insertion mutants again demonstrated the profound effect that gene disruption may have on proper virus function. Wild-type (Cooper) and the gene-disrupted viruses were plated on 6-well microtitration plates such that there were approximately 50 plaque forming units per well, and overlayed with 1.25% agarose supplemented with growth media and 2% fetal bovine serum. Following four days growth at 37° C. and 5% $CO_2$, the diameters of 100 plaques for each virus were measured. Plaque size was expressed as a percentage of the mean diameter of the wild-type virus (Cooper strain). gX plaque diameter was 60% of the diameter of the wild-type whereas gE plaques were 40% of the diameter of the wild-type virus plaque size. The gX mutant was produced using an insertion plasmid. There was a lesser, but measurable difference, in the gX (the homolog to PRV gX) gene mutant as well.

This phenotypic difference was also reflected in virus titers. MDBK cells were infected with virus at a multiplicity of infection of one. At regular intervals throughout the infection process, culture media was harvested, clarified by low-speed centrifugation, and virus titers were determined by plaque assay. Results showed that the wild-type Cooper strain could produce >$10^7$ pfu/ml, while gX gene mutant produced $10^7$ pfu/ml.

The effect of two lesions at different genetic loci within the same virus were measured in a single step growth experiment. A $gIII^-$: $gX^-$: lac $Z^+$ mutant was produced using an insertion plasmid. The double deletion mutant was produced by co-transfecting MDBK cells with naked viral genomic DNA from the $gIII^-$ mutant plus the insertion plasmid. The $gIII^-$ BHV-1 mutant is described in Liang et al. (1991) *J. Virol.* 65:1124–1132.

A single-step growth assay was performed for wild type BHV-1 and the $gIII^-$: $gX^-$: lac $Z^+$ mutant viruses as in the preceding paragraph, except that cells rather than growth media were harvested and assayed for the production of virus. At regular intervals throughout the experiment, infected cells were harvested, washed extensively and lysed by successive freeze-thawings. Virus liberated from cells was determined by plaque assays. These results demonstrated that in vitro virus replication efficiency was more severely effected in a double mutant than in either of the corresponding single locus mutants.

The reduced replication efficiency exhibited by the BHV-1 mutants described above was caused by a decrease in (a) virus adsorption to permissive cells; (b) virus penetration following attachment; (c) virus progeny for the $gIII^-$: $gX^-$: $LacZ^+$ double mutant; and (d) efficiency of virus egress from infected cells for the $gIII^-$: $gX^-$: $LacZ^+$ double mutant.

In order to measure wild-type and mutant virus adsorption to permissive cells, MDBK cells in six-well plates were cooled at 4° C. for one hour, and approximately 400 plaque forming units (PFUs)/well of each virus were added and then incubated at 4° C. Viral inoculum was removed from individual wells at 0, 36, 72 , 108, 144 and 180 minutes; the cells were then washed and overlaid with agarose. Plaques were counted four days later. The number of plaques formed following 180-minute incubation at 4° C. was defined as 100% adsorption.

To compare the penetration kinetics of wild-type BHV-1 to a $gX^-$ mutant, MDBK cells in six-well plates were cooled to 4° C., inoculated with 200 PFUs of virus and incubated at 4° C. for one hour. After adsorption, the inocula were removed, and the cells were returned to 37° C. Cells were washed with acid at 10, 20, 30 , 40 and 50 minutes to inactivate unpenetrated virus. Once washed, the cells were overlaid with agarose. The number of viral plaques was counted four days later. The number of plaques formed without acid treatment was designated 100% penetration for purposes of calculating percentages. Analysis of viral penetration by wild-type BHV-1 versus $gX^-$ penetration indicated wild type to have approximately 88% penetration and $gX^-$ approximately 66% penetration after 50 minutes incubation.

The degree of attenuation of each of the described mutant viruses was determined by the methodology of Liang et al. (1992) *Virology* 189:629–639. Briefly, following intranasal administration of the mutant and wild-type viruses, clinical disease symptoms, virus lesions in the upper respiratory tract, virus shed in nasal secretions, BHV-1 antibody titers both to the deleted antigen and to reference BHV-1 antigens, virus neutralization titers in serum, and resistance to a superinfecting virulent challenge virus strain (strain 108) were evaluated. The results indicated that the level of immunity induced was directly related to the degree of attenuation. With the least attenuated mutant ($gIII^-$), some virus shedding and clinical symptoms were observed with subsequent high-level immunity and complete protection from challenge. By way of contrast, the most attenuated mutant ($gX^-$) only provides putative protection.

Example 6

Construction of a Recombinant BHV-1 Virus Lacking the dUTPase Gene

Wild-type BHV-1 was propagated in MDBK cells grown in minimum essential medium (MEM, GIBCO/BRL Laboratories, Grand Island, N.Y.) supplemented with 10% fetal bovine serum (FBS, GIBCO/BRL). Degenerate oligonucleotides used as PCR primers were produced as shown in FIG. 4A. Purified BHV-1 genomic DNA and a plasmid, pSD57, which contains the HindIII J fragment of the BHV-1 genome were used as templates. Prior to the standard PCR procedure, template DNA was prepared manually with one cycle of a primer extension reaction using T7 polymerase and c7-deaz-GTP to replace dGTP. This reaction was carried out using a Pharmacia $T^7$ Sequencing Kit (Pharmacia, Baie d'Urfe, Quebec Canada) according to instructions, except that the chain elongation reaction was performed at 37° C. for 5 minutes. The 5' primer-and 3' primer-based extension reactions were performed sequentially. For the subsequent PCR procedure, each reaction mixture consisted of: 100 ng of the T7 polymerase treated template DNA; 50 pmol of each primer; 200 μmol each of DATP, dGTP, dCTP and dTTP, and; units of *Pyrococus furiosus* (pfu) DNA polymerase (Stratagene, La Jolla, Calif.) in pfu DNA polymerase buffer 1 (Stratagene). The reaction was initiated with a denaturation step at 98° C. for 4 min, followed by 40 cycles of 55° C. for 30 seconds (annealment) −78° C. for 90 seconds (polymerization) −98° C. for 30 seconds (denaturation). Following amplification, the PCR product was digested with EcoRI and HindIII and run on a 1% agarose gel. Following electrophoresis, the appropriate band was isolated and cloned into the EcoRI and HindIII sites of Bluescript II $KS^+$ (Stratagene).

Generation of Recombinant Virus

The transfer vector used for generation of the recombinant virus was constructed as follows. First, pSD57 was digested with NcoI and treated with Mung bean exonuclease. An approximately 0.9 kilobase pair (kbp) blunt ended NcoI fragment, which contains the 5' flanking sequence of the dUTPase gene, was isolated from an agarose gel by standard procedures (Maniatis et al., 1982, supra). polylinker5'gIII (Liang et al. (1991) *J., Virol*. 65:1124–1132), which contains the 5' BHV-1 gIII gene flanking sequence, was digested with Sal I and SmaI (both located upstream of the gIII gene's promoter), and treated with Mung bean exonuclease to blunt the asymmetric ends. The plasmid backbone was isolated from an agarose gel and ligated to the above 0.9 kbp blunt-ended NcoI fragment. The resultant plasmid (p5'DUC) contains the 5' flanking sequence of dUTPase gene immediately upstream of the promoter from the gIII gene. To isolate the dUTPase gene's 3' flanking sequences, pSD57 was digested with DraI and PvuII and a 0.5 kbp fragment (located within the dUTPase coding sequence) was isolated and cloned into the EcoRV site of Bluescript II $KS^+$. The same 0.5 kbp fragment was excised from the Bluescript vector by EcoRI and HindIII digestion and then inserted into the EcoRI and HindIII sites (both located immediately 3' to the coding sequence of the gIII gene) of p5'DUC, resulting in pDUC. The *E. coli* lacZ gene was isolated from pgIII/LacZ (Liang et al. (1992) *Virology* 189:629–639) by NcoI and HindIII digestion and inserted into the NcoI and HindIII sites of pDUC. The resultant plasmid, pDUC/Z, was used as the transfer vector.

To generate recombinant virus, MDBK cells were cotransfected with 10 μg of pDUC/Z (linearized via AseI digestion) and 10 μg of purified BHV-1 genomic DNA using a Bio-Rad gene pulser at 500 μF and 200 V as previously described (Liang et al. (1991) *J. Virol*. 65:1124–1132). The resultant progeny virus was screened for β-galactosidase production by a blue plaque assay.

Blue Plaque Assay

Two types of blue plaque assays were performed. For the initial screening of recombinant virus, the chromogenic substrate, Bluo-gal, was incorporated into agarose overlays of virus infected monolayers (Liang et al., (1992) *Virology* 189:629–639). To assess the purity of the stock of the recombinant viruses isolated in this way, a more sensitive X-gal-based histochemical assay (MacGregor et al. (1987) *Som. Cell and Mol. Gen*. 13:253–265) was employed. In this assay, MDBK cell monolayers containing well separated viral plaques were fixed with 2% paraformaldehyde and 0.2% glutaraldehyde at 4° C. for 5 min, followed by three washes with PBS. The substrate, composed of 1 mg/ml of X-gal in 100 mM sodium phosphate (pH 7.3), 1.3 mM $MgCl_2$, 3 mM $K_3Fe(CN)_6$ 3 mM $K_4Fe(CN)_6$ was added and the monolayers were incubated at 37° C. to permit color development. dUTPase assay.

The dUTPase assay was performed according to Wohlrab et al. (1982) *J. Virol*. 43:935–942. Approximately $2\times10^7$ MDBK cells were infected with each virus at a multiplicity of infection (MOI) of 1. Twenty hours after infection, cytoplasmic and nuclear fractions were collected separately, and suspended in 1 ml and 0.3 ml of the hypotonic solution [20 mM 4-(2-hydroxethyl)-1piperazine ethanesulfonic acid buffer (pH 7.8)-1 mM dithiothreitol-1 mM $MgCl_2$] containing 80 mM potassium acetate], respectively. For each enzyme reaction, 45 μl of cell extract was added to 5 μl of a stock solution containing 100 mM $MgCl_2$, 10 mM dithiothreitol, 10 mM ethylene glycol-bis (β-aminoethyl ether)-N,N,',N',-tetraacetic acid (EGTA), 20 mM ATP and 0.5 mM [3H]-dUTP (2 Ci/mmol; Amersham, Oakville, Ontario, Canada). The reaction was carried out at 4° C. and terminated by addition of 20 μl of 100 mM EDTA and 105 μl of methanol. [3H]-dUMP, produced from the reaction, was separated from [3H]-dUTP by thin layer chromatography on UV-sensitive polyethyleneimine (PEI)-cellulose plates. The production of [3H]-dUMP was determined by scintillation counting of the corresponding spots excised from the PEI-cellulose plates.

Other Methods

Restriction endonuclease mapping and Southern blot analysis were carried out by standard procedures (Maniatis et al., 1982, supra). Sequence determination was performed according to the double-stranded DNA sequencing protocol provided with the Pharmacia T7 Sequencing Kit, substituting dGTP with c7-deaz-GTP. Both strands of DNA were sequenced at least once. Amino acid sequence homology comparisons were analyzed using the CLUSTAL Program (Higgins and Sharp (1988) *Gene* 73:237–244). Identification of the BHV-1 dUTPase Gene by PCR.

The initial approach, which involved probing a plasmid library of the BHV-1 genome (Mayfield et al. (1983) *J. Virol*. 47:259–264) with the HSV-1 dUTPase coding sequence [contained within plasmid pGX63 (Preston and Fisher (1984) *Virol*. 138:58–68)], failed to identify the BHV-1 dUTPase gene. A degenerate primer-based PCR procedure was then pursued. The aim was to first amplify a dUTPase gene fragment from the BHV-1 genome, and then to use the PCR product as a probe to map the dUTPase gene.

The dUTPases of HSV-1, VZV, EBV, *E. coli*, yeast and mammalian cells were previously shown to share five prominent conserved amino acid motifs (McGeoch (1990) *Nuc. Acid Res*. 18:4105–4110; McIntosh et al. (1992) *Proc. Natl. Acad. Sci. USA* 89:8020–8024). Differing from the dUTPases of other organisms, herpesvirus encoded dUTPases have a rearranged order of these motifs, so that motif 3 is followed by motifs 1, 2, 4 and 5, respectively. Based on this, motifs 3 and 1 from HSV 1 and VZV were selected to derive the 5' and 3' degenerate PCR primers, respectively (FIG. 4A). In order to reduce total degeneracy, two sets of primers were synthesized based upon the sequence of motif 3 from HSV-1. All the primers consisted of 20 nucleotides based upon the conserved dUTPase motifs covalently linked at their 5' ends with an 8 nucleotide sequence containing a restriction endonuclease recognition site (EcoRI for the motif 3 primers and HindIII for the motif 1 primers). The genome of BHV-1 is arranged in an inverted orientation relative to the accepted format of depicting the HSV-1 genome (Davison and Wilkie (1983) *J. Gen. Virol*.

64:1927–1942). After correcting for this inversion, the positions of all BHV-1 genes thus far mapped are collinear with their HSV 1 counterparts. Accordingly, it was determined that the gene encoding dUTPase (the HSV-1 UL50 gene homolog) should map to a subregion within the HindIII J fragment of BHV-1 genome. An attempt was then made to amplify a BHV-1 dUTPase gene fragment from both viral genomic DNA and the plasmid, pSD57, which contains the HindIII J fragment. One cycle of a primer extension reaction using T7 polymerase (an enzyme with known high processivity) was carried out in the presence of c7-deaz-GTP. This was followed by the conventional PCR procedure. With this modification, a distinct PCR product of approximately 0.25 kb was obtained. A similar product with much weaker intensity was also amplified from the BHV-1 genomic DNA. The 0.25 kb fragment amplified from pSD57 was isolated and subsequently cloned into Bluescript, and its sequence was determined.

Map and Sequence of the BHV-1 dUTPase Gene

The observation that similar PCR products were amplified from both BHV-1 genomic DNA and pSD57 localized the BHV-1 dUTPase gene within the HindIII J fragment as predicted. To further map its location within the HindIII J fragment, pSD57 was digested with various restriction endonucleases and analyzed by Southern transfer using the PCR product as a probe. Results from these experiments mapped the PCR product to a 1.5 kb XhoI fragment (FIG. 1). Sequence determination of this 1.5 kb XhoI fragment revealed a large, but incomplete open reading frame (ORF), which extended beyond the left boundary of the XhoI fragment. Additional subclones to include the region immediately adjacent to the XhoI fragment were produced from pSD57, and corresponding DNA sequences were determined.

As a result, a 975 bp ORF sufficient to encode a 325 amino acid protein (FIG. 6) was identified. A TATA box, typical of promoter sequences recognized by eukaryotic RNA polymerases was found at 271 bp upstream from the translation initiation codon. The translation initiation codon (A at position +1) is positioned within a favored-context, where an adenine occurs at position −3 and a guanidine at position +4 (Kozak (1984) *Nuc. Acid Res.* 12:857–872). No obvious consensus polyadenylation signal sequence could be identified within the region sequenced at the 3' end of the gene. The coding sequence consisted of 16.2% T, 15.6% A, 37% C and 31.1% G, which is consistent with high GC content of the BHV-1 genome.

The genome location of the ORF was calculated to be between 0.059 and 0.0666 m.u. It has been previously shown that the BHV-1 homolog of the HSV 1 UL47 gene resides between 0.088 and 0.108 m.u. (Carpenter and Misra (1991) *J. Gen. Virol.* 72:3077–3084). As the UL47 gene and the currently identified ORF are transcribed in opposite directions, the distance between these two genes can be estimated to be 0.022 m.u., or about 3 kbp. This approximates the distance of 3984 bp that separates the HSV-1 UL47 and UL50 genes (McGeoch et al. (1988) *J. Gen. Virol.* 69:1531–1574). Therefore, the ORF identified appears to be collinear with the HSV-1 UL50 gene (i.e., the HSV-1 dUTPase gene).

The protein encoded by the BHV-1 ORF has a calculated molecular weight of 34 kilodaltons and an isoelectric point (pI) of 9.07. Its amino acid sequence shares significant homology with dUTPases of HSV-1 (40%), VZV (41.5%) and EBV (35.3%), and in particular it possesses all five conserved amino acid motifs characteristic of all dUTPases identified to date (McGeoch (1990) *Nuc. Acid Res.* 18:4105–4110; McIntosh et al. (1992) *Proc. Natl. Acad. Sci.* 89:8020–8024). Taken together these results indicate that the ORF encodes the BHV-1 dUTPase.

Construction of a dUTPase Gene Deletion Mutant

In order to prove that the identified gene encodes a functional dUTPase, an attempt was made to construct a dUTPase gene deletion mutant, by homologous recombination (Liang et al. (1991) *J. Virol.* 65:1124–1132). The transfer vector, pDUC/Z, was used to generate this mutant and the predicted restriction endonuclease map at the dUTPase gene locus in the mutant virus, vDUC/Z. According to the design of the transfer vector, the genome of the mutant virus should contain a 573 bp NcoI-DraI fragment deletion, including 364 bp of 5' flanking sequence and 209 bp of 5' coding sequence of dUTPase gene. To facilitate screening for the mutant virus, the deleted gene fragment was replaced by a BHV-1 gIII promoter-controlled *E. coli* lacZ gene expression cassette. The recombinant virus was generated by cotransfecting MDBK cells with the transfer vector, pDUC/Z, and naked BHV-1 genomic DNA, and identified by its production of β-galactosidase.

The genomic configuration of the recombinant virus was verified by Southern blot analysis. A probe consisting of the approximately 0.6 kbp NcoI-DraI fragment (deleted in the transfer vector) from of the dUTPase gene locus was used to probe the XhoI digested wt BHV-1 DNA and mutant virus DNA. This probe hybridized to wt BHV-1 DNA but not the genomic DNA of the mutant, indicating that the NcoI-DraI fragment was deleted from the mutant virus. When a 1.5 kbp XhoI fragment isolated from the BHV-1 gIII gene region (which includes both 5' flanking sequences and the gIII gene coding sequence) was used as a probe, it hybridized to a 1.5 kbp fragment from both the wt and the mutant virus. This fragment represents the XhoI fragment at the gIII gene locus. An additional band of about 5.3 kbp in the mutant virus also was found to be recognized by this probe. This is the predicted size of the XhoI fragment, containing the gIII promoter-lacZ gene expression cassette, at the dUTPase gene locus in the mutant virus. The results from the Southern analysis confirmed the expected genomic organization of the mutant virus.

Lack of dUTPase Activity of the Mutant Virus

The virus-encoded dUTPase activity in wt and mutant virus infected cells was examined. The assay was performed on both cytoplasmic and nuclear extracts of virus infected cells. dUTPase activity was determined on the basis of production of dUMP. The wt BHV-1 infected cell lysate (either fraction) had a significantly higher (approximately 3 times higher) dUTPase activity than the mock infected cell lysate, whereas lysates of mutant virus infected cells had activities comparable to the mock infected cell lysates. Therefore, the mutant virus lacked virus-coded dUTPase activity. In wt BHV-1 infected cells, the cytoplasmic extract contains much higher dUTPase activity than the nuclei. This indicates that BHV-1 dUTPase exists mainly in the cytoplasm of infected cells.

Example 7

Identification of the BHV-1 Homolog of the HSV 1 UL49.5 Gene

Further analysis of the sequenced fragment revealed an additional 288 bp ORF, positioned in the strand complementary to the dUTPase coding sequence, and overlapping the 5' end of the dUTPase ORF by 18 codons (FIG. 7). The map position of this newly identified ORF appears to correspond to the HSV-1 UL49.5 gene (Barker and Roizman (1992) *J. Virol.* 66:562–566; Barnett et al. (1992) *J. Gen. Virol.* 73:2167–2171), the VZV UL49.5 gene homolog (ORF9a) and the equine herpesvirus 1 (EHV-1) ORF10 (Barnett et al. (1992) *J. Gen. Virol.* 73:2167–2171). The amino acid sequence deduced from this BHV-1 ORF showed significant homology with the alphaherpesvirus UL49.5 homologs, particularly at the carboxyl-terminal half of the molecule. Further, the four heavily conserved amino acid residues (C, F, Y and V) present in the carboxyl-terminal half of all alphaherpesvirus UL49.5 homologs thus far identified, were also conserved on the BHV-1 sequence. Hydrophobicity analysis of the deduced amino acid sequence of the BHV-1 ORF revealed pronounced hydrophobic domains located at the amino- and carboxyl-terminus of the molecule. The amino-terminal hydrophobic sequence is followed by a putative signal sequence cleavage site between amino acid residues 17 and 18. This profile is highly characteristic of a membrane bound protein, and is consistent with other previously identified UL49.5 gene products. On the bases of these properties, it was determined that this ORF encodes the BHV-1 homolog of HSV UL49.5.

Example 8

Selection of Promoters

The nucleocapsid gene (which encodes VP4) was mapped via the Southern hybridization technique, using the HSV-1 nucleocapsid gene (Davison and Scott (1986) *J. Gen. Virol.* 67:2279–2286) as a probe and partially sequenced. Constructs for the insertion of a reporter gene comprising a truncated form of the BHV-1 gIV gene lacking sequences encoding the glycoprotein anchor under the control of the nucleocapsid gene promoter into the dUTPase locus of BHV-1 are made. The level of gene expression elicited by the nucleocapsid gene promoter, measured by the amount of gIV appearing in the media of recombinant virus infected cells, is compared to the expression achieved by the gIII promoter in an analogous construct. Additional constructs comprising a truncated form of the BHV-1 gIV gene as described above under the control of BHV-1 pVP8, pgIII and pgIV, as well as the HCMV IEP promoter and the PrV IEP promoter are made and the level of gene expression is determined for each of these promoters as described above.

The DNA sequence of the $V_{MW65}$ gene is shown in FIG. 2 and its map location in FIG. 1. The efficacy of this promoter was determined using the truncated gIV gene as a reporter in a fashion identical to analyses of the nucleocapsid and gIII gene promoters.

In addition to direct isolation of promoters from known genes, a promoter trap vector for rescue of random promoter sequences was made based upon inserting restriction endonuclease generated BHV-1 subgenomic DNA fragments into a plasmid containing the gIII gene coding sequence plus its 3' untranslated region. The gIII gene promoter was deleted from the plasmid but it contained BHV-1 genomic DNA that normally resides immediately upstream of this promoter. Genomic DNA fragments produced by digestion with Sau 3A, Sau 96A or Mae III and treated with Klenow enzyme to fill-in asymmetric ends were inserted into the Klenow enzyme treated Nco I site (which contained the gIII gene's initiation codon) of the trap vector. Transforming *E. coli* with this mixed population of plasmids produced clone banks in which the gIII gene's promoter was replaced by random subgenomic fragments of BHV-1 DNA.

These clone banks were used to cotransfect cells in conjunction with genomic DNA isolated from the gIII gene deleted virus. Recombinant viruses capable of expressing gIII were then isolated by the black plaque assay, described in Liang et al. (1991) *J. Virology* 65:5553–5557. The gIII expressing viruses were produced by recombination events between genomic DNA from the gIII- mutant virus and plasmids that carry BHV-1 DNA fragment inserts at the Nco I cloning site capable of driving the expression of the gIII gene. The random promoter fragments were removed from the trap vector by Nco I digestion, since this site can be reconstructed by the fragment cloning regime described above. Promoter strength and timing of expression of these random promoters is assessed by using them to drive the expression of a reporter gene inserted into BHV-1 such as the truncated gIV gene construct. The map position of the relevant random promoters is established by Southern analyses using the promoter fragment as a probe of the BHV-1 genomic clones. At least three BHV-1 segments that cause high-level expression of the gIII gene are isolated.

Example 9

Foreign Gene Expression

Initially, the IL-2 gene is cloned at the BHV-1 gIII gene locus using the resident gIII gene promoter to drive its expression using the co-transfection techniques of Example 7. First, gIII negative recombinant viruses are isolated using gIII reactive antibodies in a black plaque assay. Production of IL-2 by the recombinant virus is determined using a IL-2-dependent cell line. Lawman et al., *Virol. Immunol.* 1:165 (1987/88).

Example 10

Expression of PRV gIII

The pseudorabies virus (PRV) gIII glycoprotein gene (Liang et al. (1991) *J. Virology*, 65:5553–5557) was also inserted and expressed at the BHV-1 gIII locus under the control of the BHV-1 gIII gene promoter. PRV gIII was produced at levels equalling the amount of BHV-1 gIII produced by wild-type virus. The conformation of recombinant PRV gIII was indistinguishable from authentic PRV gIII as demonstrated by its proper functioning in the virus replication process of the PRV $gIII^+$ mutant and in antibody responses to it, for example, monoclonal antibodies that neutralize PRV infectivity and specifically recognize PRV gIII also neutralized infectivity of the BHV-1 mutant expressing PRV gIII.

Example 11

Expression of Lkt A

The leukotoxin gene (Lkt A) from *Pasteurella haemolytica*, was also inserted and expressed at the BHV-1 gIII locus under the control of the BHV-1 gIII gene promoter. The lkt A gene construct used in the production of the recombinant BHV-1 was identical to the one currently employed in the production of commercial *P. haemolytica* vaccine. The product was recognized by antiserum produced to leukotoxin.

Example 12

Mapping and DNA Sequencing of BHV-1 $V_{MW65}$ Gene Homolog

The HSV-1 $V_{MW65}$ gene was used as a probe in a Southern blot analysis of the BHV-1 genomic clones to map the position of its BHV-1 gene homolog. The map location of the BHV-1 $V_{MW65}$ gene homolog is co-linear with the $V_{MW65}$ gene in the HSV-1 genome. The BHV-1 DNA at this region was sequenced revealing a single open reading frame with a coding capacity for 505 amino acids. The amino acid sequence translated from this open reading frame shares 30% homology with the amino acid sequence of the HSV-1 $V_{MW65}$ gene product and 37.1% homology with the VZV homolog.

Example 13

Construction of a BHV-1 Mutant Virus Lacking VP16 Transactivating Activity

The BHV-1 $V_{MW65}$ gene homolog product, VP16, is expected to function like its HSV-1 homolog and, therefore, a nonspecific alteration of this protein is likely to be lethal to the virus. Thus, in order to mutate this protein, it is necessary to first define the structure responsible for its transactivating activity. A set of BHV-1 $V_{MW65}$ gene homolog expression vectors is constructed such that each vector contains a different in-frame linker insertion in the $V_{MW65}$ gene homolog coding sequence. Such in-frame linker insertions do not disrupt the overall protein structure but, once introduced into the correct location, can inactivate the protein's trans-activating activity. Based on the information used to characterize this domain in HSV $V_{MW65}$, the linker insertions are focused on the carboxyl-terminal half of the BHV-1 $V_{MW65}$ molecule. These vectors are tested in transactivation assay systems according to the methodology of Example 11. The domain in the $V_{MW65}$ sequence responsible for transactivation is identified by inserting linkers in the domain and identifying that portion of the domain wherein linker insertion eliminates transactivation. This same mutated $V_{MW65}$ sequence is used to construct a transfer vector for generating a recombinant virus with a $V_{MW65}$ mutation. The same linker is radiolabeled and used as a probe for screening and isolating the desired recombinant virus.

Example 14

Evaluation of Relative Promoter Strengths

Construction of transfer vector. Plasmid po126 (Robbins et al. (1986) *J. Virol.* 58:339–377) was cut with NarI, the resulting ends were repaired with T4 polymerase, and the plasmid was then cut with PvuII. After agarose gel electrophoresis, the plasmid backbone was isolated from the gel and ligated to a 2.4 kb blunt end-repaired NcoI fragment of pSD57 to create plasmid tUL50. Plasmid tUL50 was used for the insertion of the LacZ gene under the transcriptional control of different promoter elements into the DUTPase locus.

Construction of LacZ Expression Cassettes (a) Plasmid tUL50/VP8Lac: First, a 600 bp HindIII-NcoI fragment from pSD62 and a 3.3 kb NcoI-HindIII fragment from pgIII/LacZ, which contains the LacZ gene followed by the SV40 polyadenylation signal, were ligated with HindIII-digested SL301, creating plasmid SLvp8/LacZ. SLvp8/LacZ was digested with HindIII and the large fragment, which contained the LacZ gene flanked on the 5' end by the vp8 promoter and on the 3' end by the SV40 polyA signal, was isolated, blunt end repaired, and ligated to XhoI digested, T4 polymerase treated tUL50.

(b) Plasmid tUL50/gCLac: Plasmid tUL50/gCLac was constructed by ligating the blunt end-repaired SphI-HindIII fragment of pgIII/LacZ with blunt end repaired, XhoI digested tUL50.

(c) Plasmid tUL50/IELac: First, the 800 bp HindIII-NcoI fragment (containing PRV IE gene promoter) from psy742 and the 3.3 kb NcoI-HindIII fragment from pgIII/LacZ were ligated with HindIII-digested SL301 creating plasmid SL/IELac. This plasmid was digested with HindIII and the large fragment was isolated, blunt end-repaired and ligated to XhoI digested, T4 polymerase treated tUL50.

d) Plasmid tUL50/gIVLac: Plasmid pGIV$5^-3^-$ was digested with NcoI and HindIII. The vector backbone was isolated from an agarose gel and ligated to the 3.3 kb NcoI-HindIII fragment of pgIII/LacZ to create plasmid gIV/Lac. This plasmid was digested with XhoI and HindIII and the large fragment was isolated, blunt end repaired and ligated to XhoI digested, T4 polymerase treated tUL50.

Construction of Recombinant Viruses. MDBK cells were cotransfected with 10 ug of purified BHV-1 genomic DNA and 10 ug of linearized plasmid DNA using a Bio-Rad gene pulser at 500 uF and 200 volts. The recombinant viruses were selected by a blue plaque assay by incorporating cromogenic substrate Bluo-gal (Gibco BRL, Gaithersburg, Md.) in the agarose overlays of virus infected cells.

β-galactosidase activity. Monolayers of MDBK cells in six well plates were infected with the individual recombinant viruses or wild type BHV-1 at a multiplicity of 5 pfu/cell. After 24 hrs of infection the cells were detached with a cell scraper in 1 ml of PBS. After centrifugation for 5 min at 3500 rpm, the cell pellet was resuspended in 100 ul of 0.1M Tris-HCl, pH 7.8, 0.5% Triton X-100 and lysed for 15 min at 37° C. The tubes were centrifuged for 10 min at 15,000 rpm and the supernatant was processed further as described (Bignon et al. (1993) *BioTechniques* 15:243–245). Briefly, 4 μl of each supernatant was loaded individually in wells of 96 well plates. Next, 180 μl of PBS containing 0.36% (vol./vol.) β-mercaptoethanol and 0.7 mg/ml of o-nitro-phenyl β-D-galactopyranoside was added to each well using a multichannel pipet. The contents of the wells were mixed by gentle shaking and the plate was sealed with a plastic sheet and incubated at 37° C. for 15 minutes. The optical density was measured at 420-nm wavelength.

The results (FIG. 10) indicate that the LacZ gene expression was greater when the gene was driven by the vp8 promoter than by the gIII, gIV or IE promoters.

Example 15

The Bovine Herpesvirus 1 Homolog of Herpes Simplex Virus UL49 is Not Essential for Virus Growth in Cell Culture The virions of alphaherpesviruses contain a number of tegument proteins situated between the nucleocapsid and envelope (Roizman and Sears, Herpes simplex viruses and their replication (1990), pp. 1795–1841, In B. N. Fields, D. M. Knipe, et al. (ed), *Virology*, 2nd ed. Raven Press, Ltd., New York). These tegument proteins serve at least two major functions: serving as virion structural components and participating in regulating viral gene expression.

The herpes simplex virus type 1 (HSV 1) major tegument protein, α-transinducing factor (α-TIF, vp16 or Vmw65), has been most extensively characterized with respect to gene regulation. α-TIF forms a complex with cellular transcription factors, including Oct-1, by which it interacts with a consensus sequence in proximity to the promoters of viral immediate-early (IE) genes and regulates the expression of the IE genes (Doging and O'Hare (1989) *Virology* 173:363–367). In the normal HSV 1 replication cycle, α-TIF-dependent IE gene activation constitutes the first step of viral gene expression. Mutant virus lacking α-TIF exhibits significantly impaired infectivity, establishing infection only at a high multiplicity of infection (m.o.i) and is avirulent in vivo (Ace et al. (1989) *J. Viol.* 63:2260–2269).

HSV 1 α-TIF is encoded by the UL48 gene. In the viral genome, the Ul48 is surrounded by three additional tegument protein genes, UL46, UL47, and UL49. The UL46 and UL47 gene products appear to be involved in modulating the α-TIF-dependent transcription process (McKnight et al. (1986) *Cancer Cells* 4:163–1734; McKnight et al. (1987) *J. Virol.* 61:992–1001). UL46 and UL47 genes are nonessential for virus growth in culture; nevertheless, mutants with a deletion of either gene exhibit reduced replication efficiency (Zhang et al. (1991) *J. Virol.* 65:829–841). The UL49 gene has been shown to encode the tegument protein vp22 (Elliott and Meredith (1992) *J. Gen Virol.* 73:723–726). vp22 is highly phosphorylated and appears to associate with the nuclear matrix during virus replication (Elliott and Meredith (1992) *J. Gen Virol.* 73:723–726; Pinard et al. (1987) *J. Gen*

*Virol*. 68:727–735), implying its involvement in gene regulation. However, the actual function of UL49 gene product is not known, and it is likewise not known whether it is essential for virus growth.

Bovine herpesvirus 1 (BHV 1), a member of alphaherpesviridae subfamily, is an important pathogen in cattle (Gibbs and Rweyemamu (1977) *Vet. Bull*. 47:317–343). The virion of BHV 1 contains 25 to 33 proteins (Carpenter and Misra (1991) *J. Gen. Virol*. 72:3077–3084; Pastoret et al. (1980) *Vet. Microbiol*. 5:187–192). The most abundant virion protein, vp8, has been identified as the product of a gene homologous to HSV 1 UL47 (Misra et al. (1981) *J. Virol*. 40:367–378). More recently, the UL48 homolog of BHV 1 has also been mapped and sequenced (Carpenter and Misra (1992) *Gene* 119, 259–263; Liang et al., unpublished results). The genomic locations of both BHV 1 UL47 and UL48 homologs are colinear with their HSV 1 counterparts. Interestly, neither the BHV 1 UL47 nor the UL48 gene products contains the acidic domain present in HSV 1 α-TIF that is responsible for the transinducting activity of HSV 1 α-TIF.

Using a probe derived from the coding sequence of HSV 1 UL48 gene, the BHV 1 (Cooper strain) UL48 homolog gene was mapped and subsequently sequenced (Liang et al., unpublished). In addition, by using a degenerate oligonucleotide-based polymerase chain reaction procedure, we identified that the UL50 homolog gene encoding BHV 1 deoxyuridine triphosphatase (dUTPase; Liang et al. (1993) *Virology* 195:42–50). Based on the genomic organization of HSV 1 (McGeoch et al. (1988) *J. Gen Virol*. 69:1531–1574), it was possible that BHV 1 UL49 homolog was located between the UL48 homolog and dUTPase genes.

To identify the UL49 homolog gene, the BHV 1 genomic sequence at the region between the UL48 homolog and dUTPase genes was determined. As a result, a 774-bp open reading frame (ORF) was found which is sufficient to encode a 258 amino acids (FIG. 11). The UL49 homolog ORF is colinear with the genomic location of HSV UL49. The DNA sequence of the 3' portion of the UL49 homolog ORF is consistent with the partial sequence recently reported by Carpenter and Misra ((1992) *Gene* 119:259–263). A putative TATA box, typical of a promoter sequence recognized by eukaryotic RNA polymerase, was found at 86 bp upstream of the ORF, which is preceded by a putative G-C rich sequence. The translation initiation codon (A at position +1) is positioned within a favoured context, in which a guanidine occurs at position −3 and position +4 (Kozak (1984) *Nucleic Acids Res*. 12:857–872). In addition, a typical polyadenylation signal sequence, AATAAA (Birnstiel and Busslinger (1985) *Cell* 41:349–359), is found 64 bp after the translation termination codon. The coding sequence consists of 14.1% A, 35.8% C, 15.5% T and 34.6% G.

The protein encoded by the BHV 1 ORF has a calculated molecular weight of 27 kD and an isoelectric point (pI) of 10.379 and contains three potential phosphorylation signals at residues 8, 33, and 200, respectively. Its amino acid sequences shares significant homology (30.5%) with the UL49 product of HSV 1 and the homolog of varicella-zoster virus (VZV, FIG. 12). These features together strongly suggest the ORF is the BHV 1 homolog of the HSV 1 UL49 gene.

In order to test whether the UL49 homolog is essential for virus growth, as well as to facilitate characterization of the UL49 homolog gene, a UL49 homolog gene deletion mutant was generated by homologous recombination (Liang et al. (1991) *J. Virol*. 65:1124–1132). FIG. 13 shows the schematic representation of the transfer vector, pdUL49Z, used to generate this mutant and the predicted restriction endonuclease map at the UL49 homolog gene locus in the mutant virus, vdUL49Z. According to the design of the transfer vector, the genome of the resultant mutant virus should contain a 280-bp NcoI-XhoI fragment deletion at the 5' end of the coding sequence.

To facilitate screening for the mutant virus, the deleted gene fragment was replaced by a BHV 1 gIII promoter-controlled *E. Coli* lacZ gene expression cassette. The recombinant virus was generated by cotransfecting Madin Darby bovin kidney (MDBK) cells with the transfer vector, pdUL49Z, and naked BHV 1 genomic DNA. Virus resulting from transfection was screened for β-galactosidase expression by a blue plaque assay (Liang et al. (1993) *Virology* 195:42–50). From one of the initial blue plaques, a mutant virus was isolated, which after two additional plaque purification steps was used for subsequent studies. This virus was designated as vdUL49Z.

The genomic configuration of vdUL49Z was verified by Southern blot analysis. The cellular DNA from the wt BHV 1 or from cells infected with mutant was isolated at 10 h postinfection according to Maniatis et al. ((1982) MOLECULAR CLONING: A LABORATORY MANUAL, Cold Spring Harbor Laboratory, Cold Spring Harbor, N.Y.), digested with AseI and NcoI, separated on a 1% agarose gel, transferred to a nitrocellulose filter, and probed with a 1.6 kb AflII-AseI fragment (see FIG. 13). As expected, a 0.9 kb and 0.5 kb hybridizing fragments were detected in the Southern blot of the wt BHV 1 infected cells; whereas a 4 kb and a 1 kb hybridizing fragment could be detected in the blot of the mutant virus infected cells (FIG. 14).

To further ascertain whether the gene was functional, the UL49 homolog gene transcripts was examined in both the wt BHV 1 and total cytoplasmic RNA from cells infected with the mutant virus was analyzed by Northern blotting. When probed with the NcoI-XhoI fragment located at the 5' end of the UL49 homolog gene coding sequence, two distinct bands were revealed, one about 1.2 kb and the other 0.9 kb in the wt BHV 1 infected cells, whereas both bands were absent, as expected, in either the mock infected cells or in the mutant infected cells (left panel of FIG. 15). According to the sequence, the putative TATA box and poly-A signal sequences of the UL49 homolog gene are 936 bp apart, which is consistent with the size of the smaller transcripts detected. This strongly suggests that the 0.9 kb transcripts are coded for by the UL49 homolog gene.

A 288-bp BHV 1 UL49.5 gene ORF which overlaps with, but in an opposite direction to, the dUTPase gene (UL50 homolog), has recently been identified (Liang et al. (1993) *Virology* 195:42–50). When arranged together with the sequence of the UL49 homolog gene, the UL49.5 homolog gene was found to be 86 bp upstream of the UL49 homolog gene ORF.

It was possible that the 1.2 kb transcripts are transcribed from the UL49.5 gene promoter but coterminate with the UL49 gene transcripts. To evaluate this possibility, a 503 bp MaeIII—MaeIII fragment located at 102 bp upstream of the UL49 homolog ORF was used as a probe to detect the viral transcripts on a Northern blot. Total cytoplasmic RNA in the virus infected cells was isolated at 10 h postinfection according to a method described by Kowlaski and Denhardt ((1989) *Mol. Cell. Biol*. 9:1946–1957). 10 Mg of RNA per sample was separated on a 1.2% argarose-formaldehyde gel, transferred to nitrocellulose paper and probed with a 280 bp NcoI-XhoI fragment at the 5' end of UL49 homolog coding sequence (left panel), or with a 530 bp MaeIII—MaeIII fragment located 102 bp upstream of the UL49 homolog gene (right panel). The molecular size was determined by comparison with a RNA ladder (GIBCO/BRL Canada, Burlington, Ontario, Canada) run in parallel with the testing samples. The probe detected only the 1.2 kb transcripts in the wt virus-infected cells (right panel of FIG. 15). The result therefore supports the prediction that the transcripts of UL49 and UL49.5 homolog genes coterminate. It should be noted that the transcripts of HSV 1 UL49 and UL49.5 also coterminate (Hall et al. (1982) *J. Viol.* 43:594–607).

To assess the effect of UL49 homolog gene deletion on replication of the virus in cell culture, the mutant virus was compared with wt BHV 1 in a single step growth curve experiment. Subconfluent MDBK cells grown in 12 well culture places were infected with either the wt BHV 1 or the mutant at an m.o.i. of 4. At indicated times post-infection, the infected cultures were collected. Samples were subjected to three freeze-thaw cycles to release the cellular virus and then titrated on MDBK cells. As shown in FIG. 16 (which represents the means of duplicate samples) the mutant virus showed a reduced yield comparing with the wt BHV 1. Thus, the deletion of the UL49 homolog gene resulted in a reduction of the virus replication in the cell culture.

In summary, the nucleotide sequence of bovine herpesvirus 1 (BHV 1) genome at a region between the previously identified UL48 and UL50 homolog genes of herpes simplex virus was determined, revealing an open reading frame of 774 base pairs capable of encoding 258 amino acids. The deduced amino acid sequence of the open reading frame shares significant homology with the herpes simplex virus type 1 UL49 gene product and the UL49 homolog of varicella-zoster virus, suggesting that this open reading frame is the BHV 1 homolog of HSV UL49. Northern blot analysis using a probe derived from the BHV 1 UL49 homolog gene detected two transcripts of 0.9 and 1.2 kilobase pairs in wild type BHV 1 infected cells. Further analysis showed that the two transcripts coterminate and correspond to that derived from the UL49 homolog gene and that of the previously identified UL49.5 gene, respectively. Based on these information, we constructed a BHV 1 mutant, in which a part of the UL49 gene coding sequence was replaced by a BHV 1 gIII promoter-*E.coli* LacZ gene expression cassette. Comparing the wild type BHV 1, the mutant virus showed a reduced replication efficiency in vitro. The generation of the UL49 deletion mutant indicates that the BHV 1 UL49 homolog is not essential for the virus growth in cell culture.

The UL49 homolog mutant is a valuable tool to further study the function of UL49 gene product with respect to BHV 1 IE gene expression. Further, the mutant virus can be tested in cattle, the natural host of BHV 1, to determine role of the UL49 homolog in viral pathogenesis.

While the present invention has been illustrated above by certain specific embodiments, it is not intended that the specific examples should limit the scope of the invention as described in the appended claims.

We claim:

1. An immunogenic composition comprising:

(a) a pharmaceutically acceptable vehicle; and (b) a live attenuated bovine herpesvirus 1 (BHV-1) wherein at least one essential gene of wild-type BHV-1 is mutated such that mutation of the at least one essential gene results in a reduction of virulence of the virus.

2. An immunogenic composition comprising:

(a) a pharmaceutically acceptable vehicle; and (b) a live attenuated bovine herpesvirus 1 (BHV-1) wherein (i) at least one gene of wild-type BHV-1 that is not essential for viral growth in cell culture is deleted, and (ii) at least one essential gene of wild-type BHV-1 is mutated such that mutation of the at least one essential gene results in a reduction of virulence of the virus.

3. The immunogenic composition of claim 2 wherein the at least one non-essential gene encodes a protein of nucleic acid metabolism or an enzyme of nucleic acid metabolism.

4. The immunogenic composition of claim 2 wherein the at least one non-essential gene is selected from the group consisting of gE, gX, gi, dUTPase, gII, gIII, the Us4 homologue and the Us5 homologue.

5. The immunogenic composition of claim 2 wherein the at least one essential gene is selected from the group consisting of VP4, VP8, $V_{MW65}$, gI and gIV.

6. A method of treating or preventing BHV-1 infection in a bovine host comprising administering to said bovine host a therapeutically effective amount of the imnmunogenic composition of claim 2.

7. An immunogenic composition according to claim 2, wherein:

(a) said at least one non-essential gene of wild-type BHV-1 is replaced with a replacement gene selected from the group consisting of a foreign gene, a gene encoding a BHV-1 immunogen, and a mutant analog of a gene encoding a BHV-1 inmmunogen, wherein said mutant analog replacement gene encodes a BHV-1 immunogen; and (b) the replacement gene is under the control of a promoter.

8. The immunogenic composition of claim 7 wherein the promoter is a strong promoter.

9. The immunogenic composition of claim 7 wherein the promoter is a viral promoter.

10. The immunogenic composition of claim 9 wherein the promoter is selected from the group consisting of adenovirus major late promoter, bacteriophage T7 promoter, cytomegalovirus immediate early alpha promoter and cytomegalovirus beta promoter.

11. The immunogenic composition of claim 9 wherein the promoter is a bovine herpesvirus type 1 (BHV-1) promoter.

12. The immunogenic composition of claim 11 wherein the BHV-1 promoter is selected from the group consisting of pgI, pgIII, pgIV, pVP4, pVP8, $pV_{MW65}$ and pdUTPase.

13. The immunogenic composition of claim 11 wherein a plurality of non-essential genes are deleted and the deleted genes are replaced with a plurality of replacement genes and wherein each replacement gene is under the control of a BHV-1 promoter and further wherein the essential BHV-1 mutated gene is $V_{MW65}$.

14. The immunogenic composition of claim 13 wherein the deleted non-essential genes are selected from the group consisting of genes encoding UL49h, dUTPase gE, gX, and gi.

15. The immunogenic composition of claim 13 wherein the promoters are selected from the group consisting of pgI, pgIII, pgIV, pVP4, pVP8, $pV_{MW65}$ and pdUTPase.

16. The immunogenic composition of claim 13 wherein the replacement gene is a mutant analog of a gene encoding a BHV-1 immunogen, and wherein said mutant analog replacement gene encodes a BHV-1 immunogen.

17. The immunogenic composition of claim 16 wherein the immunogen is secreted gIV.

18. The immunogenic composition of claim 7 wherein the promoter is a non-viral promoter.

19. The immunogenic composition of claim 18 wherein the promoter is bovine heat shock 70A promoter.

20. The immunogenic composition of claim 19 wherein the replacement gene encodes an immunogen of a bacterial pathogen of cattle.

21. The immunogenic composition of claim 19 wherein the replacement gene encodes an immunogen of a viral pathogen of cattle.

22. The immunogenic composition of claim 19 wherein the replacement gene is a mutant analog of a gene encoding a BHV-1 immunogen, and wherein said mutant analog replacement gene encodes a BHV-1 immunogen.

23. The immunogenic composition of claim 7 wherein the deleted non-essential gene is selected from the group consisting of UL49h, dUTPase and gX, and further wherein the deleted gene is replaced with a replacement gene, wherein the replacement gene is under the control of an endogenous promoter selected from the group consisting of pgI, pgIII, pgIV, pVP4, pVP8, $PV_{MW65}$ and pdUTPase.

24. The immunogenic composition of claim 7 wherein the deleted non-essential gene is gE and the deleted gene is replaced with a replacement gene, wherein the replacement gene is under the control of the gIII promoter.

25. The immunogenic composition of claim 7 wherein the deleted gene is gi and the replacement gene is under the control of the VP8 promoter.

26. The immunogenic composition of claim 7 wherein (a) gE and gX genes are deleted;

(b) a first replacement gene comprising a gene encoding interleukin-2 (IL-2) is inserted at the gE locus; and (c) a second replacement gene comprising a second foreign gene is inserted at the gX locus under the control of the BHV-1 $V_{MW65}$ promoter.

27. The immunogenic composition of claim 26 wherein the second replacement gene encodes an immunogen of a bacterial pathogen of cattle.

28. The immunogenic composition of claim 27 wherein the immunogen is selected from the group consisting of *Pasteurella haemolytica* leukotoxin A, *P. haemolytica* leukotoxin B, *P. haemolytica* plasmin receptor and *Hemophilus somnus* lipopolyprotein B.

29. The immunogenic composition of claim 26 wherein the second replacement gene encodes an immunogen of a viral pathogen of cattle.

30. The immunogenic composition of claim 29 wherein the immunogen is selected from the group consisting of bovine viral diarrhoea virus (BVDV) glycoprotein (gp) 53, BVDV gp47, BVDV gp25, bovine respiratory syncytial virus (BRSV) F, BRSV G, parainfluenzae virus type 3 (PV3) F, PV3 HN, bovine coronavirus (BCV) S, BCV HE, bovine rotavirus (BRV) proteins VP4, BRV VP6 and BRV VP7.

31. The immunogenic composition of claim 7 wherein a plurality of non-essential genes are deleted and the deleted genes are replaced with a plurality of replacement genes comprising genes encoding inmmunogens of bacterial and viral pathogens of cattle and wherein each of the replacement genes is under the control of a promoter.

32. The immunogenic composition of claim 31 wherein at least one promoter is a non-viral promoter.

33. The immunogenic composition of claim 31 wherein at least one promoter is a viral promoter.

34. The immunogenic composition of claim 31 wherein at least one promoter is a BHV-1 promoter.

35. The immunogenic composition of claim 7 wherein the replacement gene is a mutant analog of a gene encoding a BHV-1 inmmunogen, and wherein said mutant analog replacement gene encodes a BHV-1 immunogen.

36. The immunogenic composition of claim 35 wherein the mutant analog is of the gene encoding secreted gIV.

37. The immunogenic composition of claim 35 wherein the promoter is a BHV-1 promoter.

38. The immunogenic composition of claim 7 wherein the deleted non-essential gene is selected from the group consisting of genes encoding UL49h, dUTPase, gE, gX, and gi, and the replacement gene is under the control of a BHV-1 promoter selected from the group consisting of pgI, pgIII, pgIV, pVP4, pVP8, $PV_{MW65}$ and pdUTPase; and further wherein the essential BHV-1 mutated gene is $V_{MW65}$.

39. The immunogenic composition of claim 38 wherein the replacement gene encodes an immunogen of a bacterial pathogen of cattle.

40. The immunogenic composition of claim 38 wherein the replacement gene encodes an immunogen of a viral pathogen of cattle.

41. The immunogenic composition of claim 7 wherein two non-essential genes are deleted and the first replacement gene is a gene encoding a cytokine that modulates an immune response in cattle and the second replacement gene is a gene encoding a immunogen from a bacterial or viral pathogen of cattle.

42. The immunogenic composition of claim 41 wherein the cytokine is selected from the group consisting of interleukin-1α, interleukin-1β, interleukin-2, interleukin-4, granulocyte-macrophage colony stimulating factor (GM-CSF) and interferon-gamma (INF-γ).

43. The immunogenic composition of claim 41 wherein the immunogen of a bacterial pathogen is selected from the group consisting of *Pasteurella haemolytica* leukotoxin A, *P. haemolytica* leukotoxin B, *P. haemolytica* plasmin receptor and *Hemophilus somnus* lipopolyprotein B.

44. The immunogenic composition of claim 41 wherein the immunogen of a viral pathogen is selected from the group consisting of bovine viral diarrhoea virus (BVDV) glycoprotein (gp) 53, BVDV gp47, BVDV gp25, bovine respiratory syncytial virus (BRSV) F, BRSV G, parainfluenzae virus type 3 (PV3) F, PV3 HN, bovine coronavirus (BCV) S, BCV HE, bovine rotavirus (BRV) proteins VP4, BRV VP6 and BRV VP7.

45. The immunogenic composition of claim 7 wherein a plurality of non-essential genes are deleted and are replaced by a plurality of replacement genes comprising genes encoding immunogens of pathogens of cattle selected from the group consisting of bacterial pathogens and viral pathogens.

46. The immunogenic composition of claim 45 wherein each of the replacement genes are under the control of a promoter.

* * * * *

UNITED STATES PATENT AND TRADEMARK OFFICE

CERTIFICATE OF CORRECTION

PATENT NO. : 6,086,902

DATED : July 11, 2000

INVENTOR(S) : Timothy ZAMB et al.

It is certified that error appears in the above-identified patent and that said Letters Patent is hereby corrected as shown below:

In claim 6, at column 63, line 55 please replace "imnmunogenic" with --immunogenic--;

In claim 7, at column 63, line 65 please replace "inmmunogen" with --immunogen--;

In claim 23, at column 65, line 9 please replace "$PV_{mw65}$" with --$pV_{mw65}$--;

In claim31, at column 65, line 45 please replace "inmmunogens" with --immunogens--;

In claim 35, at column 66, line 3 please replace "inmmunogen" with --immunogen--;

In claim 38, at column 66, line 14 please replace "$PV_{mw65}$" with --$pV_{mw65}$--.

Signed and Sealed this

Tenth Day of April, 2001

Attest:

Nicholas P. Godici

NICHOLAS P. GODICI

*Attesting Officer* *Acting Director of the United States Patent and Trademark Office*

SEQUENCE LISTING

```
(1) GENERAL INFORMATION:

   (iii) NUMBER OF SEQUENCES: 21


(2) INFORMATION FOR SEQ ID NO:1:

     (i) SEQUENCE CHARACTERISTICS:
          (A) LENGTH: 1788 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 97..1611

        (xi) SEQUENCE DESCRIPTION: SEQ ID NO:1:

CGAGCGGCGC GCGGCTTAAG CAGCGCGCTG CTGTGCTAGT ATGAAAATAA ACGCTTGTTA     60

ATTAAACACA CCAAGCCGAG TTGCGTTGTC TTTGGG ATG AGC GGG CGC ATA AAA     114
                                        Met Ser Gly Arg Ile Lys
                                          1               5

ACC GCG GGC CGC GCG CTC GCC AGT CAG TGC GGC GGT GCT GCG GCG GCA     162
Thr Ala Gly Arg Ala Leu Ala Ser Gln Cys Gly Gly Ala Ala Ala Ala
            10                  15                  20

ACC ATG GAC CCG TAC GAC GCC ATT GAA GCG TTC GAT GAC TCC CTG CTC     210
Thr Met Asp Pro Tyr Asp Ala Ile Glu Ala Phe Asp Asp Ser Leu Leu
        25                  30                  35

GGG TCG CCG CTC GCG GCG GGG CCG CTT TAT GAC GGC CCG TCC CCC GCG     258
Gly Ser Pro Leu Ala Ala Gly Pro Leu Tyr Asp Gly Pro Ser Pro Ala
    40                  45                  50

CGG TTC GCG CTG CCG CCC CCG CGC CCG GCT CCC CTG GCC GCG TTG CTG     306
Arg Phe Ala Leu Pro Pro Pro Arg Pro Ala Pro Leu Ala Ala Leu Leu
 55                  60                  65                  70
```

-continued

```
GAG CGA ATG CAG GCC GAG CTG GGC TTC CCC GAC GGC CCC GCG CTG CTG      354
Glu Arg Met Gln Ala Glu Leu Gly Phe Pro Asp Gly Pro Ala Leu Leu
                 75                  80                  85

CGG GCC ATG GAG CGG TGG AAC GAG GAC TTA TTC TCG TGT CTG CCG ACC      402
Arg Ala Met Glu Arg Trp Asn Glu Asp Leu Phe Ser Cys Leu Pro Thr
            90                  95                 100

AAC GCA GAC CTG TAC GCA GAC GCC GCG CTG CTC TCG GCA GAC GCA GAC      450
Asn Ala Asp Leu Tyr Ala Asp Ala Ala Leu Leu Ser Ala Asp Ala Asp
       105                 110                 115

GCG GTA GTG GGC GCC ATG TAC CTA GCG GTG CCT GGG GAC GCG GAG CGC      498
Ala Val Val Gly Ala Met Tyr Leu Ala Val Pro Gly Asp Ala Glu Arg
   120                 125                 130

TTG GAC TTG AAC GCG CAC GCG AAC CAG CCG CTT CCC GCA CCG CCG GCC      546
Leu Asp Leu Asn Ala His Ala Asn Gln Pro Leu Pro Ala Pro Pro Ala
135                 140                 145                 150

TCG GAG GAG GGC CTC CCG GAG TAT GTG GCC GGC GTA CAG GCG CAT TTT      594
Ser Glu Glu Gly Leu Pro Glu Tyr Val Ala Gly Val Gln Ala His Phe
                155                 160                 165

CTG GCA GAG CTG CGC GCG CGG GAA GAG CGG TAC GCG GGC CTG TTT TTG      642
Leu Ala Glu Leu Arg Ala Arg Glu Glu Arg Tyr Ala Gly Leu Phe Leu
            170                 175                 180

GGC TAC TGC CGC GCG CTG CTG CAG CAC CTG CGC GCG ACG GCG GCG CGT      690
Gly Tyr Cys Arg Ala Leu Leu Gln His Leu Arg Ala Thr Ala Ala Arg
       185                 190                 195

GGC CGA GGC GCG GCG GGC GCG GGC GCC CAG GCA GAC CGC CTG CGG CAG      738
Gly Arg Gly Ala Ala Gly Ala Gly Ala Gln Ala Asp Arg Leu Arg Gln
   200                 205                 210

CTG GTG GCG GCG CGG TAC TAC CGC GAG GCG AGC GCG CTG GCG CGG CTG      786
Leu Val Ala Ala Arg Tyr Tyr Arg Glu Ala Ser Ala Leu Ala Arg Leu
215                 220                 225                 230

GCC TTT GCG CAT ATG TAC GTG GCG ACG GCG CGC GAA GTC TCT TGG CGC      834
Ala Phe Ala His Met Tyr Val Ala Thr Ala Arg Glu Val Ser Trp Arg
                235                 240                 245

CTG CAC TCC CAG CAG AGC CAG GCG CAG GGC GTG TTC GTT TCG CTG TAC      882
Leu His Ser Gln Gln Ser Gln Ala Gln Gly Val Phe Val Ser Leu Tyr
            250                 255                 260

TAT GCT TGG CCG CAG CGG CGG CAG TTC ACC TGC CTG TTC CAC CCC GTG      930
Tyr Ala Trp Pro Gln Arg Arg Gln Phe Thr Cys Leu Phe His Pro Val
       265                 270                 275

CTG TTC AAC CAC GGC GTC GTG GCG CTG GAG GAC GGC TTC TTG GAC GCG      978
Leu Phe Asn His Gly Val Val Ala Leu Glu Asp Gly Phe Leu Asp Ala
   280                 285                 290

GCG GAG CTG CGG CGG CTA AAC TAC CGG CGT CGG GAG CTG GGG CTG CCG     1026
Ala Glu Leu Arg Arg Leu Asn Tyr Arg Arg Arg Glu Leu Gly Leu Pro
295                 300                 305                 310

CTG GTC CGC GCG GGG CTG GTC GAG GTT GAA GTG GGG CCT CTG GTG GAG     1074
Leu Val Arg Ala Gly Leu Val Glu Val Glu Val Gly Pro Leu Val Glu
                315                 320                 325

GAG CCG CCG TTT TCG GGA AGC TTG CCG CGG GCG CTG GGC TTC CTG AAT     1122
Glu Pro Pro Phe Ser Gly Ser Leu Pro Arg Ala Leu Gly Phe Leu Asn
            330                 335                 340

TAC CAA GTA CGC GCG AAG ATG GGC GCG CCC GCC GAG GCC GGC GGG CGG     1170
Tyr Gln Val Arg Ala Lys Met Gly Ala Pro Ala Glu Ala Gly Gly Arg
       345                 350                 355

CTG GCG CCG GAG CGG GAG CAC TCG TAC GCG CGG CCG CGC GGC GCG ATC     1218
Leu Ala Pro Glu Arg Glu His Ser Tyr Ala Arg Pro Arg Gly Ala Ile
   360                 365                 370

AAC TAC GGG ACG ACT CCA GAG GCC ATG TTG CGG CCC CCG TCG CCG AGC     1266
Asn Tyr Gly Thr Thr Pro Glu Ala Met Leu Arg Pro Pro Ser Pro Ser
```

-continued

```
375                 380                 385                 390

GAA GTG CTG CCG TGC GAC CCC GCG CCA GCG GCT ACC GTG CGC GTG GCG      1314
Glu Val Leu Pro Cys Asp Pro Ala Pro Ala Ala Thr Val Arg Val Ala
                395                 400                 405

AGC CCC GCC ACA CAT CTG GCT CAG GCG CCT TCA GCC AAG GGC GCC GCC      1362
Ser Pro Ala Thr His Leu Ala Gln Ala Pro Ser Ala Lys Gly Ala Ala
            410                 415                 420

CCG GCC GAG TTT GCC GCC TTG GCT GGG CTT GCA AGG CCC GGT CCG GCC      1410
Pro Ala Glu Phe Ala Ala Leu Ala Gly Leu Ala Arg Pro Gly Pro Ala
        425                 430                 435

CCG CTC GCG GCG GCC CCG GCC CAA GCC CCG TTC GCA GCG GCC TTG GCC      1458
Pro Leu Ala Ala Ala Pro Ala Gln Ala Pro Phe Ala Ala Ala Leu Ala
    440                 445                 450

TTA GCC GAG CCC GCG GCA GCC CTG GCC CCG GCC CCG CTT GCG GCG GCC      1506
Leu Ala Glu Pro Ala Ala Ala Leu Ala Pro Ala Pro Leu Ala Ala Ala
455                 460                 465                 470

CCA GCC GAG CCC GCG GCG GCC GTC GCC GGG CCA AGC CCG GCA AAC CCA      1554
Pro Ala Glu Pro Ala Ala Ala Val Ala Gly Pro Ser Pro Ala Asn Pro
                475                 480                 485

TTC GGC GGC ACG TAT GAC GCG CTG CTG GGG GAC CGC CTC AAC CAG CTG      1602
Phe Gly Gly Thr Tyr Asp Ala Leu Leu Gly Asp Arg Leu Asn Gln Leu
            490                 495                 500

CTG GAC TTC TAAGGGCGGG CGGGCAGTGG CGCTTTCGAC CCGGCGCGTG              1651
Leu Asp Phe
        505

GCGTTTGCGA GGCCTCCCTC TGGCGTAAGG CCTCGTGGCG CCGCCCTGCG GGCGGCGCGA   1711

GCGTATAAAA GCCACTTGGG TCTACACGGG ATTTAGTTTT CGCGCCCGCG GCTTTCTAGG   1771

CGCCCTTAGA CCCCATG                                                  1788
```

(2) INFORMATION FOR SEQ ID NO:2:

(i) SEQUENCE CHARACTERISTICS:
(A) LENGTH: 505 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Gly Arg Ile Lys Thr Ala Gly Arg Ala Leu Ala Ser Gln Cys
  1               5                  10                  15

Gly Gly Ala Ala Ala Ala Thr Met Asp Pro Tyr Asp Ala Ile Glu Ala
             20                  25                  30

Phe Asp Asp Ser Leu Leu Gly Ser Pro Leu Ala Ala Gly Pro Leu Tyr
         35                  40                  45

Asp Gly Pro Ser Pro Ala Arg Phe Ala Leu Pro Pro Pro Arg Pro Ala
     50                  55                  60

Pro Leu Ala Ala Leu Leu Glu Arg Met Gln Ala Glu Leu Gly Phe Pro
 65                  70                  75                  80

Asp Gly Pro Ala Leu Leu Arg Ala Met Glu Arg Trp Asn Glu Asp Leu
                 85                  90                  95

Phe Ser Cys Leu Pro Thr Asn Ala Asp Leu Tyr Ala Asp Ala Ala Leu
            100                 105                 110

Leu Ser Ala Asp Ala Asp Ala Val Val Gly Ala Met Tyr Leu Ala Val
        115                 120                 125

Pro Gly Asp Ala Glu Arg Leu Asp Leu Asn Ala His Ala Asn Gln Pro
    130                 135                 140
```

-continued

```
Leu Pro Ala Pro Pro Ala Ser Glu Glu Gly Leu Pro Glu Tyr Val Ala
145                 150                 155                 160

Gly Val Gln Ala His Phe Leu Ala Glu Leu Arg Ala Arg Glu Glu Arg
                165                 170                 175

Tyr Ala Gly Leu Phe Leu Gly Tyr Cys Arg Ala Leu Leu Gln His Leu
            180                 185                 190

Arg Ala Thr Ala Ala Arg Gly Arg Gly Ala Ala Gly Ala Gly Ala Gln
        195                 200                 205

Ala Asp Arg Leu Arg Gln Leu Val Ala Ala Arg Tyr Tyr Arg Glu Ala
    210                 215                 220

Ser Ala Leu Ala Arg Leu Ala Phe Ala His Met Tyr Val Ala Thr Ala
225                 230                 235                 240

Arg Glu Val Ser Trp Arg Leu His Ser Gln Gln Ser Gln Ala Gln Gly
                245                 250                 255

Val Phe Val Ser Leu Tyr Tyr Ala Trp Pro Gln Arg Arg Gln Phe Thr
            260                 265                 270

Cys Leu Phe His Pro Val Leu Phe Asn His Gly Val Val Ala Leu Glu
        275                 280                 285

Asp Gly Phe Leu Asp Ala Ala Glu Leu Arg Arg Leu Asn Tyr Arg Arg
    290                 295                 300

Arg Glu Leu Gly Leu Pro Leu Val Arg Ala Gly Leu Val Glu Val Glu
305                 310                 315                 320

Val Gly Pro Leu Val Glu Glu Pro Pro Phe Ser Gly Ser Leu Pro Arg
                325                 330                 335

Ala Leu Gly Phe Leu Asn Tyr Gln Val Arg Ala Lys Met Gly Ala Pro
            340                 345                 350

Ala Glu Ala Gly Gly Arg Leu Ala Pro Glu Arg Glu His Ser Tyr Ala
        355                 360                 365

Arg Pro Arg Gly Ala Ile Asn Tyr Gly Thr Thr Pro Glu Ala Met Leu
    370                 375                 380

Arg Pro Pro Ser Pro Ser Glu Val Leu Pro Cys Asp Pro Ala Pro Ala
385                 390                 395                 400

Ala Thr Val Arg Val Ala Ser Pro Ala Thr His Leu Ala Gln Ala Pro
                405                 410                 415

Ser Ala Lys Gly Ala Ala Pro Ala Glu Phe Ala Ala Leu Ala Gly Leu
            420                 425                 430

Ala Arg Pro Gly Pro Ala Pro Leu Ala Ala Ala Pro Ala Gln Ala Pro
        435                 440                 445

Phe Ala Ala Ala Leu Ala Leu Ala Glu Pro Ala Ala Ala Leu Ala Pro
    450                 455                 460

Ala Pro Leu Ala Ala Ala Pro Ala Glu Pro Ala Ala Ala Val Ala Gly
465                 470                 475                 480

Pro Ser Pro Ala Asn Pro Phe Gly Gly Thr Tyr Asp Ala Leu Leu Gly
                485                 490                 495

Asp Arg Leu Asn Gln Leu Leu Asp Phe
            500                 505
```

(2) INFORMATION FOR SEQ ID NO:3:

(i) SEQUENCE CHARACTERISTICS:
- (A) LENGTH: 7 amino acids
- (B) TYPE: amino acid
- (C) STRANDEDNESS: single
- (D) TOPOLOGY: linear (xi) SEQUENCE DESCRIPTION: SEQ ID NO:3:

Ile Asp Ser Gly Tyr Arg Gly
1 5

(2) INFORMATION FOR SEQ ID NO:4:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:4:

Ile Asp Ala Gly Thr Arg Gly
1 5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:5:

Glu Asp Ala Gly Phe Asp Ile
1 5

(2) INFORMATION FOR SEQ ID NO:6:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:6:

CAAAGCTTAT HGAYTCNGGN TAYCGNGG 28

(2) INFORMATION FOR SEQ ID NO:7:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:7:

CAAAGCTTAT HGAYTCNGGN TAYAGRGG 28

(2) INFORMATION FOR SEQ ID NO:8:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:8:

CAAAGCTTAT HGAYGCNGGN TAYCGNGG 28

(2) INFORMATION FOR SEQ ID NO:9:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:9:

```
CAGAATTCTA RTCRAANCCN GCRTCYTC                                   28
```

(2) INFORMATION FOR SEQ ID NO:10:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:10:

```
CAGAATTCTA RTCRTANCCN GCRTCYTC                                   28
```

(2) INFORMATION FOR SEQ ID NO:11:

(i) SEQUENCE CHARACTERISTICS:
(A) LENGTH: 1851 base pairs
(B) TYPE: nucleic acid
(C) STRANDEDNESS: single
(D) TOPOLOGY: linear (ix) FEATURE:
(A) NAME/KEY: CDS
(B) LOCATION: 647..1621

(xi) SEQUENCE DESCRIPTION: SEQ ID NO:11:

```
CCTCGAGCGG CGGGCCGGCG CGGCGGCGGG CGCAGCTACG GTCGTCCCCG CGGCTGCGGC     60

TCGATCGCGG CCGCGGGCGG CGGGCTGGAC GGCTGCAGCG CTGGCGCACG CACGGACGCT    120

AGCGCGCCGC CCGCTCGGCT CGGGTCCGCT CGTCGCGGCG CGCAGCTCTT CGTATACGTG    180

GTCATCCGAG CCGGACTCGT AGTCATAGAG GCTGTTTTCT CGCACCCAAA GGTCGCTGTA    240

CTCGTAATCG TCCTCGTCTT CGGAGGGCCT GTGGAACCGG GCCATGGCAA GCGAGTCGGC    300

GGGCCGGCGG GCGTGCAGCT CAAAGCGGGT CGGGCCGAGT GCGAAAAAGG CAGCGGTCGC    360

CGGGACCGCG AGCTTTATAT ACAAGTTACT CCGCAGCGTT GCGGTCAATC AGCCCCGCCC    420

CCGCGACTCC TTTTTATTGG GCCCGCTGGC GCCCATGAGC CTAAAGCAAA GCCCGTACGC    480

GTACAGGGCC ACGGCGACCA TTACCGCGGT CAGGGCCACG TAAAAAACAA CCAGGGCCTG    540

CGGTGGCTCC GAGAGCGGCA CCCCGCGCGC GTAGCAGCCT GCGCTCCAAA AGTCCATTGC    600

CCCCTCGCGC CGCATCGCGT CTAGCAGGGG GTCGCGGCCG CGCACG ATG GCA AAC       655
                                                  Met Ala Asn

AGC GCG GCG GCC ACA ACC GCA ACG ATG AGC GGC GAC CGC GGC ATC CTC      703
Ser Ala Ala Ala Thr Thr Ala Thr Met Ser Gly Asp Arg Gly Ile Leu
    510                 515                 520

GTC GTA GAG CTC AAC GCG GAG GCG GCC CCC TGG CGG TTG GAA AGC TGC      751
Val Val Glu Leu Asn Ala Glu Ala Ala Pro Trp Arg Leu Glu Ser Cys
525                 530                 535                 540

TGT GAG CCC GAC TCG CTG GCG CTC TGG GGC CCA ATT GCG CCA GCA GCA      799
Cys Glu Pro Asp Ser Leu Ala Leu Trp Gly Pro Ile Ala Pro Ala Ala
                545                 550                 555

AAG CGA GAT GAA ACA GCC CCG TCG GGA TCT CTC CTT TAT AGC CGG CTG      847
Lys Arg Asp Glu Thr Ala Pro Ser Gly Ser Leu Leu Tyr Ser Arg Leu
            560                 565                 570

ATT AAT TTA AAC ATG AAG GCG GCC GCG CCC GGC GGA TAT GCC ATT ATA      895
Ile Asn Leu Asn Met Lys Ala Ala Ala Pro Gly Gly Tyr Ala Ile Ile
        575                 580                 585

ATG TCG CAA ATG CGC TCG GGT GAC ACA CAC ATG CCC CGC CCA CCA GCC      943
Met Ser Gln Met Arg Ser Gly Asp Thr His Met Pro Arg Pro Pro Ala
    590                 595                 600
```

-continued

```
GTG GCC GTC GGC ATC GTC GAC TCG GGC TAC TCG GGG ATC TTG CGC GCC      991
Val Ala Val Gly Ile Val Asp Ser Gly Tyr Ser Gly Ile Leu Arg Ala
605                 610                 615                 620

ATC GTC TGG GCG CCC GAG TCC GCA GCG GCC GCT CCC CCG GCG GGG CTT     1039
Ile Val Trp Ala Pro Glu Ser Ala Ala Ala Ala Pro Pro Ala Gly Leu
                625                 630                 635

GCG CTG CGG CTG ACG CTC GCG CGG CTA ACC ACC ACG CTG CCT CGC CTC     1087
Ala Leu Arg Leu Thr Leu Ala Arg Leu Thr Thr Thr Leu Pro Arg Leu
            640                 645                 650

ATC GCC GTC GAC GAC GAC GCA AAC GCC GGG ACA GAG GCG GGC GTC GAA     1135
Ile Ala Val Asp Asp Asp Ala Asn Ala Gly Thr Glu Ala Gly Val Glu
        655                 660                 665

GTG CCC TTC TTT GCC ACG TTC GCC CCC AAA CGC GAC GAG GAC GCC GGG     1183
Val Pro Phe Phe Ala Thr Phe Ala Pro Lys Arg Asp Glu Asp Ala Gly
    670                 675                 680

TAC GAT ATT GCC ATG CCA TAC ACG GCC GTC TTG GCA CCC GGG GAA AAT     1231
Tyr Asp Ile Ala Met Pro Tyr Thr Ala Val Leu Ala Pro Gly Glu Asn
685                 690                 695                 700

TTA CAC GTG CGG CTG CCC GTA GCC TAC GCG GCA GAC GCC CAC GCT GCC     1279
Leu His Val Arg Leu Pro Val Ala Tyr Ala Ala Asp Ala His Ala Ala
                705                 710                 715

GCG CCC TAC GTG TTT GGT CGA TCG TCC TGC AAC CTT CGG GGG CTG ATC     1327
Ala Pro Tyr Val Phe Gly Arg Ser Ser Cys Asn Leu Arg Gly Leu Ile
            720                 725                 730

GTC CTG CCG ACA GCC TGG CCC CCC GGG GAG CCC TGC CGC TTT GTC TTG     1375
Val Leu Pro Thr Ala Trp Pro Pro Gly Glu Pro Cys Arg Phe Val Leu
        735                 740                 745

CGA AAC GTC ACG CAG GAA CCG CTC GTT GCT GCC GCA GGC CAG CGC GTG     1423
Arg Asn Val Thr Gln Glu Pro Leu Val Ala Ala Ala Gly Gln Arg Val
    750                 755                 760

GCG CAG CTG CTT CTG CTG GCA CGG CGC CTC GAG TGG CTT CCG TCC GGC     1471
Ala Gln Leu Leu Leu Leu Ala Arg Arg Leu Glu Trp Leu Pro Ser Gly
765                 770                 775                 780

CTC AAC GAC CGC GAG CCC TTC CCA ACT AGC CCT CGC GCA GCA CCG CCC     1519
Leu Asn Asp Arg Glu Pro Phe Pro Thr Ser Pro Arg Ala Ala Pro Pro
                785                 790                 795

GCC CCT GGG GCC CCG CGC CTG CGC TGG CGC CGC GTC GCC GAT CTC GCC     1567
Ala Pro Gly Ala Pro Arg Leu Arg Trp Arg Arg Val Ala Asp Leu Ala
            800                 805                 810

GCG GCG GTG CCC CCC TCT GCG CGC GGG CCG CGC GGC TTT GGG TCC ACC     1615
Ala Ala Val Pro Pro Ser Ala Arg Gly Pro Arg Gly Phe Gly Ser Thr
        815                 820                 825

GGG CTG TAAAACAAAG CACATTAAAG TACACCGACT CCACCACACA CGTGTTTTGC      1671
Gly Leu
    830

GTATACTTAT TTTGCTTTTA TTGCACCGGG CTACGCCGCA AGCTGCAAAA CGGCGGGGGA   1731

AGAAGCGGCG GCCGCCGCGC GCCCCGCGCG GCTAGGTGGT TTTGTGGCGG CCGCCTCTGC   1791

AGGCGCCACC GGCGGTGCCG GAGACACGGC GACCGGCGCC GAGGCGGCCG GCTGCCGCGG   1851
```

(2) INFORMATION FOR SEQ ID NO:12:

(i) SEQUENCE CHARACTERISTICS:
(A) LENGTH: 325 amino acids
(B) TYPE: amino acid
(D) TOPOLOGY: linear (ii) MOLECULE TYPE: protein (xi) SEQUENCE DESCRIPTION: SEQ ID NO:12:

-continued

```
Met Ala Asn Ser Ala Ala Ala Thr Thr Ala Thr Met Ser Gly Asp Arg
  1               5                  10                  15

Gly Ile Leu Val Val Glu Leu Asn Ala Glu Ala Ala Pro Trp Arg Leu
             20                  25                  30

Glu Ser Cys Cys Glu Pro Asp Ser Leu Ala Leu Trp Gly Pro Ile Ala
         35                  40                  45

Pro Ala Ala Lys Arg Asp Glu Thr Ala Pro Ser Gly Ser Leu Leu Tyr
     50                  55                  60

Ser Arg Leu Ile Asn Leu Asn Met Lys Ala Ala Ala Pro Gly Gly Tyr
 65                  70                  75                  80

Ala Ile Ile Met Ser Gln Met Arg Ser Gly Asp Thr His Met Pro Arg
                 85                  90                  95

Pro Pro Ala Val Ala Val Gly Ile Val Asp Ser Gly Tyr Ser Gly Ile
            100                 105                 110

Leu Arg Ala Ile Val Trp Ala Pro Glu Ser Ala Ala Ala Ala Pro Pro
        115                 120                 125

Ala Gly Leu Ala Leu Arg Leu Thr Leu Ala Arg Leu Thr Thr Thr Leu
    130                 135                 140

Pro Arg Leu Ile Ala Val Asp Asp Asp Ala Asn Ala Gly Thr Glu Ala
145                 150                 155                 160

Gly Val Glu Val Pro Phe Phe Ala Thr Phe Ala Pro Lys Arg Asp Glu
                165                 170                 175

Asp Ala Gly Tyr Asp Ile Ala Met Pro Tyr Thr Ala Val Leu Ala Pro
            180                 185                 190

Gly Glu Asn Leu His Val Arg Leu Pro Val Ala Tyr Ala Ala Asp Ala
        195                 200                 205

His Ala Ala Ala Pro Tyr Val Phe Gly Arg Ser Ser Cys Asn Leu Arg
    210                 215                 220

Gly Leu Ile Val Leu Pro Thr Ala Trp Pro Pro Gly Glu Pro Cys Arg
225                 230                 235                 240

Phe Val Leu Arg Asn Val Thr Gln Glu Pro Leu Val Ala Ala Ala Gly
                245                 250                 255

Gln Arg Val Ala Gln Leu Leu Leu Leu Ala Arg Arg Leu Glu Trp Leu
            260                 265                 270

Pro Ser Gly Leu Asn Asp Arg Glu Pro Phe Pro Thr Ser Pro Arg Ala
        275                 280                 285

Ala Pro Pro Ala Pro Gly Ala Pro Arg Leu Arg Trp Arg Arg Val Ala
    290                 295                 300

Asp Leu Ala Ala Ala Val Pro Pro Ser Ala Arg Gly Pro Arg Gly Phe
305                 310                 315                 320

Gly Ser Thr Gly Leu
                325
```

(2) INFORMATION FOR SEQ ID NO:13:

(i) SEQUENCE CHARACTERISTICS:
(A) LENGTH: 700 base pairs
(B) TYPE: nucleic acid
(C) STRANDEDNESS: single
(D) TOPOLOGY: linear (ix) FEATURE:
(A) NAME/KEY: CDS
(B) LOCATION: 253..540

(xi) SEQUENCE DESCRIPTION: SEQ ID NO:13:

```
ACGGCCACGG CTGGTGGGCG GGGCATGTGT GTGTCACCCG AGCGCATTTG CGACATTATA     60
```

-continued

```
ATGGCATATC CGCCGGGCGC GGCCGCCTTC ATGTTTAAAT TAATCAGCCG GCTATAAAGG    120

AGAGATCCCG ACGGGGCTGT TTCATCTCGC TTTGCTGCTG GCGCAATTGG GCCCCAGAGC    180

GCCAGCGAGT CGGGCTCACA GCAGCTTTCC AACCGCCAGG GGGCCGCCTC CGCGTTGAGC    240

TCTACGACGA GG ATG CCG CGG TCG CCG CTC ATC GTT GCG GTT GTG GCC        288
              Met Pro Arg Ser Pro Leu Ile Val Ala Val Val Ala
                              330                 335

GCC GCG CTG TTT GCC ATC GTG CGC GGC CGC GAC CCC CTG CTA GAC GCG      336
Ala Ala Leu Phe Ala Ile Val Arg Gly Arg Asp Pro Leu Leu Asp Ala
        340                 345                 350

ATG CGG CGC GAG GGG GCA ATG GAC TTT TGG AGC GCA GGC TGC TAC GCG      384
Met Arg Arg Glu Gly Ala Met Asp Phe Trp Ser Ala Gly Cys Tyr Ala
    355                 360                 365

CGC GGG GTG CCG CTC TCG GAG CCA CCG CAG GCC CTG GTT GTT TTT TAC      432
Arg Gly Val Pro Leu Ser Glu Pro Pro Gln Ala Leu Val Val Phe Tyr
370                 375                 380                 385

GTG GCC CTG ACC GCG GTA ATG GTC GCC GTG GCC CTG TAC GCG TAC GGG      480
Val Ala Leu Thr Ala Val Met Val Ala Val Ala Leu Tyr Ala Tyr Gly
                390                 395                 400

CTT TGC TTT AGG CTC ATG GGC GCC AGC GGG CCC AAT AAA AAG GAG TCG      528
Leu Cys Phe Arg Leu Met Gly Ala Ser Gly Pro Asn Lys Lys Glu Ser
            405                 410                 415

CGG GGG CGG GGC TGATTGACCG CAACGCTGCG GAGTAACTTG TATATAAAGC          580
Arg Gly Arg Gly
        420

TCGCGGTCCC GGCGACCGCT GCCTTTTTCG CACTCGGCCC GACCCGCTTT GAGCTGCACG    640

CCCGCCGGCC CGCCGACTCG CTTGCCATGG CCCGGTTCCA CAGGCCCTCC GAAGACGAGG    700
```

(2) INFORMATION FOR SEQ ID NO:14:

(i) SEQUENCE CHARACTERISTICS:
(A) LENGTH: 96 amino acids
(B) TYPE: amino acid
(D) TOPOLOGY: linear (ii) MOLECULE TYPE: protein (xi) SEQUENCE DESCRIPTION: SEQ ID NO:14:

```
Met Pro Arg Ser Pro Leu Ile Val Ala Val Val Ala Ala Ala Leu Phe
  1               5                  10                  15

Ala Ile Val Arg Gly Arg Asp Pro Leu Leu Asp Ala Met Arg Arg Glu
             20                  25                  30

Gly Ala Met Asp Phe Trp Ser Ala Gly Cys Tyr Ala Arg Gly Val Pro
        35                  40                  45

Leu Ser Glu Pro Pro Gln Ala Leu Val Val Phe Tyr Val Ala Leu Thr
     50                  55                  60

Ala Val Met Val Ala Val Ala Leu Tyr Ala Tyr Gly Leu Cys Phe Arg
 65                  70                  75                  80

Leu Met Gly Ala Ser Gly Pro Asn Lys Lys Glu Ser Arg Gly Arg Gly
                 85                  90                  95
```

(2) INFORMATION FOR SEQ ID NO:15:

(i) SEQUENCE CHARACTERISTICS:
(A) LENGTH: 349 base pairs
(B) TYPE: nucleic acid
(C) STRANDEDNESS: single
(D) TOPOLOGY: linear (ix) FEATURE:

```
        (A) NAME/KEY: CDS
        (B) LOCATION: 157..348

      (xi) SEQUENCE DESCRIPTION: SEQ ID NO:15:

GGCCGGGCTG GGCGCGTGCG TACACGGCGG ATCTCGTTTG TGACGTTATC GGGTTTTTCG     60

CGCCCCGGGC GTGGATGCGC GTGTGCCTGG GGGGCACGTA GTATAAAACG AGCGGGGGGC    120

CGCGGGCGCA CTGCGCGCGC CGCCCCACAC CGCGCC ATG GAC CGC CAG AGC GAG      174
                                        Met Asp Arg Gln Ser Glu
                                                    100

CCT CCG CGC GCG CCC GCC TAC ACG GGC GGG CTG GTC TCC GGT CTT GTG      222
Pro Pro Arg Ala Pro Ala Tyr Thr Gly Gly Leu Val Ser Gly Leu Val
        105                 110                 115

CTG TCG AAC ATC GAA GTG GCC TGC CAC CGC GCG CTG TTC AGC TTT TTC      270
Leu Ser Asn Ile Glu Val Ala Cys His Arg Ala Leu Phe Ser Phe Phe
    120                 125                 130

CAG CAG GTG CGA TCG GAC GAC AAC GGC CTG TAC GCG GCC GCC TTT GAC      318
Gln Gln Val Arg Ser Asp Asp Asn Gly Leu Tyr Ala Ala Ala Phe Asp
135                 140                 145                 150

CGC CTC TTG GGC ACG TAC TGC AAC ACG CTG A                            349
Arg Leu Leu Gly Thr Tyr Cys Asn Thr Leu
                155                 160


(2) INFORMATION FOR SEQ ID NO:16:

     (i) SEQUENCE CHARACTERISTICS:
          (A) LENGTH: 64 amino acids
          (B) TYPE: amino acid
          (D) TOPOLOGY: linear

    (ii) MOLECULE TYPE: protein

          (xi) SEQUENCE DESCRIPTION: SEQ ID NO:16:

Met Asp Arg Gln Ser Glu Pro Pro Arg Ala Pro Ala Tyr Thr Gly Gly
  1               5                  10                  15

Leu Val Ser Gly Leu Val Leu Ser Asn Ile Glu Val Ala Cys His Arg
             20                  25                  30

Ala Leu Phe Ser Phe Phe Gln Gln Val Arg Ser Asp Asp Asn Gly Leu
        35                  40                  45

Tyr Ala Ala Ala Phe Asp Arg Leu Leu Gly Thr Tyr Cys Asn Thr Leu
     50                  55                  60


(2) INFORMATION FOR SEQ ID NO:17:

     (i) SEQUENCE CHARACTERISTICS:
          (A) LENGTH: 1499 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 390..1163

        (xi) SEQUENCE DESCRIPTION: SEQ ID NO:17:

CGGTTGTGGC CGCCGCGCTG TTTGCCATCG TGCGCGGCCG CGACCCCCTG CTAGACGCGA     60

TGCGGCGCGA GGGGGCAATG GACTTTTGGA GCGCAGGCTG CTACGCGCGC GGGGTGCCGC    120

TCTCGGAGCC ACCGCAGGCC CTGGTTGTTT TTTACGTGGC CCTGACCGCG GTAATGGTCG    180

CCGTGGCCCT GTACGCGTAC GGGCTTTGCT TTAGGCTCAT GGGCGCCAGC GGGCCCAATA    240

AAAAGGAGTC GCGGGGGCGG GGCTGATTGA CCGCAACGCT GCGGAGTAAC TTGTATATAA    300

AGCTCGCGGT CCCGGCGACC GCTGCCTTTT TCGCACTCGG CCCGACCCGC TTTGAGCTGC    360
```

-continued

```
ACGCCCGCCG GCCCGCCGAC TCGCTTGCC ATG GCC CGG TTC CAC AGG CCC TCC      413
                                Met Ala Arg Phe His Arg Pro Ser
                                 65                   70

GAA GAC GAG GAC GAT TAC GAG TAC AGC GAC CTT TGG GTG CGA GAA AAC      461
Glu Asp Glu Asp Asp Tyr Glu Tyr Ser Asp Leu Trp Val Arg Glu Asn
         75                  80                  85

AGC CTC TAT GAC TAC GAG TCC GGC TCG GAT GAC CAC GTA TAC GAA GAG      509
Ser Leu Tyr Asp Tyr Glu Ser Gly Ser Asp Asp His Val Tyr Glu Glu
     90                  95                 100

CTG CGC GCC GCG ACG AGC GGA CCC GAG CCG AGC GGG CGG CGC GCT AGC      557
Leu Arg Ala Ala Thr Ser Gly Pro Glu Pro Ser Gly Arg Arg Ala Ser
105                 110                 115                 120

GTC CGT GCG TGC GCC AGC GCT GCA GCC GTC CAG CCC GCC GCC CGC GGC      605
Val Arg Ala Cys Ala Ser Ala Ala Ala Val Gln Pro Ala Ala Arg Gly
                125                 130                 135

CGC GAT CGA GCC GCA GCC GCG GGG ACG ACC GTA GCT GCG CCC GCC GCC      653
Arg Asp Arg Ala Ala Ala Ala Gly Thr Thr Val Ala Ala Pro Ala Ala
            140                 145                 150

GCG CCG GCC CGC CGC TCG AGC AGC CGG GCG TCC TCG CGC CCG CCG CGA      701
Ala Pro Ala Arg Arg Ser Ser Ser Arg Ala Ser Ser Arg Pro Pro Arg
        155                 160                 165

GCT GCC GCC GAC CCG CCC GTC CTC CGG CCA GCC ACG CGC GGG TCC TCC      749
Ala Ala Ala Asp Pro Pro Val Leu Arg Pro Ala Thr Arg Gly Ser Ser
    170                 175                 180

GGC GGC GCC GGG GCA GTC GCC GTC GGT CCA CCT CGA CCT CGC GCG CCC      797
Gly Gly Ala Gly Ala Val Ala Val Gly Pro Pro Arg Pro Arg Ala Pro
185                 190                 195                 200

CCC GGT GCT AAT GCT GTT GCG TCT GGC CGG CCG CTG GCG TTC AGC GCG      845
Pro Gly Ala Asn Ala Val Ala Ser Gly Arg Pro Leu Ala Phe Ser Ala
                205                 210                 215

GCT CCG AAA ACG CCC AAG GCG CCC TGG TGT GGA CCG ACG CAC GCC TAC      893
Ala Pro Lys Thr Pro Lys Ala Pro Trp Cys Gly Pro Thr His Ala Tyr
            220                 225                 230

AAC CGA ACG ATC TTT TGC GAG GCC GTC GCG CTC GTG GCC GCC GAG TAC      941
Asn Arg Thr Ile Phe Cys Glu Ala Val Ala Leu Val Ala Ala Glu Tyr
        235                 240                 245

GCC CGG CAG GCG GCT GCC AGC GTC TGG GAC TCG GAC CCC CCA AAG AGC      989
Ala Arg Gln Ala Ala Ala Ser Val Trp Asp Ser Asp Pro Pro Lys Ser
    250                 255                 260

AAC GAG CGA TTG GAT CGC ATG TTG AAG TCG GCG GCA ATT CGC ATC CTC     1037
Asn Glu Arg Leu Asp Arg Met Leu Lys Ser Ala Ala Ile Arg Ile Leu
265                 270                 275                 280

GTG TGC GAG GGC TCC GGG CTT CTC GCC GCC GCG AAC GAC ATC TTG GCC     1085
Val Cys Glu Gly Ser Gly Leu Leu Ala Ala Ala Asn Asp Ile Leu Ala
                285                 290                 295

GCG CGG GCC CAG CGC CCC GCC GCG CGC GGG AGC ACA AGC GGC GGG GAA     1133
Ala Arg Ala Gln Arg Pro Ala Ala Arg Gly Ser Thr Ser Gly Gly Glu
            300                 305                 310

AGC CGC CTT CGC GGC GAG CGG GCC CGG CCG TAGCGCGAGC GGGAGGGCTT       1183
Ser Arg Leu Arg Gly Glu Arg Ala Arg Pro
        315                 320

TTTCGACGCG CGCGGCTTAA GCAGCGCGCT GCTGTGCTAG TATGAAAATA AACGCTTGTT   1243

AATTAAACAC ACCAAGCCGA GTTGCGTTGT CTTTGGGATG AGCGGGCGCA TAAAAACCGC   1303

GGGCCGCGCG CTCGCCAGTC AGTGCGGCGG TGCTGCGGCG GCAACCATGG ACCCGTACGA   1363

CGCCATTGAA GCGTTCGATG ACTCCCTGCT CGGGTCGCCG CTCGCGGCGG GGCCGCTTTA   1423

TGACGGCCCG TCCCCCGCGC GGTTCGCGCT GCCGCCCCCG CGCCCGGCTC CCTGGCCGC    1483
```

-continued

```
GTTGCTGGAG CGAATG                                                     1499
```

(2) INFORMATION FOR SEQ ID NO:18:

(i) SEQUENCE CHARACTERISTICS:
(A) LENGTH: 258 amino acids
(B) TYPE: amino acid
(D) TOPOLOGY: linear (ii) MOLECULE TYPE: protein (xi) SEQUENCE DESCRIPTION: SEQ ID NO:18:

```
Met Ala Arg Phe His Arg Pro Ser Glu Asp Glu Asp Asp Tyr Glu Tyr
  1               5                  10                  15

Ser Asp Leu Trp Val Arg Glu Asn Ser Leu Tyr Asp Tyr Glu Ser Gly
             20                  25                  30

Ser Asp Asp His Val Tyr Glu Glu Leu Arg Ala Ala Thr Ser Gly Pro
         35                  40                  45

Glu Pro Ser Gly Arg Arg Ala Ser Val Arg Ala Cys Ala Ser Ala Ala
     50                  55                  60

Ala Val Gln Pro Ala Ala Arg Gly Arg Asp Arg Ala Ala Ala Ala Gly
 65                  70                  75                  80

Thr Thr Val Ala Ala Pro Ala Ala Ala Pro Ala Arg Arg Ser Ser Ser
                 85                  90                  95

Arg Ala Ser Ser Arg Pro Pro Arg Ala Ala Ala Asp Pro Pro Val Leu
            100                 105                 110

Arg Pro Ala Thr Arg Gly Ser Ser Gly Gly Ala Gly Ala Val Ala Val
        115                 120                 125

Gly Pro Pro Arg Pro Arg Ala Pro Pro Gly Ala Asn Ala Val Ala Ser
    130                 135                 140

Gly Arg Pro Leu Ala Phe Ser Ala Ala Pro Lys Thr Pro Lys Ala Pro
145                 150                 155                 160

Trp Cys Gly Pro Thr His Ala Tyr Asn Arg Thr Ile Phe Cys Glu Ala
                165                 170                 175

Val Ala Leu Val Ala Ala Glu Tyr Ala Arg Gln Ala Ala Ala Ser Val
            180                 185                 190

Trp Asp Ser Asp Pro Pro Lys Ser Asn Glu Arg Leu Asp Arg Met Leu
        195                 200                 205

Lys Ser Ala Ala Ile Arg Ile Leu Val Cys Glu Gly Ser Gly Leu Leu
    210                 215                 220

Ala Ala Ala Asn Asp Ile Leu Ala Ala Arg Ala Gln Arg Pro Ala Ala
225                 230                 235                 240

Arg Gly Ser Thr Ser Gly Gly Glu Ser Arg Leu Arg Gly Glu Arg Ala
                245                 250                 255

Arg Pro
```

(2) INFORMATION FOR SEQ ID NO:19:

(i) SEQUENCE CHARACTERISTICS:
(A) LENGTH: 258 amino acids
(B) TYPE: amino acid
(C) STRANDEDNESS: single
(D) TOPOLOGY: linear (xi) SEQUENCE DESCRIPTION: SEQ ID NO:19:

```
Met Ala Arg Phe His Arg Pro Ser Glu Asp Glu Asp Asp Tyr Glu Tyr
1               5                   10                  15

Ser Asp Leu Trp Val Arg Glu Asn Ser Leu Tyr Asp Tyr Glu Ser Gly
```

-continued

```
            20                  25                  30

Ser Asp Asp His Val Tyr Glu Glu Leu Arg Ala Ala Thr Ser Gly Pro
        35                  40                  45

Glu Pro Ser Gly Arg Arg Ala Ser Val Arg Ala Cys Ala Ser Ala Ala
    50                  55                  60

Ala Val Gln Pro Ala Ala Arg Gly Arg Asp Arg Ala Ala Ala Ala Gly
65                  70                  75                  80

Thr Thr Val Ala Ala Pro Ala Ala Ala Pro Ala Arg Arg Ser Ser Ser
                85                  90                  95

Arg Ala Ser Ser Arg Pro Pro Arg Ala Ala Ala Asp Pro Pro Val Leu
            100                 105                 110

Arg Pro Ala Thr Arg Gly Ser Ser Gly Gly Ala Gly Ala Val Ala Val
        115                 120                 125

Gly Pro Pro Arg Pro Arg Ala Pro Pro Gly Ala Asn Ala Val Ala Ser
    130                 135                 140

Gly Arg Pro Leu Ala Phe Ser Ala Ala Pro Lys Thr Pro Lys Ala Pro
145                 150                 155                 160

Trp Cys Gly Pro Thr His Ala Tyr Asn Arg Thr Ile Phe Cys Glu Ala
                165                 170                 175

Val Ala Leu Val Ala Ala Glu Tyr Ala Arg Gln Ala Ala Ala Ser Val
            180                 185                 190

Trp Asp Ser Asp Pro Pro Lys Ser Asn Glu Arg Leu Asp Arg Met Leu
        195                 200                 205

Lys Ser Ala Ala Ile Arg Ile Leu Val Cys Glu Gly Ser Gly Leu Leu
    210                 215                 220

Ala Ala Ala Asn Asp Ile Leu Ala Ala Arg Ala Gln Arg Pro Ala Ala
225                 230                 235                 240

Arg Gly Ser Thr Ser Gly Gly Glu Ser Arg Leu Arg Gly Glu Arg Ala
                245                 250                 255

Arg Pro
```

(2) INFORMATION FOR SEQ ID NO:20:

(i) SEQUENCE CHARACTERISTICS:
(A) LENGTH: 302 amino acids
(B) TYPE: amino acid
(C) STRANDEDNESS: single
(D) TOPOLOGY: linear (xi) SEQUENCE DESCRIPTION: SEQ ID NO:20:

```
Met Ala Ser Ser Asp Gly Asp Arg Leu Cys Arg Ser Asn Ala Val Arg
1               5                   10                  15

Arg Lys Thr Thr Pro Ser Tyr Ser Gly Gln Tyr Arg Thr Ala Arg Arg
            20                  25                  30

Ser Val Val Val Gly Pro Pro Asp Asp Ser Asp Asp Ser Leu Gly Tyr
        35                  40                  45

Ile Thr Thr Val Gly Ala Asp Ser Pro Ser Pro Val Tyr Ala Asp Leu
    50                  55                  60

Tyr Phe Glu His Lys Asn Thr Thr Pro Arg Val His Gln Pro Asn Asp
65                  70                  75                  80

Ser Ser Gly Ser Glu Asp Asp Phe Glu Asp Ile Asp Glu Val Val Ala
                85                  90                  95

Ala Phe Arg Glu Ala Arg Leu Arg His Glu Leu Val Glu Asp Ala Val
            100                 105                 110

Tyr Glu Asn Pro Leu Ser Val Glu Lys Pro Ser Arg Ser Phe Thr Lys
```

-continued

```
        115                 120                 125

Asn Ala Ala Val Lys Pro Lys Leu Glu Asp Ser Pro Lys Arg Ala Pro
    130                 135                 140

Pro Gly Ala Gly Ala Ile Ala Ser Gly Arg Pro Ile Ser Phe Ser Thr
145                 150                 155                 160

Ala Pro Lys Thr Ala Thr Ser Ser Trp Cys Gly Pro Thr Pro Ser Tyr
                165                 170                 175

Asn Lys Arg Val Phe Cys Glu Ala Val Arg Arg Val Ala Ala Met Gln
            180                 185                 190

Ala Gln Lys Ala Ala Glu Ala Ala Trp Asn Ser Asn Pro Pro Arg Asn
        195                 200                 205

Asn Ala Glu Leu Asp Arg Leu Leu Thr Gly Ala Val Ile Arg Ile Thr
    210                 215                 220

Val His Glu Gly Leu Asn Leu Ile Gln Ala Ala Asn Glu Ala Asp Leu
225                 230                 235                 240

Gly Glu Gly Ala Ser Val Ser Lys Arg Gly His Asn Arg Lys Thr Gly
                245                 250                 255

Asp Leu Gln Gly Gly Met Gly Asn Glu Pro Met Tyr Ala Gln Val Arg
            260                 265                 270

Lys Pro Lys Ser Arg Thr Asp Thr Gln Thr Thr Gly Arg Ile Thr Asn
        275                 280                 285

Arg Ser Arg Ala Arg Ser Ala Ser Arg Thr Asp Thr Arg Lys
    290                 295                 300
```

(2) INFORMATION FOR SEQ ID NO:21:

(i) SEQUENCE CHARACTERISTICS:
(A) LENGTH: 301 amino acids
(B) TYPE: amino acid
(C) STRANDEDNESS: single
(D) TOPOLOGY: linear (xi) SEQUENCE DESCRIPTION: SEQ ID NO:21:

```
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175
```

-continued

```
His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Arg Pro Val Glu
    290                 295                 300
```